US007919510B2

(12) United States Patent  
Renton et al.

(10) Patent No.: US 7,919,510 B2  
(45) Date of Patent: Apr. 5, 2011

(54) SUBSTITUTED BENZIMIDAZOLE COMPOUNDS WITH DUAL NOS INHIBITORY ACTIVITY AND MU OPIOID AGONIST ACTIVITY

(75) Inventors: Paul Renton, Toronto (CA); Shawn Maddaford, Mississauga (CA); Suman Rakhit, Mississauga (CA); John Andrews, Mississauga (CA)

(73) Assignee: NeurAxon, Inc, Mississauga (CA)

( * ) Notice: Subject to any disclaimer, the term of this patent is extended or adjusted under 35 U.S.C. 154(b) by 1098 days.

(21) Appl. No.: 11/436,393

(22) Filed: May 18, 2006

(65) Prior Publication Data

US 2008/0214613 A1  Sep. 4, 2008

Related U.S. Application Data

(60) Provisional application No. 60/682,043, filed on May 18, 2005.

(51) Int. Cl.
*A01N 43/40* (2006.01)

(52) U.S. Cl. ............ 514/322; 514/394; 548/309.7; 548/306.1; 546/199

(58) Field of Classification Search ............ 514/322, 514/394; 548/309, 306.1; 546/199
See application file for complete search history.

(56) References Cited

U.S. PATENT DOCUMENTS

| | | | |
|---|---|---|---|
| 2,935,514 A | 5/1960 | Hoffmann et al. | |
| 7,674,809 B2 * | 3/2010 | Makovec et al. | 514/367 |
| 2003/0144286 A1 * | 7/2003 | Frenkel et al. | 514/233.5 |
| 2003/0212070 A1 | 11/2003 | Schwink et al. | |
| 2007/0112038 A1 | 5/2007 | Marlow et al. | |
| 2009/0048112 A1 | 2/2009 | Elliott et al. | |
| 2009/0099019 A1 | 4/2009 | Dietz et al. | |

FOREIGN PATENT DOCUMENTS

| | | |
|---|---|---|
| DE | 123466 | 12/1976 |
| EP | 0262873 | 4/1988 |
| EP | 1 388 341 | 2/2004 |
| EP | 1571142 | 9/2005 |
| JP | 10-265450 | * 10/1998 |
| WO | WO 95/03298 | 2/1995 |
| WO | WO 95/16685 | 6/1995 |
| WO | WO 03/015769 | * 2/2003 |

OTHER PUBLICATIONS

Wermuth, C. G.(The Practice of Medicinal Chemistry: Molecular Variations based on Isosteric Replacement, Academic Press, Oxford (1996), pp. 204-237).*
Wolff, Manfred E. "Burger's Medicinal Chemistry, 5ed, Part I", John Wiley & Sons, 1995, pp. 975-977.*
Banker et al, "Modern Pharmaceutics, 3ed.", Marcel Dekker, New York, 1996, pp. 451 and 596.*
Anderson et al., "Palladium-Catalyzed Amination of Aryl Nonaflates," *J.Org.Chem,.* 68: 9563-9573, 2003.
Antilla et al., "Copper-Catalyzed Coupling of Arylboronic Acids and Amines," *Organic Letters*, 3: 2077-2079, 2001.
Ayhan Kilcigil et al., "Synthesis and Antifungal Properties of Some Benzimidazole Derivatives," *Turk. J. Chem.*, 30: 223-228, 2006.
Baati et al., "An Improved Method for the Preparation of Amidines Via Thiophenylimidic Esters," *Synthesis*, 6: 927-929, 1999.
Boev et al., "Synthesis and Antimicrobial Activity of 5(6)-Isothiocyanatobenzazoles," *Khimiko farmatsevticheskii Zhurnal*, 24: 40-44, 1990 (translation).
Borowicz et al., "7-Nitroindazole Differentially Affects the Anticonvulsant Activity of Antiepileptic Drugs Against Amygdala-Kindled Seizures in Rats," *Epilepsia*, 41: 1112-1118, 2000.
Carroll et al., "Etonitazine. An Improved Synthesis," *J. Med. Chem.*, 18: 318-320, 1975.
Castro et al., "Enhancement of Oral Absorption in Selective 5-HT$_{1D}$ Receptor Agonists: Fluorinated 3-[3-(Piperidin-1-yl)propyl]indoles," *J. Med. Chem.*, 41: 2667-2670, 1998.
Collins et al., "N-Phenylamidines as Selective Inhibitors of Human Neuronal Nitric Oxide Synthase: Structure-Activity Studies and Demonstration of in Vivo Activity," *J. Med. Chem.*, 41: 2858-2871, 1998.
Hobbs et al., "Inhibition of Nitric Oxide Synthase as a Potential Therapeutic Target," *Ann. Rev. Pharmacol. Toxico.*, 39: 191-220, 1999.
Huang et al., "New Ammonia Equivalents for the Pd-Catalyzed Amination of Aryl Halides," *Org. Lett.*, 3: 3417-3419, 2001.
Hunger et al., "Benzimidazol-Derivate and Verwandte Heterocyclen III[1]) Synthese von 1-Aminoalkyl-2-Benzyl-Nitro-Benzimidazolen," *Helv. Chim. Acta.*, 43:1032-1046, 1960 (English abstract included).
Ito et al., "Inhibition of Neuronal Nitric Oxide Synthase Ameliorates Renal Hyperfiltration in Streptozotocin-Induced Diabetic Rat," *J. Lab Clin. Med.*, 138: 177-185, 2001.
Kiss et al., "Inhibition of Neuronal Nitric Oxide Synthase Potentiates the Dimethylphenylpiperazinium-Evoked Carrier-Mediated Release of Noradrenaline from Rat Hippocampal Slices," *Neuroscience Lett.*, 215: 115-118, 1996.
McKay, "The Preparation of N-Substituted-N[1]-Nitroguanidines by the Reaction of Primary Amines with N-Alkyl-N-Nitroso-N[1]-Nitroguanidines[1]," *J. Am. Chem. Soc.*, 71: 1968-1970, 1949.
Schneller et al., "Synthesis of *proximal*-Benzoguanine and a Simplified Synthesis of *proximal*-Benzohypoxanthine," *J. Org. Chem.*, 51: 4067-4070, 1986.
Shearer et al., "S-2-Naphthylmethyl Thioacetimidate Hydrobromide: A New Odorless Reagent For The Mild Synthesis of Substituted Acetamidines," *Tetrahedron Letters*, 38: 179-182, 1997.
Shin, "Increased Expression of Neuronal Nitric Oxide Synthase in Astrocytes and Macrophages in the Spinal Cord of Lewis Rats with Autoimmune Encephalomyelitis," *J. Vet. Sci.*, 2: 195-9, 2001.
Sigmon et al., "Influence of Nitric Oxide Derived From Neuronal Nitric Oxide Synthase on Glomerular Filtration," *Gen. Pharmacol.*, 34: 95-100, 2000.

(Continued)

*Primary Examiner* — Yong Chu
*Assistant Examiner* — Valerie Rodriguez-Garcia
(74) *Attorney, Agent, or Firm* — Clark & Elbing LLP

(57) ABSTRACT

The present invention relates to benzimidazole compounds having dual nitric oxide synthase (NOS) inhibitory activity and agonist activity at the mu-opioid receptor, to pharmaceutical and diagnostic compositions containing them, and to their medical use, particularly as compounds for the treatment or prevention of chronic pain, acute pain, migraine, and neuropathic pain.

24 Claims, No Drawings

OTHER PUBLICATIONS

Thomas et al., "Rapid In-Plate Generation of Benzimidazole Libraries and Amide Formation Using EEDQ," *Tetrahedron Letters*, 38: 5099-5102, 1997.

Wagner et al., "Tuberkulostatisch wirksame N, N'-Diarylthioharnstoffe," *Arzneimittel-Forschung*, 19: 719-730, 1969.

Wang et al., "µ Opiate Receptor: cDNA Cloning and Expression," *Proc.Natl.Acad.Sci USA*, 90: 10230-10234, 1993.

Wang et al., "Human µ Opiate Receptor: cDNA and Genomic Clones, Pharmacologic Characterization and Chromosomal Assignment," *FEBS Lett.*, 338: 217-222, 1994.

Willitzer et al., "Synthese and Antivirale Wirksamkeit von Substituierten 5-Ureido-und-5-Thioureidobenzimidazolderivaten," *Pharmazie* 33: 30-38, 1978.

Wolfe et al., "Simple, Efficient Catalyst System for the Palladium-Catalyzed Amination of Aryl Chlorides, Bromides, and Triflates," *J. Org. Chem.*, 65: 1158-1174, 2000.

International Preliminary Report on Patentability, (PCT/IB2006/003075), issued Nov. 20, 2007.

International Search Report, (PCT/IB2006/003075), mailed Mar. 27, 2007.

Written Opinion of the International Searching Authority, (PCT/IB2006/003075), mailed Mar. 27, 2007.

Extended European Search Report for EP Application No. 06809164.4-2101 dated Jul. 15, 2009.

* cited by examiner

SUBSTITUTED BENZIMIDAZOLE COMPOUNDS WITH DUAL NOS INHIBITORY ACTIVITY AND MU OPIOID AGONIST ACTIVITY

CROSS-REFERENCE TO RELATED APPLICATIONS

This application claims benefit of U.S. Provisional Application No. 60/682,043, filed on May 18, 2005, which is hereby incorporated by reference.

BACKGROUND OF THE INVENTION

The present invention relates to benzimidazole compounds having dual nitric oxide synthase (NOS) inhibitory activity and mu opioid receptor agonist activity, and their therapeutic and diagnostic use.

In clinical practice, pain remains fundamentally undertreated (Dray et al., *Annu. Rev. Pharmacol. Toxicol.* 36:253-280, 1996). In the management of cancer pain, 42% of survey respondents experienced inadequate analgesia (Cleeland et al., *N. Engl. J. Med.* 330:592-596, 1994). As many as 10-20% of adults suffer from debilitating chronic pain where there may be no discernible pathologic basis for the pain, making conditions such as lower back pain and fibromyalgia difficult to treat. Studies of acute pain management revealed that in the postoperative setting, 77% of adults experienced inadequate pain treatment, with most patients describing the pain as moderate to severe (Warfield and Kahn, *Anesthesiology* 83:1090-1094, 1995).

While acute pain associated with nociceptive activation by noxious physical, chemical, and thermal stimuli is protective and subsides after the removal of the stimulus, prolonged activation can lead to sensitization of peripheral nociceptors and hyperalgesia. Eventually, prolonged acute pain and hyperalgesia can evolve into chronic pain (Carr and Goudas, *Lancet* 353:2051-2058, 1999). For example, pain intensity during acute herpes zoster predicts the likelihood of developing postherpetic neuralgia, while rigorous perioperative analgesia for prostatectomy lowers analgesic requirement and improves functional outcome for months afterwards (Carr, *JAMA* 279:1114-1115, 1998). Thus, acute pain can be the initiation phase of an extensive persistent nociceptive and behavorial cascade triggered by tissue injury which, if not suppressed, leads to progressive central sensitization. Even minor injury can therefore lead to chronic pain.

Opioid analgesics have a long history in the management of pain. Opioids such as morphine and codeine, semi-synthetics such as buprenorphine and oxycodone, or synthetic opioids such as fentanyl are important in the management of acute and chronic pain. Unfortunately opioids are limited in their use for acute and chronic pain treatment due to their known side effects, such as respiratory depression, vomiting, sedation, constipation, addiction, dependency, and the development of tolerance. In addition, neuropathic pain can be particularly insensitive to opioid treatment (Benedetti et al., *Pain* 74:205-211, 1998) and is still considered to be relatively refractory to opioid analgesics (MacFarlane et al., *Pharmacol. Ther.* 75:1-19, 1997 and Watson, *Clin. J. Pain* 16:S49-S55, 2000). While dose escalation can overcome reduced opioid effectiveness, it is limited by increased side effects and tolerance.

Nitric oxide (NO) has diverse roles both in normal and pathological processes, including the regulation of blood pressure, in neurotransmission, and in the macrophage defense systems (Snyder et al., *Scientific American*, May 1992:68). NO is synthesized by three isoforms of nitric oxide synthase; a constitutive form in endothelial cells (eNOS), a constitutive form in neuronal cells (nNOS), and an inducible form found in macrophage cells (iNOS). These enzymes are homodimeric proteins that catalyze a five-electron oxidation of L-arginine, yielding NO and citrulline. The role of NO produced by each of the NOS isoforms is quite unique. Overstimulation or overproduction of individual NOS isoforms plays a role in several disorders, including septic shock, arthritis, diabetes, ischemia-reperfusion injury, pain, and various neurodegenerative diseases (Kerwin, et al., *J. Med. Chem.* 38:4343, 1995).

Evidence suggests that the combination of an opioid analgesic with an inhibitor of neuronal nitric oxide synthase (nNOS) would be beneficial. Morphine administration is known to activate the NOS system and limits the analgesic action of this drug (Li and Clark, *Mol. Brain. Res.* 95(1-2): 96-102, 2001; Machelska et al., *NeuroReport* 8:2743-2747, 1997; Wong et al., *Br. J. Anaesth.* 85:587, 2000; and Xiangqi and Clark, *Mol. Brain. Res.* 95:96-102, 2001). However, it has been shown that the combined systemic administration of morphine and L-NAME can attenuate mechanical and cold allodynia at subthreshold doses where neither drug administered alone was effective (Ulugol et al., *Neurosci. Res. Com.* 30(3):143-153, 2002). The effect of L-NAME co-administration on morphine analgesia appears to be mediated by nNOS, as L-NAME loses is ability to potentiate morphine analgesia in nNOS null-mutant mice (Clark and Xiangqi vide supra). Enhanced analgesia has been demonstrated in a tail-flick or paw pressure model using coadministration of L-NAME or 7-NI with either mu-, delta-, or kappa-selective opioid agonists (Machelska et al., *J. Pharmacol. Exp. Ther.* 282:977-984, 1997).

Evidence also suggests that NOS inhibitors would be useful for preventing opioid tolerance and dependence. Tolerance and dependence resulting from chronic exposure to opioid analgesics, such as morphine, is related to adaptive changes, such as opioid receptor downregulation, receptor internalization, and uncoupling from inhibitory G proteins. Tolerance and dependence can also result from receptors involved in cAMP signal transduction being densensitized, up-regulated, or supersensitized. Other side effects of chronic opioid administration include the development of opioid-induced hyperalgesia (OIH). In a murine model of OIH, the NOS inhibitor L-NAME and NMDA antagonist MK-901 dose-dependently reduced OIH (Li et al., *Mol. Brain. Res.* 86(1,2):56-62, 2001).

Thus, the combination of a selective nNOS inhibitor with an opioid analgesic is expected to enhance opioid analgesia and prevent the development of opioid tolerance, prevent the development of opioid-induced hyperalgesia, and/or minimize side effects. While many drug combinations with opioids have been shown to enhance analgesia or reduce side effects, fewer examples are known for which opioid and non-opioid activity are contained within a single drug and none appear to exist for compounds possessing both NOS inhibitory activity and opioid agonist or antagonist activity.

SUMMARY OF THE INVENTION

It has been found surprisingly that certain 5- and 6-amidine substituted benzimidazole compounds are nitric oxide synthase (NOS) inhibitors and are particularly inhibitory for the nNOS isoform. In addition, these compounds also bind to opioid receptors, and in particular, are agonists for the mu opioid receptor.

Accordingly, the present invention features a compound having the formula:

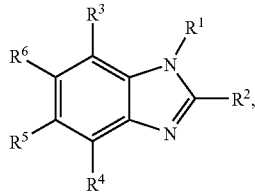

or a pharmaceutically acceptable salt or prodrug thereof, wherein, $R^1$ is optionally substituted $C_{1-6}$ alkyl, optionally substituted $C_{1-4}$ alkaryl, or optionally substituted $C_{1-4}$ alkheterocyclyl;

$R^2$ is H, Hal, optionally substituted $C_{1-6}$ alkyl, optionally substituted $C_{6-10}$ aryl, optionally substituted $C_{1-4}$ alkaryl, optionally substituted $C_{2-9}$ bridged heterocyclyl, optionally substituted $C_{1-4}$ bridged alkheterocyclyl, optionally substituted $C_{2-9}$ heterocyclyl, or optionally substituted $C_{1-4}$ alkheterocyclyl;

each of $R^3$ and $R^4$ is, independently, H, F, $C_{1-6}$ alkyl, or $C_{1-6}$ alkoxy;

$R^5$ is H, nitro, $R^{5A}C(NH)NH(CH_2)_{r5}$, $R^{5A}NHC(NH)NH(CH_2)_{r5}$, or $R^{5A}NHC(S)NH(CH_2)_{r5}$, where r5 is an integer from 0 to 2 and $R^{5A}$ is optionally substituted $C_{1-6}$ alkyl, optionally substituted $C_{6-10}$ aryl, optionally substituted $C_{1-4}$ alkaryl, optionally substituted $C_{2-9}$ heterocyclyl, optionally substituted $C_{1-4}$ alkheterocyclyl, optionally substituted $C_{1-6}$ thioalkoxy, optionally substituted $C_{1-6}$ thioalkyl, optionally substituted $C_{1-4}$ thioalkaryl, optionally substituted aryloyl, optionally substituted $C_{1-4}$ thioalkheterocyclyl; or nitro; and $R^6$ is H, nitro, $R^{6A}C(NH)NH(CH_2)_{r6}$, $R^{6A}NHC(NH)NH(CH_2)_{r6}$, or $R^{6A}NHC(S)NH(CH_2)_{r6}$, where r6 is an integer from 0 to 2 and $R^{6A}$ is optionally substituted $C_{1-6}$ alkyl, optionally substituted $C_{6-10}$ aryl, optionally substituted $C_{1-4}$ alkaryl, optionally substituted $C_{2-9}$ heterocyclyl, optionally substituted $C_{1-4}$ alkheterocyclyl, optionally substituted $C_{1-6}$ thioalkoxy, optionally substituted $C_{1-4}$ thioalkaryl, optionally substituted aryloyl, optionally substituted $C_{1-4}$ thioalkheterocyclyl, or nitro;

where one, but not both, of $R^5$ and $R^6$ is H.

In one embodiment, $R^1$ is optionally substituted $C_{1-4}$ alkheterocyclyl, or an alkylamine-substituted $C_{1-6}$ alkyl, e.g., ethyl substituted at the 2-position with N,N-dimethylamine, N,N-diethylamine, N-aziridine (i.e., azacyclopropane), N-azetidane (i.e., azacyclobutane), N-pyrrolidine (i.e., azacyclopentane), N-piperidine (i.e., azacyclohexane), N-methyl-2-pyrrolidine, N-methyl-4-piperidine, or N-morpholine (i.e., 1-aza-4-oxacyclohexane).

In another embodiment, r5 or r6 is 0.

In certain embodiments, $R^1$ is H, optionally substituted $C_{1-6}$ alkyl, optionally substituted $C_{1-4}$ alkaryl, or optionally substituted $C_{1-4}$ alkheterocyclyl;

$R^2$ is, independently, H, Hal, optionally substituted $C_{1-6}$ alkyl, optionally substituted $C_{6-10}$ aryl, optionally substituted $C_{1-4}$ alkaryl, optionally substituted $C_{2-9}$ heterocyclyl, or optionally substituted $C_{1-4}$ alkheterocyclyl;

each of $R^3$ and $R^4$ is, independently, H, F, $C_{1-6}$ alkyl, or $C_{1-6}$ alkoxy;

$R^5$ is H or $R^{5A}C(NH)NH(CH_2)_{r5}$, wherein r5 is an integer from 0 to 2, $R^{5A}$ is optionally substituted $C_{1-6}$ alkyl, optionally substituted $C_{6-10}$ aryl, optionally substituted $C_{1-4}$ alkaryl, optionally substituted $C_{2-9}$ heterocyclyl, optionally substituted $C_{1-4}$ alkheterocyclyl, optionally substituted $C_{1-6}$ thioalkoxy, optionally substituted $C_{1-4}$ thioalkaryl, or optionally substituted $C_{1-4}$ thioalkheterocyclyl; and $R^6$ is H or $R^{6A}C(NH)NH(CH_2)_{r6}$, wherein r6 is an integer from 0 to 2, $R^{6A}$ is optionally substituted $C_{1-6}$ alkyl, optionally substituted $C_{6-10}$ aryl, optionally substituted $C_{1-4}$ alkaryl, optionally substituted $C_{2-9}$ heterocyclyl, optionally substituted $C_{1-4}$ alkheterocyclyl, optionally substituted $C_{1-6}$ thioalkoxy, optionally substituted $C_{1-4}$ thioalkaryl, or optionally substituted $C_{1-4}$ thioalkheterocyclyl.

In another embodiment, $R^{5A}$ in a compound of formula I is methyl, fluoromethyl, ethyl, n-propyl, i-propyl, n-butyl, i-butyl, t-butyl, thiomethoxy, thioethoxy, thio-n-propyloxy, thio-i-propyloxy, thio-n-butyloxy, thio-i-butyloxy, thio-t-butyloxy, phenyl, benzyl, 2-thienyl, 3-thienyl, 2-furanyl, 3-furanyl, 2-oxazole, 4-oxazole, 5-oxazole, 2-thiazole, 4-thiazole, 5-thiazole, 2-isoxazole, 3-isoxazole, 4-isoxazole, 2-isothiazole, 3-isothiazole, or 4-isothiazole; and $R^{6A}$ is H.

In another embodiment, $R^{6A}$ in a compound of formula I is methyl, fluoromethyl, ethyl, n-propyl, i-propyl, n-butyl, i-butyl, t-butyl, thiomethoxy, thioethoxy, thio-n-propyloxy, thio-i-propyloxy, thio-n-butyloxy, thio-i-butyloxy, thio-t-butyloxy, phenyl, benzyl, 2-thienyl, 3-thienyl, 2-furanyl, 3-furanyl, 2-oxazole, 4-oxazole, 5-oxazole, 2-thiazole, 4-thiazole, 5-thiazole, 2-isoxazole, 3-isoxazole, 4-isoxazole, 2-isothiazole, 3-isothiazole, or 4-isothiazole; and $R^{5A}$ is H.

In another embodiment, one or more of $R^1$ or $R^2$ is not H.

Examples of compounds of formula I include those in which $R^1$ is $(CH_2)_{m1}X^1$, where $X^1$ is selected from the group consisting of:

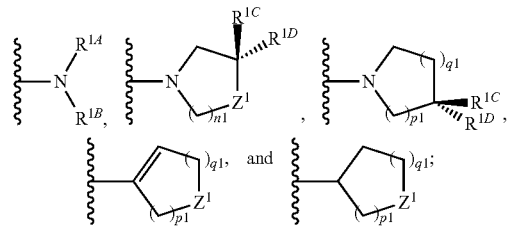

and/or $R^2$ is $(CH_2)_{m2}X^2$, where $X^2$ is selected from the group consisting of:

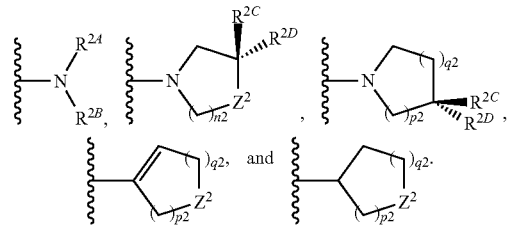

For $X^1$ or $X^2$ group substituents, each of $R^{(x)A}$ and $R^{(x)B}$ is, independently, H, optionally substituted $C_{1-6}$ alkyl, optionally substituted $C_{3-8}$ cycloalkyl, optionally substituted $C_{6-10}$ aryl, optionally substituted $C_{1-4}$ alkaryl, $C_{2-9}$ heterocyclyl, or optionally substituted $C_{1-4}$ alkheterocyclyl; each of $R^{(x)C}$ and $R^{(x)D}$ is, independently, H, OH, $CO_2R^{(x)E}$, or $NR^{(x)F}R^{(x)G}$, wherein each of $R^{(x)E}$, $R^{(x)F}$, and $R^{(x)G}$ is, independently, H, optionally substituted $C_{1-6}$ alkyl, optionally substituted $C_{3-8}$ cycloalkyl, optionally substituted $C_{6-10}$ aryl, optionally substituted $C_{1-4}$ alkaryl, $C_{2-9}$ heterocyclyl, or optionally substituted $C_{1-4}$ alkheterocyclyl, or $R^{(x)C}$ and $R^{(x)D}$ together with the carbon they are bonded to are C=O; $Z^{(x)}$ is $NR^{(x)H}$, $NC(O)R^{(x)H}$, $NC(O)OR^{(x)H}$, $NC(O)NHR^{(x)H}$, $NC(S)R^{(x)H}$, $NC(S)NHR^{(x)H}$, $NS(O)_2R^{(x)H}$, O, S, S(O), or $S(O)_2$, wherein $R^{(x)H}$ is H, optionally substituted $C_{1-6}$ alkyl, optionally substituted $C_{3-8}$ cycloalkyl, optionally substituted $C_{6-10}$ aryl, optionally substituted $C_{1-4}$ alkaryl, $C_{2-9}$ heterocyclyl, or optionally substituted $C_{1-4}$ alkheterocyclyl; m(x) is an integer of 2 to 6; n(x) is an integer of 1 to 4; p(x) is an integer of 0 to 2; and q(x) is an integer of 0 to 5, where (x) is 1 or 2, respectively, with the proviso that when $Z^{(x)}$ is $NC(O)OR^{(x)H}$, $R^{(x)H}$ is not H.

In another example, $R^1$ is $(CH_2)_{m1}X^1$ and/or $R^2$ is $(CH_2)_{m2}X^2$, where $X^1$ and $X^2$ are selected from the group consisting of:

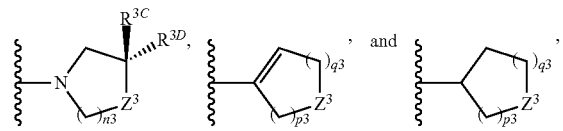

wherein
each of $R^{3C}$ and $R^{3D}$ is, independently, H, OH, $CO_2R^{3E}$, or $NR^{3F}R^{3G}$, wherein each of $R^{3E}$, $R^{3F}$, and $R^{3G}$ is, independently, H, optionally substituted $C_{1-6}$ alkyl, optionally substituted $C_{3-8}$ cycloalkyl, optionally substituted $C_{6-10}$ aryl, optionally substituted $C_{1-4}$ alkaryl, $C_{2-9}$ heterocyclyl, or optionally substituted $C_{1-4}$ alkheterocyclyl, or $R^{3C}$ and $R^{3D}$ together with the carbon they are bonded to are C=O; $Z^3$ is $NC(NH)R^{3H}$, wherein $R^{3H}$ is H, optionally substituted $C_{1-6}$ alkyl, optionally substituted $C_{3-8}$ cycloalkyl, optionally substituted $C_{6-10}$ aryl, optionally substituted $C_{1-4}$ alkaryl, $C_{2-9}$ heterocyclyl, or optionally substituted $C_{1-4}$ alkheterocyclyl; m1 is an integer of 0 to 6; m2 is an integer of 0 to 6; n3 is an integer of 1 to 4; p3 is an integer of 0 to 2; and q3 is an integer of 0 to 5.

$R^1$ and/or $R^2$ may also have the formula

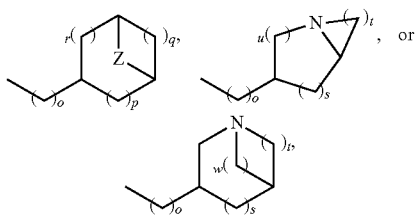

wherein Z is $NR^Z$, o is an integer from 0-3, p is an integer from 1 to 2, q is an integer from 0 to 2, r is an integer from 0 to 1, s is an integer from 0 to 3, u is an integer from 0 to 1, t is an integer from 2 to 7, w is an integer from 0 to 2; and wherein $R^Z$ is H, optionally substituted $C_{1-6}$ alkyl, optionally substituted $C_{3-8}$ cycloalkyl, optionally substituted $C_{6-10}$ aryl, optionally substituted $C_{1-4}$ alkaryl, $C_{2-9}$ heterocyclyl, or optionally substituted $C_{1-4}$ alkheterocyclyl; and wherein the $R^1$ or $R^2$ substituent includes 0 to 6 carbon-carbon double bonds or 0 to 1 carbon-nitrogen double bonds.

Other examples of a compound of formula I include those in which $R^2$ is

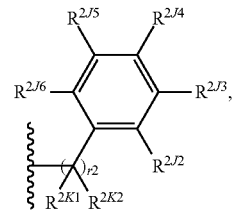

where each $R^{2J2}$, $R^{2J3}$, $R^{2J4}$, $R^{2J5}$, and $R^{2J6}$ is, independently, $C_{1-6}$ alkyl; OH; $C_{1-6}$ alkoxy; SH; $C_{1-6}$ thioalkoxy; Halo; $NO_2$; CN; $CF_3$; $OCF_3$; $NR^{2Ja}R^{2Jb}$, where each of $R^{2Ja}$ and $R^{2Jb}$ is, independently, H or $C_{1-6}$ alkyl; $C(O)R^{2Jc}$, where $R^{2Jc}$ is H or $C_{1-6}$ alkyl; $CO_2R^{2Jd}$, where $R^{2Jd}$ is H or $C_{1-6}$ alkyl; tetrazolyl; $C(O)NR^{2Je}R^{2Jf}$, where each of $R^{2Je}$ and $R^{2Jf}$ is, independently, H or $C_{1-6}$ alkyl; $OC(O)R^{2Jg}$, where $R^{2Jg}$ is $C_{1-6}$ alkyl; $NHC(O)R^{2Jh}$, where $R^{2Jh}$ is H or $C_{1-6}$ alkyl; $SO_3H$; $S(O)_2NR^{2Ji}R^{(x)Jj}$, where each of $R^{2Ji}$ and $R^{2Jj}$ is, independently, H or $C_{1-6}$ alkyl; $S(O)R^{2Jk}$, where $R^{2Jk}$ is $C_{1-6}$ alkyl; and $S(O)_2R^{2Jl}$, where $R^{2Jl}$ is $C_{1-6}$ alkyl, r2 is an integer of 0 to 2, and each of $R^{2K1}$ and $R^{2K2}$ is, independently H or $C_{1-6}$ alkyl.

In one embodiment, $R^{2J4}$ is selected from the group consisting of methoxy, ethoxy, n-propyloxy, isopropyloxy, dimethylamino, diethylamino, thiomethoxy, thioethoxy, n-propyl, isopropyl, and cyclopropyl, preferably where $R^{2J2}$, $R^{2J3}$, $R^{2J5}$, $R^{2J6}$, $R^{2K1}$, and $R^{2K2}$ are H and r2 is 1.

The compounds of the invention may have the formula:

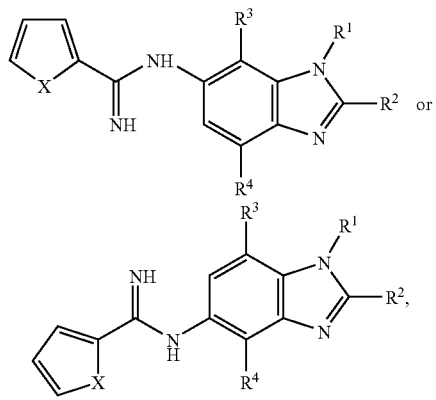

wherein X is O or S.

Examples of a compound of formula I include compounds having the follow structures:

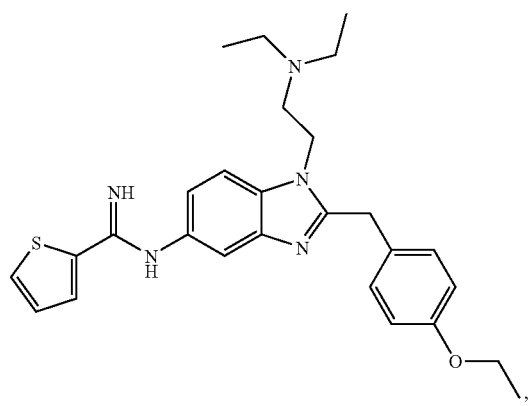
10
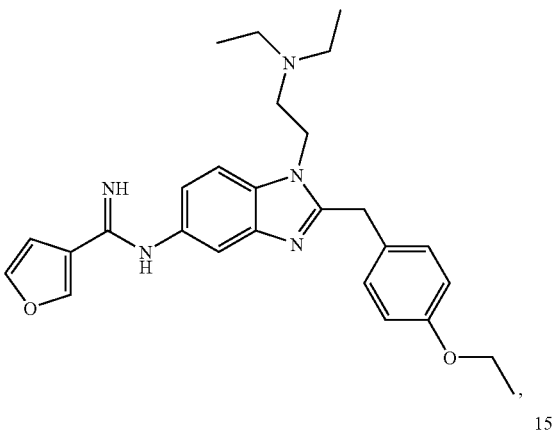
14
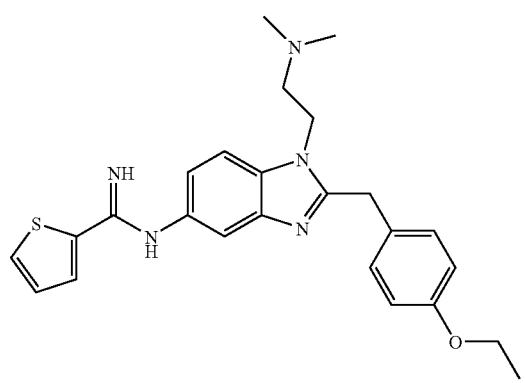
11
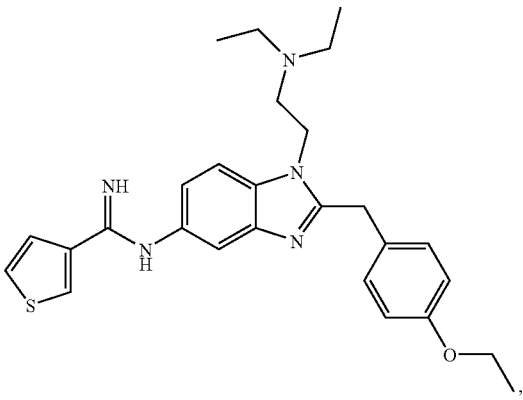
15
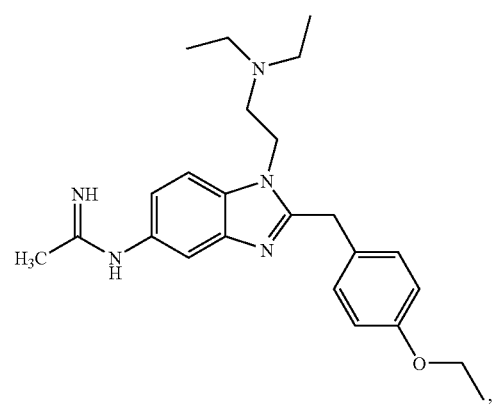
12
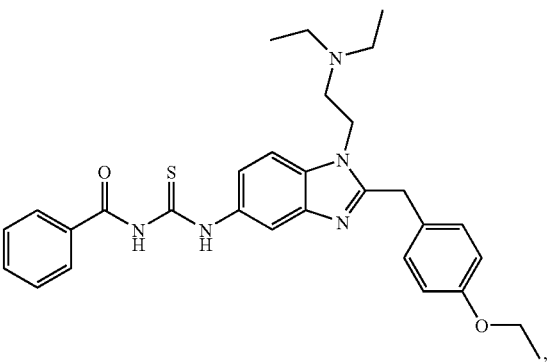
16
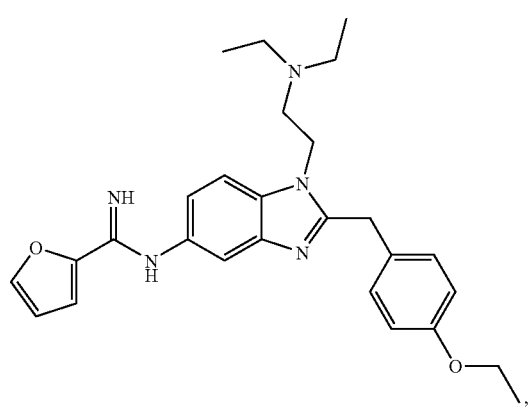
13

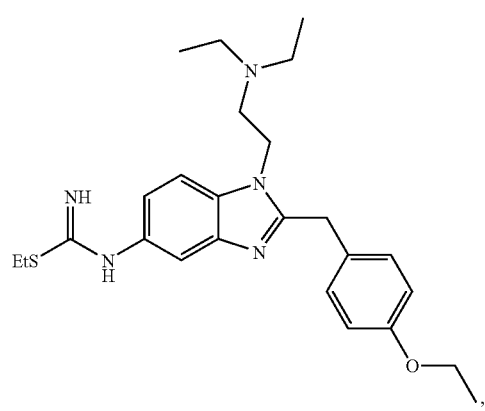
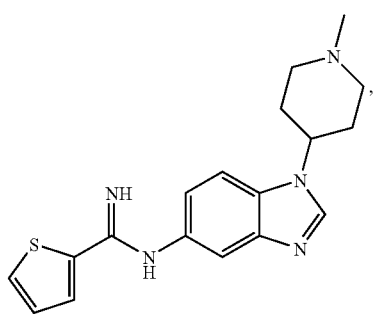
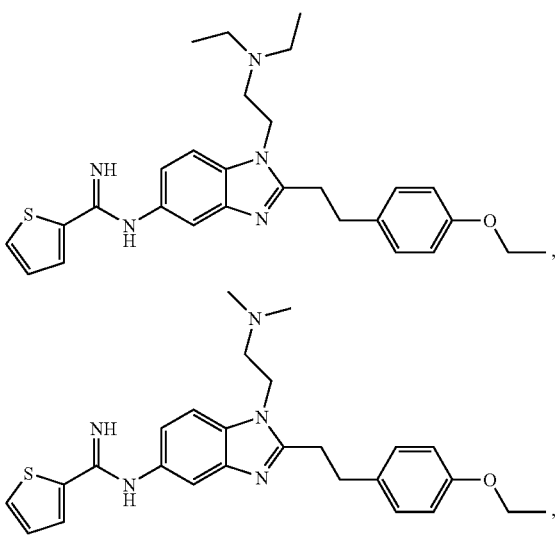
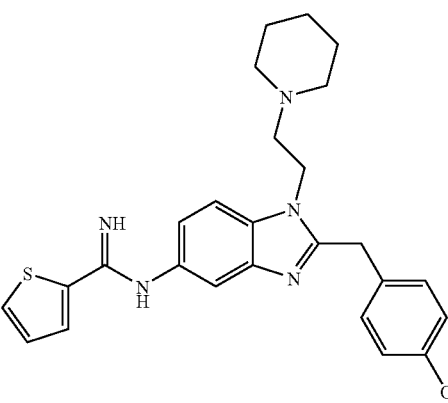
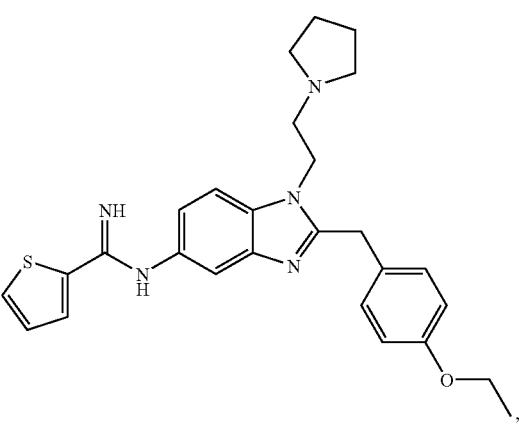

11
-continued
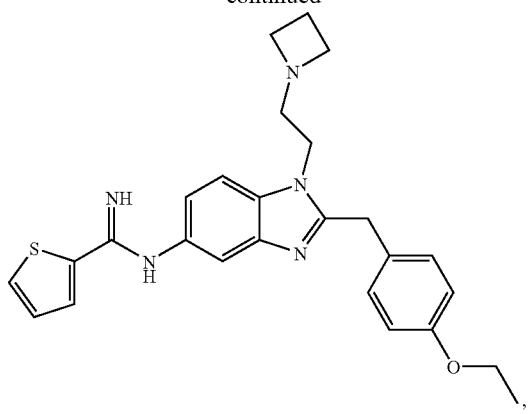
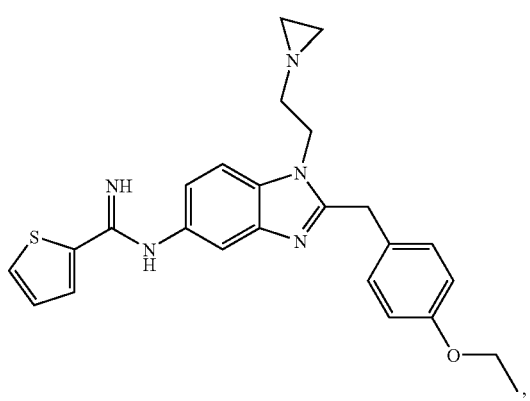
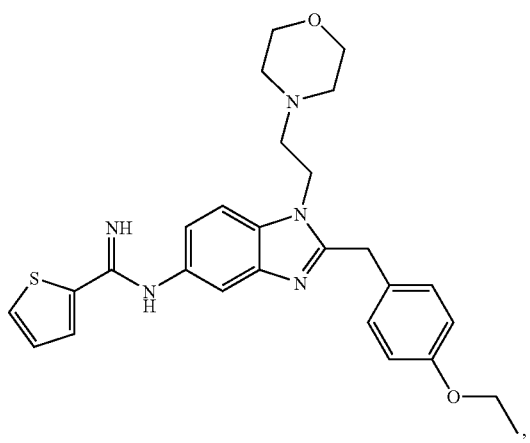
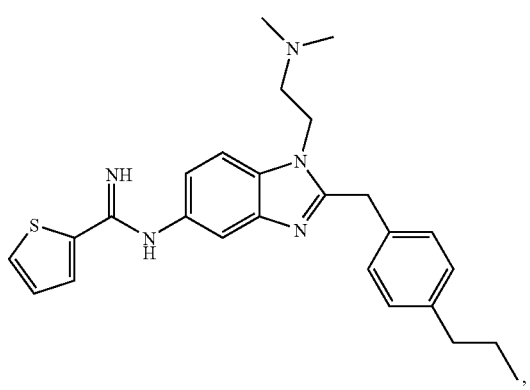
12
-continued
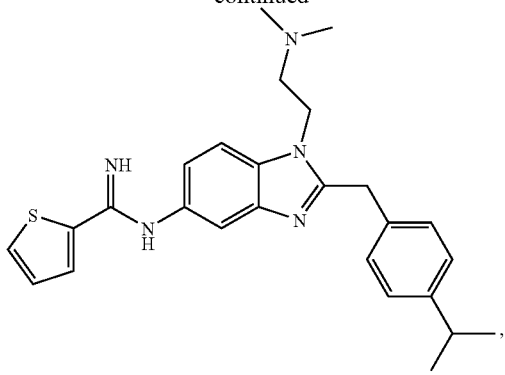
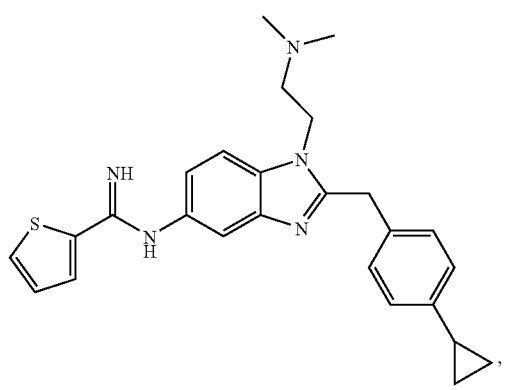
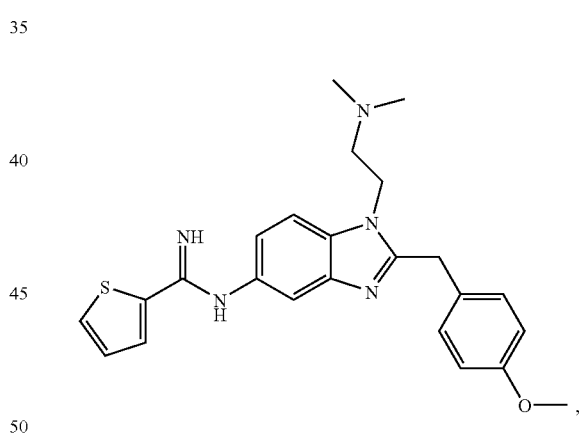
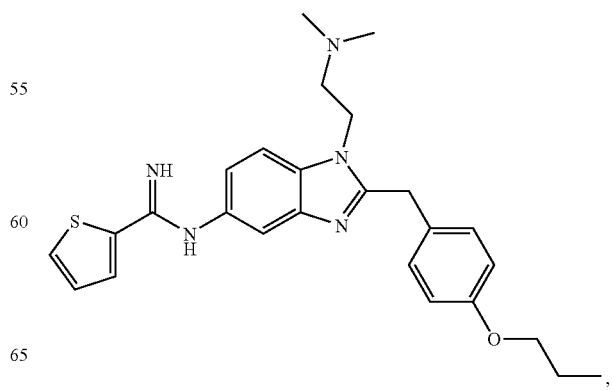

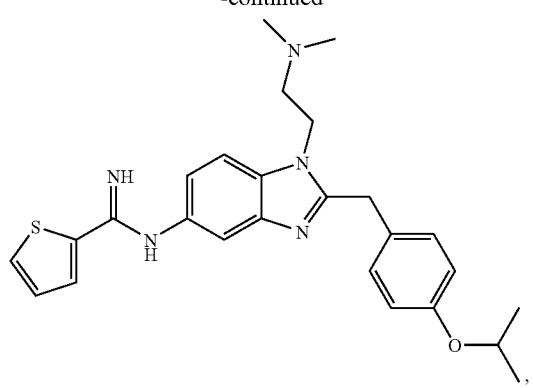
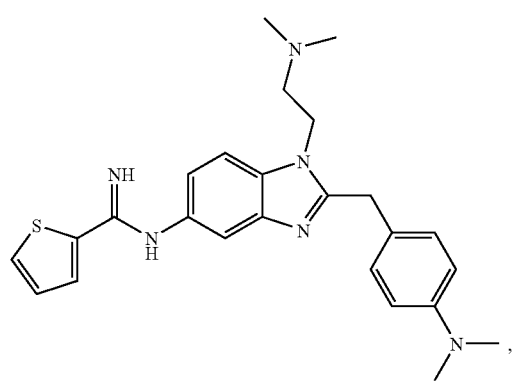
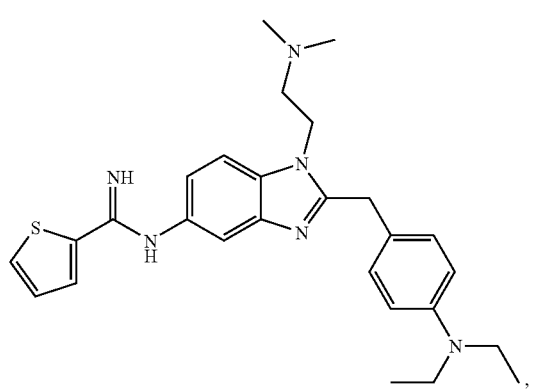
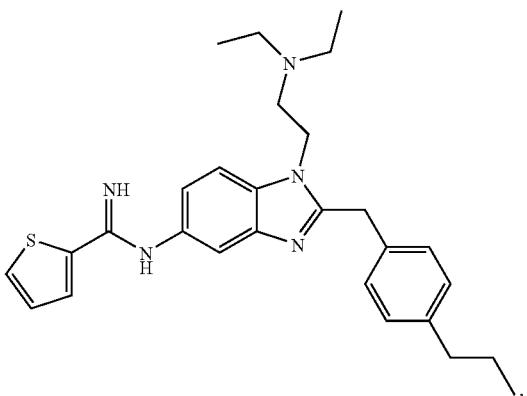
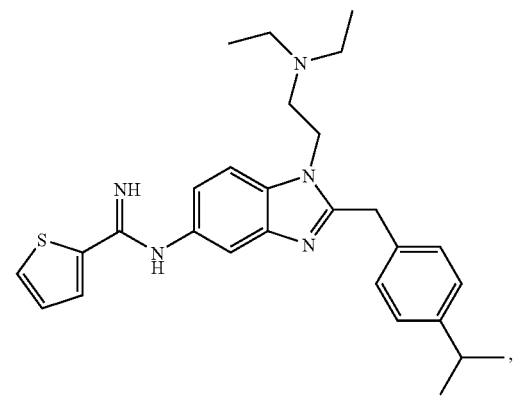
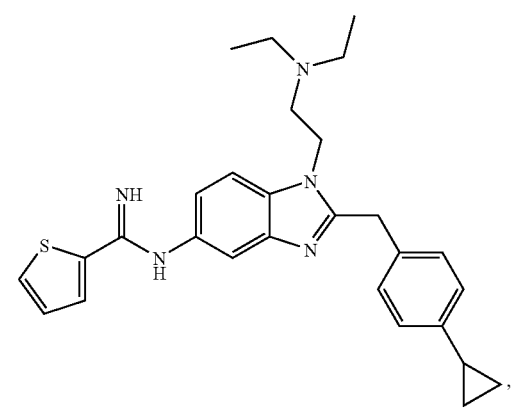

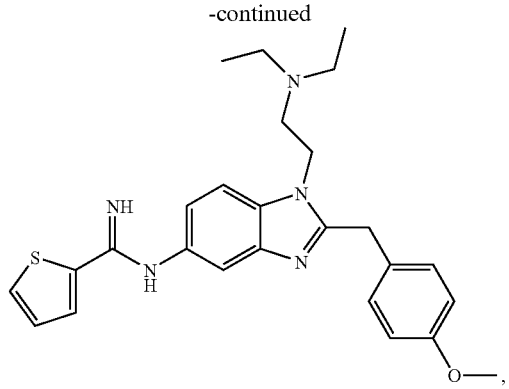
,
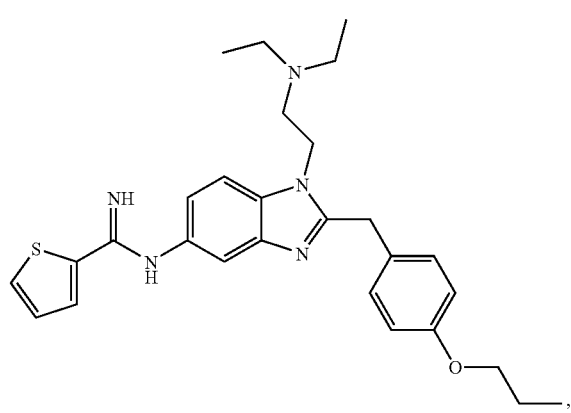
,
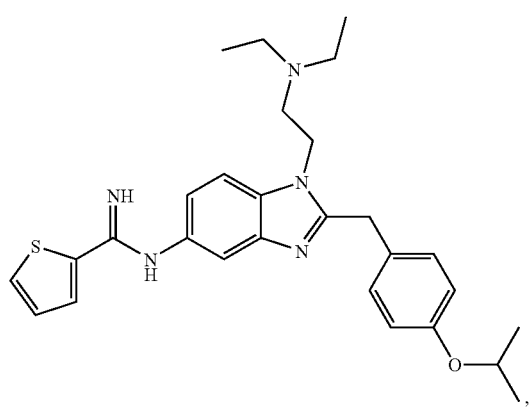
,
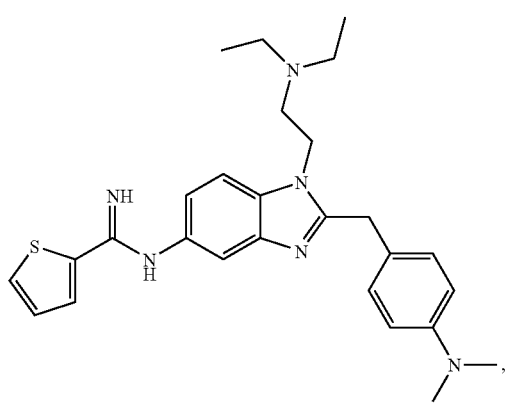
,
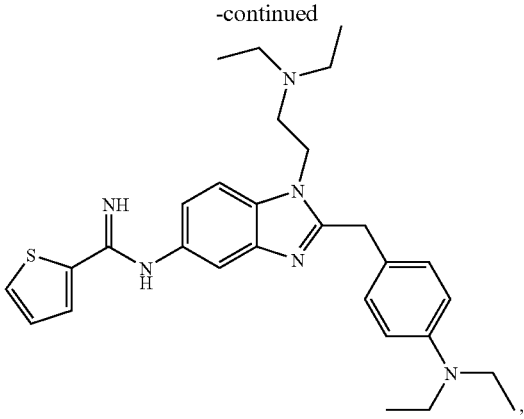
,
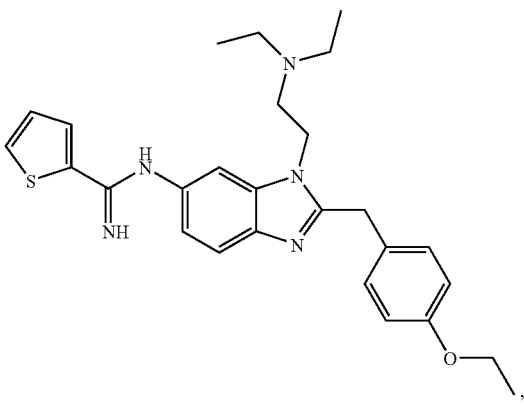
,

-continued

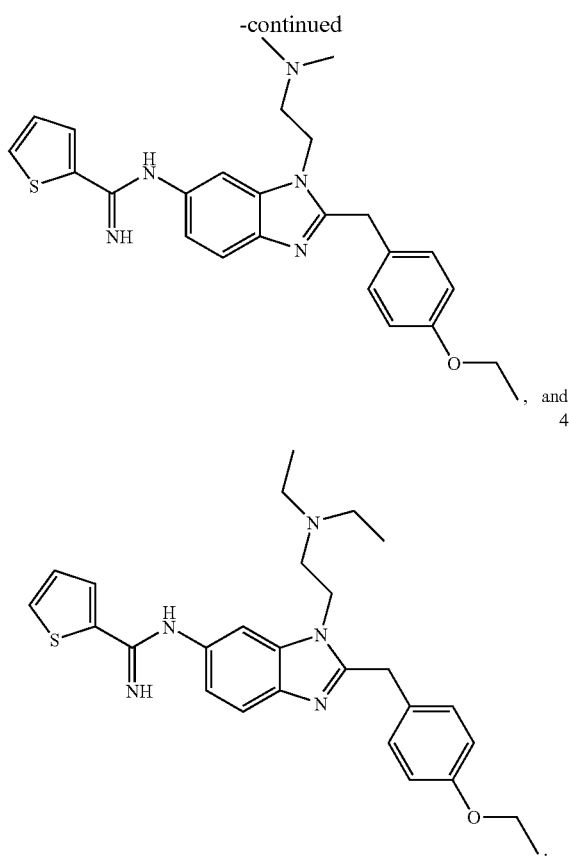

, and

When a compound of the invention posseses one or more asymmetric centers, it may exist as an enantiomeric or diastereomeric mixture, unless otherwise specified. It is to be understood that all such mixtures thereof in any proportion are encompassed within the scope of the present invention. Further, the invention extends to all tautomeric forms of any compound of the invention.

As to any of the above groups that contain one or more substituents, it is understood that such groups do not contain any substitution or substitution patterns which are sterically impractical and/or synthetically non-feasible.

In another embodiment, the compound of formula I selectively inhibits neuronal nitric oxide synthase (nNOS) over endothelial nitric oxide synthase (eNOS) and/or inducible nitric oxide synthase (iNOS) in an in vitro assay. Preferably, the $IC_{50}$ or $K_i$ value observed for the compound when tested is at least 2 times lower in the nNOS assay than in the eNOS and/or iNOS assays. More preferably, the $IC_{50}$ or $K_i$ value is at least 3, 5, or 10 times lower. Most preferably, the $IC_{50}$ or $K_i$ value is 20, or even 50 times lower. In one embodiment, the $IC_{50}$ or $K_i$ value is between 2 times and 50 times lower. $IC_{50}$ values for a compound of the invention can be obtained using the assays described herein, using either the human, murine, or bovine proteins, or by other assays known to those skilled in the art.

In another embodiment, the compound of formula I binds to an opioid receptor. Desirably, the compound is an agonist of the mu opioid receptor, with an $EC_{50}$ value of 10 μM or less in a functional assay, such as, for example, that described herein. Most desirably, the compound has an $EC_{50}$ of 2 μM or less.

In another aspect, the invention features a pharmaceutical composition that includes a compound of the invention and a pharmaceutically acceptable excipient.

In another aspect, the invention features a method for treating or preventing a condition in a mammal, such as, for example, a human, caused by the action of nitric oxide synthase (NOS), and particularly nNOS, that includes administering an effective amount of a compound of the invention to the mammal.

Examples of diseases and other conditions that may benefit from administering a compound or combination of the invention to a subject in need thereof include migraine headache with and without aura or allodynia, neuropathic pain, chronic tension type headache, chronic pain, prevention of the development of chronic pain from acute pain, acute pain (e.g., post-operative pain), acute spinal cord injury, post stroke pain (CPSP), hyperalgesia, diabetic neuropathy, diabetic nephropathy, glaucoma, macular degeneration, an inflammatory disease, including a reversible obstructive airway disease (e.g., asthma or adult respiratory distress syndrome (ARDS)), stroke, reperfusion injury, head trauma, cardiogenic shock, traumatic shock, coronary artery bypass graft (CABG) associated neurological damage, HCA, AIDS associated dementia, neurotoxicity, neurodegeneration, Parkinson's disease, Alzheimer's disease, ALS, Huntington's disease, multiple sclerosis, metamphetamine-induced neurotoxicity, drug addiction, such as, for example, cocaine addiction, morphine/opioid-induced tolerance or opioid-induced hyperalgesia, dependence, or withdrawal, ethanol tolerance, dependence, or withdrawal, epilepsy, anxiety, depression, attention deficit disorder, psychosis, gastrointestinal disorders, and irritable bowel syndrome.

Most desirably, the compound or combination is used to treat or prevent migraine, migraine with associated allodynia, neuropathic pain, acute and chronic pain, stroke, reperfusion injury, neurodegeneration, head trauma, CABG-associated neurological damage, opioid induced tolerance, opioid dependence, hyperalgesia, or opiod induced hyperalgesia (OIH).

In another aspect, the invention features a method of treating or preventing a condition that benefits from the stimulation or antagonism of the mu-opioid receptor.

In another aspect, the invention features a method of treating or preventing a condition causing pain in a mammal, such as, for example, a human, which includes administering an analgesically effective amount of compound of the invention to the mammal.

A compound of the invention can also be used in combination with one or more other therapeutic agents for the prevention or treatment of one of the aforementioned conditions. Examples of classes of therapeutic agents and some specific examples that are useful in combination with a compound of the invention are listed in Table 1.

Other agents useful in combination with a compound of the invention, include antiarrhythmics; DHP-sensitive L-type calcium channel antagonists; omega-conotoxin (Ziconotide)-sensitive N-type calcium channel antagonists; P/Q-type calcium channel antagonists; adenosine kinase antagonists; adenosine receptor $A_1$ agonists; adenosine receptor $A_{2a}$ antagonists; adenosine receptor $A_3$ agonists; adenosine deaminase inhibitors; adenosine nucleoside transport inhibitors; vanilloid VR1 receptor agonists; Substance P/$NK_1$ antagonists; cannabinoid CB1/CB2 agonists; GABA-B antagonists; AMPA and kainate antagonists, metabotropic glutamate receptor antagonists; alpha-2-adrenergic receptor agonists; nicotinic acetylcholine receptor agonists (nAChRs); cholecystokinin B antagonists; sodium channel blockers; a $K_{ATP}$ potassium channel, $K_{v1.4}$ potassium channel, $Ca^{2+}$-activated potassium channel, SK potassium channel, BK potassium channel, IK potassium channel, or KCNQ2/3 potassium channel opening agent (eg. retigabine); $5HT_{1A}$ agonists; muscarinic M3 antagonists, M1 agonists, M2/M3 partial agonist/antagonists; and antioxidants.

TABLE 1

| Agents useful in combination with compounds of the invention | |
| --- | --- |
| Class | Examples |
| Opioid | alfentanil, butorphanol, buprenorphine, codeine, dextromoramide, dextropropoxyphene, dezocine, dihydrocodeine, diphenoxylate, etorphine, fentanyl, hydrocodone, hydromorphone, ketobemidone, levorphanol, levomethadone, methadone, meptazinol, morphine, morphine-6-glucuronide, nalbuphine, naloxone, oxycodone, oxymorphone, pentazocine, pethidine, piritramide, remifentanil, sulfentanyl, tilidine, and tramadol |
| Antidepressant (selective serotonin reuptake inhibitor) | citalopram, escitalopram, fluoxetine, fluvoxamine, paroxetine, or sertraline |
| Antidepressant (norepinephrine-reuptake inhibitor) | amitriptyline, desmethylamitriptyline, clomipramine, doxepin, imipramine, imipramine oxide, trimipramine; adinazolam, amiltriptylinoxide, amoxapine, desipramine, maprotiline, nortriptyline, protriptyline, amineptine, butriptyline, demexiptiline, dibenzepin, dimetacrine, dothiepin, fluacizine, iprindole, lofepramine, melitracen, metapramine, norclolipramine, noxiptilin, opipramol, perlapine, pizotyline, propizepine, quinupramine, reboxetine, or tianeptine |
| Antidepressant (noradrenaline/norepinephrine reuptake inhibitor) | atomoxetine, bupropion, reboxetine, or tomoxetine |
| Antidepressant (dual serotonin/norepinephrine reuptake inhibitor) | duloxetine, milnacipran, mirtazapine, nefazodone, or venlafaxine |
| Antidepressant (monoamine oxidase inhibitor) | amiflamine, iproniazid, isocarboxazid, M-3-PPC (Draxis), moclobemide, pargyline, phenelzine, tranylcypromine, or vanoxerine |
| Antidepressant (reversible monoamine oxidase type A inhibitor) | bazinaprine, befloxatone, brofaromine, cimoxatone, or clorgyline |
| Antidepressant (tricyclic) | amitriptyline, clomipramine, desipramine, doxepin, imipramine, maprotiline, nortryptyline, protriptyline, or trimipramine |
| Antidepressant (other) | adinazolam, alaproclate, amineptine, amitriptyline/chlordiazepoxide combination, atipamezole, azamianserin, bazinaprine, befuraline, bifemelane, binodaline, bipenamol, brofaromine, caroxazone, cericlamine, cianopramine, cimoxatone, citalopram, clemeprol, clovoxamine, dazepinil, deanol, demexiptiline, dibenzepin, dothiepin, droxidopa, enefexine, estazolam, etoperidone, femoxetine, fengabine, fezolamine, fluotracen, idazoxan, indalpine, indeloxazine, iprindole, levoprotiline, lithium, litoxetine; lofepramine, medifoxamine, metapramine, metralindole, mianserin, milnacipran, minaprine, mirtazapine, montirelin, nebracetam, nefopam, nialamide, nomifensine, norfluoxetine, orotirelin, oxaflozane, pinazepam, pirlindone, pizotyline, ritanserin, rolipram, sercloremine, setiptiline, sibutramine, sulbutiamine, sulpiride, teniloxazine, thozalinone, thymoliberin, tianeptine, tiflucarbine, trazodone, tofenacin, tofisopam, toloxatone, tomoxetine, veralipride, viloxazine, viqualine, zimelidine, zometapine |
| Antiepileptic | carbamazepine, flupirtine, gabapentin, lamotrigine, oxcarbazepine, phenyloin, retigabine, topiramate, or valproate |
| Non-steroidal anti-inflammatory drug (NSAID) | acemetacin, aspirin, celecoxib, deracoxib, diclofenac, diflunisal, ethenzamide, etofenamate, etoricoxib, fenoprofen, flufenamic acid, flurbiprofen, lonazolac, lornoxicam, ibuprofen, indomethacin, isoxicam, kebuzone, ketoprofen, ketorolac, naproxen, nabumetone, niflumic acid, sulindac, tolmetin, piroxicam, meclofenamic acid, mefenamic acid, meloxicam, metamizol, mofebutazone, oxyphenbutazone, parecoxib, phenidine, phenylbutazone, piroxicam, propacetamol, propyphenazone, rofecoxib, salicylamide, suprofen, tiaprofenic acid, tenoxicam, valdecoxib, 4-(4-cyclohexyl-2-methyloxazol-5-yl)-2-fluorobenzenesulfonamide, N-[2-(cyclohexyloxy)-4-nitrophenyl]methanesulfonamide, 2-(3,4-difluorophenyl)-4-(3-hydroxy-3-methylbutoxy)-5-[4-(methylsulfonyl)phenyl]-3(2H)-pyridazinone, or 2-(3,5-difluorophenyl)-3-[4-(methylsulfonyl)phenyl]-2-cyclopenten-1-one). |
| $5HT_{1B/1D}$ agonist | eletriptan, frovatriptan, naratriptan, rizatriptan, sumatriptan, or zolmitriptan |

TABLE 1-continued

Agents useful in combination with compounds of the invention

| Class | Examples |
|---|---|
| Anti-inflammatory compounds | aspirin, celecoxib, cortisone, deracoxib, diflunisal, etoricoxib, fenoprofen, ibuprofen, ketoprofen, naproxen, prednisolone, sulindac, tolmetin, piroxicam, mefenamic acid, meloxicam, phenylbutazone, rofecoxib, suprofen, valdecoxib, 4-(4-cyclohexyl-2-methyloxazol-5-yl)-2-fluorobenzenesulfonamide, N-[2-(cyclohexyloxy)-4-nitrophenyl]methanesulfonamide, 2-(3,4-difluorophenyl)-4-(3-hydroxy-3-methylbutoxy)-5-[4-(methylsulfonyl)phenyl]-3(2H)-pyridazinone, or 2-(3,5-difluorophenyl)-3-[4-(methylsulfonyl)phenyl]-2-cyclopenten-1-one |
| N-methyl-D-aspartate antagonist | amantadine; aptiganel; besonprodil; budipine; conantokin G; delucemine; dexanabinol; dextromethorphan; dextropropoxyphen; felbamate; fluorofelbamate; gacyclidine; glycine; ipenoxazone; kaitocephalin; ketamine; ketobemidone; lanicemine; licostinel; midafotel; memantine; D-methadone; D-morphine; milnacipran; neramexane; orphenadrine; remacemide; sulfazocine; FPL-12,495 (racemide metabolite); topiramate; (αR)-α-amino-5-chloro-1-(phosphonomethyl)-1H-benzimidazole-2-propanoic acid; 1-aminocyclopentane-carboxylic acid; [5-(aminomethyl)-2-[[[(5S)-9-chloro-2,3,6,7-tetrahydro-2,3-dioxo-1H-,5H-pyrido[1,2,3-de]quinoxalin-5-yl]acetyl]amino]phenoxy]-acetic acid; α-amino-2-(2-phosphonoethyl)-cyclohexanepropanoic acid; α-amino-4-(phosphonomethyl)-benzeneacetic acid; (3E)-2-amino-4-(phosphonomethyl)-3-heptenoic acid; 3-[(1E)-2-carboxy-2-phenylethenyl]-4,6-dichloro-1H-indole-2-carboxylic acid; 8-chloro-2,3-dihydropyridazino[4,5-b]quinoline-1,4-dione 5-oxide salt with 2-hydroxy-N,N,N-trimethyl-ethanaminium; N'-[2-chloro-5-(methylthio)phenyl]-N-methyl-N-[3-(methylthio)phenyl]-guanidine; N'-[2-chloro-5-(methylthio)phenyl]-N-methyl-N-[3-[(R)-methylsulfinyl]phenyl]-guanidine; 6-chloro-2,3,4,9-tetrahydro-9-methyl-2,3-dioxo-1H-indeno[1,2-b]pyrazine-9-acetic acid; 7-chlorothiokynurenic acid; (3S,4aR,6S,8aR)-decahydro-6-(phosphonomethyl)-3-isoquinolinecarboxylic acid; (−)-6,7-dichloro-1,4-dihydro-5-[3-(methoxymethyl)-5-(3-pyridinyl)-4-H-1,2,4-triazol-4-yl]-2,3-quinoxalinedione; 4,6-dichloro-3-[(E)-(2-oxo-1-phenyl-3-pyrrolidinylidene)methyl]-1H-indole-2-carboxylic acid; (2R,4S)-rel-5,7-dichloro-1,2,3,4-tetrahydro-4-[[(phenylamino)carbonyl]amino]-2-quinolinecarboxylic acid; (3R,4S)-rel-3,4-dihydro-3-[4-hydroxy-4-(phenylmethyl)-1-piperidinyl-]-2H-1-benzopyran-4,7-diol; 2-[(2,3-dihydro-1H-inden-2-yl)amino]-acetamide; 1,4-dihydro-6-methyl-5-[(methylamino)methyl]-7-nitro-2,3-quinoxalinedione; [2-(8,9-dioxo-2,6-diazabicyclo[5.2.0]non-1(7)-en-2-yl)ethyl]-phosphonic acid; (2R,6S)-1,2,3,4,5,6-hexahydro-3-[(2S)-2-methoxypropyl]-6,11,11-trimethyl-2,6-methano-3-benzazocin-9-ol; 2-hydroxy-5-[[(pentafluorophenyl)methyl]amino]-benzoic acid; 1-[2-(4-hydroxyphenoxy)ethyl]-4-[(4-methylphenyl)methyl]-4-piperidinol; 1-[4-(1H-imidazol-4-yl)-3-butynyl]-4-(phenylmethyl)-piperidine; 2-methyl-6-(phenylethynyl)-pyridine; 3-(phosphonomethyl)-L-phenylalanine; or 3,6,7-tetrahydro-2,3-dioxo-N-phenyl-1H,5H-pyrido[1,2,3-de]quinoxaline-5-acetamide |

Asymmetric or chiral centers may exist in any of the compounds of the present invention. The present invention contemplates the various stereoisomers and mixtures thereof. Individual stereoisomers of compounds of the present invention are prepared synthetically from commercially available starting materials that contain asymmetric or chiral centers, or by preparation of mixtures of enantiometic compounds followed by resolution. These synthetic methods are well-known to those of ordinary skill in the art. These methods of resolution are exemplified by (1) attachment of a racemic mixture of enantiomers, designated (+/−), to a chiral auxiliary, separation of the resulting diastereomers by recrystallization or chromatography and liberation of the optically pure product from the auxiliary or (2) direct separation of the mixture of optical enantiomers on chiral chromatographic columns. Enantiomers are designated herein by the symbols "R," or "S," depending on the configuration of substituents around the chiral carbon atom. Alternatively, enantiomers are designated as (+) or (−) depending on whether a solution of the enantiomer rotates the plane of polarized light clockwise or counterclockwise, respectively.

Geometric isomers may also exist in the compounds of the present invention. The present invention contemplates the various geometric isomers and mixtures thereof resulting from the arrangement of substituents around a carbon-carbon double bond and designates such isomers as of the Z or E configuration, where the term "Z" represents substituents on the same side of the carbon-carbon double bond and the term "E" represents substituents on opposite sides of the carbon-carbon double bond. It is also recognized that for structures in which tautomeric forms are possible, the description of one tautomeric form is equivalent to the description of both, unless otherwise specified. For example, amidine structures of the formula —C(=NR$^Q$)NHR$^T$ and —C(NHR$^Q$)=NR$^T$, where R$^T$ and R$^Q$ are different, are equivalent tautomeric structures and the description of one inherently includes the other.

It is understood that substituents and substitution patterns on the compounds of the invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results.

Other features and advantages of the present invention will become apparent from the following detailed description. It should be understood that the detailed description and the specific examples, while indicating preferred embodiments of the invention, are given by way of illustration only, and various changes and modifications within the spirit and scope of the invention will become apparent to those skilled in the art from this detailed description.

DEFINITIONS

The terms "acyl" or "alkanoyl," as used interchangeably herein, represent an alkyl group, as defined herein, or hydrogen attached to the parent molecular group through a carbonyl group, as defined herein, and is exemplified by formyl, acetyl, propionyl, butanoyl and the like. Exemplary unsubstituted acyl groups include from 2 to 7 carbons.

The term "agonist" or "functional agonist at the mu opioid receptor" refers to a substance, for example a compound of the invention that binds to the receptor and causes a response or stimuli, such as, for example, the production cAMP (cyclic AMP), or the binding of GTP-γs. Binding to the receptor can be expressed in terms of an $IC_{50}$ value or a $K_i$ value and functional agonist or functional activity can be expressed as an $EC_{50}$. Preferably the $K_i$ is less than 1 μM, most preferably the $K_i$ is less than 0.1 μM. The term "partial agonist" means a substance that binds to a receptor and produces a sub-maximal biological response. As used herein, "full response" is from 75% to 100% of a biological system's maximal response, with "sub-maximal" being a measurable response that is less than a full response. As well as producing a sub-maximal response, a partial agonist may, in high enough concentrations, antagonize an agonist or natural ligand by only partially activating a given receptor.

The term "antagonist" means a substance that does not elicit a biological response for a receptor and that also interferes with receptor activation.

The terms "$C_{x-y}$ alkaryl" or "$C_{x-y}$ alkylenearyl," as used herein, represent a chemical substituent of formula -RR', where R is an alkylene group of x to y carbons and R' is an aryl group as defined elsewhere herein. Similarly, by the terms "$C_{x-y}$ alkheteroaryl" "$C_{x-y}$ alkyleneheteroaryl," is meant a chemical substituent of formula -RR", where R is an alkylene group of x to y carbons and R" is a heteroaryl group as defined elsewhere herein. Other groups preceded by the prefix "alk-" or "alkylene-" are defined in the same manner. Exemplary unsubstituted alkaryl groups are of from 7 to 16 carbons.

The term "alkcycloalkyl" represents a cycloalkyl group attached to the parent molecular group through an alkylene group.

The term "alkenyl," as used herein, represents monovalent straight or branched chain groups of, unless otherwise specified, from 2 to 6 carbons containing one or more carbon-carbon double bonds and is exemplified by ethenyl, 1-propenyl, 2-propenyl, 2-methyl-1-propenyl, 1-butenyl, 2-butenyl, and the like.

The term "alkheterocyclyl" represents a heterocyclic group attached to the parent molecular group through an alkylene group. Exemplary unsubstituted alkheterocyclyl groups are of from 3 to 14 carbons.

The term "alkoxy" represents a chemical substituent of formula —OR, where R is an alkyl group of 1 to 6 carbons, unless otherwise specified.

The term "alkoxyalkyl" represents an alkyl group substituted with an alkoxy group. Exemplary unsubstituted alkoxyalkyl groups include between 2 to 12 carbons.

The terms "alkyl" and the prefix "alk-," as used herein, are inclusive of both straight chain and branched chain saturated groups of from 1 to 6 carbons, unless otherwise specified. Alkyl groups are exemplified by methyl, ethyl, n- and iso-propyl, n-, sec-, iso- and tert-butyl, neopentyl, and the like, and may be optionally substituted with one, two, three or, in the case of alkyl groups of two carbons or more, four substituents independently selected from the group consisting of: (1) alkoxy of one to six carbon atoms; (2) alkylsulfinyl of one to six carbon atoms; (3) alkylsulfonyl of one to six carbon atoms; (4) amino; (5) aryl; (6) arylalkoxy; (7) aryloyl; (8) azido; (9) carboxaldehyde; (10) cycloalkyl of three to eight carbon atoms; (11) halo; (12) heterocyclyl; (13) (heterocycle)oxy; (14) (heterocycle)oyl; (15) hydroxyl; (16) N-protected amino; (17) nitro; (18) oxo; (19) spiroalkyl of three to eight carbon atoms; (20) thioalkoxy of one to six carbon atoms; (21) arylthioalkoxy; (22) thiol; (23) —$CO_2R^A$, where $R^A$ is selected from the group consisting of (a) alkyl, (b) aryl and (c) alkaryl, where the alkylene group is of one to six carbon atoms; (24) —$C(O)NR^BR^C$, where each of $R^B$ and $R^C$ is, independently, selected from the group consisting of (a) hydrogen, (b) alkyl, (c) aryl and (d) alkaryl, where the alkylene group is of one to six carbon atoms; (25) —$SO_2R^D$, where $R^D$ is selected from the group consisting of (a) alkyl, (b) aryl and (c) alkaryl, where the alkylene group is of one to six carbon atoms; (26) —$SO_2NR^ER^F$, where each of $R^E$ and $R^F$ is, independently, selected from the group consisting of (a) hydrogen, (b) alkyl, (c) aryl and (d) alkaryl, where the alkylene group is of one to six carbon atoms; and (27) —$NR^GR^H$, where each of $R^G$ and $R^H$ is, independently, selected from the group consisting of (a) hydrogen; (b) an N-protecting group; (c) alkyl of one to six carbon atoms; (d) alkenyl of two to six carbon atoms; (e) alkynyl of two to six carbon atoms; (f) aryl; (g) alkaryl, where the alkylene group is of one to six carbon atoms; (h) cycloalkyl of three to eight carbon atoms; and (i) alkcycloalkyl, where the cycloalkyl group is of three to eight carbon atoms, and the alkylene group is of one to ten carbon atoms, with the proviso that no two groups are bound to the nitrogen atom through a carbonyl group or a sulfonyl group.

The term "alkylamino" represents —$NR^GR^H$, where each of $R^G$ and $R^H$ is, independently, selected a hydrogen or an alkyl group of from 1 to 6 carbons.

The term "alkylene," as used herein, represents a saturated divalent hydrocarbon group derived from a straight or branched chain saturated hydrocarbon by the removal of two hydrogen atoms, and is exemplified by methylene, ethylene, isopropylene and the like.

The term "alkylsulfinyl," as used herein, represents an alkyl group attached to the parent molecular group through an —S(O)— group. Exemplary unsubstituted alkylsulfinyl groups are of from 1 to 6 carbons.

The term "alkylsulfonyl," as used herein, represents an alkyl group attached to the parent molecular group through an —$SO_2$— group. Exemplary unsubstituted alkylsulfonyl groups are of from 1 to 6 carbons.

The term "alkylsulfinylalkyl," as used herein, represents an alkyl group, as defined herein, substituted by an alkylsulfinyl group. Exemplary unsubstituted alkylsulfinylalkyl groups are of from 2 to 12 carbons.

The term "alkylsulfonylalkyl," as used herein, represents an alkyl group, as defined herein, substituted by an alkylsulfonyl group. Exemplary unsubstituted alkylsulfonylalkyl groups are of from 2 to 12 carbons.

The term "alkynyl," as used herein, represents monovalent straight or branched chain groups of from two to six carbon atoms containing a carbon-carbon triple bond and is exemplified by ethynyl, 1-propynyl, and the like.

The term "amidine," as used herein, represents a —C(=NH)NH$_2$ group.

The term "amino," as used herein, represents an —NH$_2$ group.

The term "aminoalkyl," as used herein, represents an alkyl group, as defined herein, substituted by an amino group.

The term "and/or" as used herein is meant to encompass alternative or inclusive combinations. For example, the statement "group A, group B, and/or group C" encompasses seven possibilities; each of the individual groups (3 possibilities), all of the groups together (1 possibility), and any two of the groups together (3 possibilities).

The term "aryl," as used herein, represents a mono- or bicyclic carbocyclic ring system having one or two aromatic rings and is exemplified by phenyl, naphthyl, 1,2-dihydronaphthyl, 1,2,3,4-tetrahydronaphthyl, fluorenyl, indanyl, indenyl, and the like, and may be optionally substituted with one, two, three, four, or five substituents independently selected from the group consisting of: (1) alkanoyl of one to six carbon atoms; (2) alkyl of one to six carbon atoms; (3) alkoxy of one to six carbon atoms; (4) alkoxyalkyl, where the alkyl and alkylene groups are independently of one to six carbon atoms; (5) alkylsulfinyl of one to six carbon atoms; (6) alkylsulfinylalkyl, where the alkyl and alkylene groups are independently of one to six carbon atoms; (7) alkylsulfonyl of one to six carbon atoms; (8) alkylsulfonylalkyl, where the alkyl and alkylene groups are independently of one to six carbon atoms; (9) aryl; (10) amino; (11) aminoalkyl of one to six carbon atoms; (12) heteroaryl; (13) alkaryl, where the alkylene group is of one to six carbon atoms; (14) aryloyl; (15) azido; (16) azidoalkyl of one to six carbon atoms; (17) carboxaldehyde; (18) (carboxaldehyde)alkyl, where the alkylene group is of one to six carbon atoms; (19) cycloalkyl of three to eight carbon atoms; (20) alkcycloalkyl, where the cycloalkyl group is of three to eight carbon atoms and the alkylene group is of one to ten carbon atoms; (21) halo; (22) haloalkyl of one to six carbon atoms; (23) heterocyclyl; (24) (heterocyclyl)oxy; (25) (heterocyclyl)oyl; (26) hydroxy; (27) hydroxyalkyl of one to six carbon atoms; (28) nitro; (29) nitroalkyl of one to six carbon atoms; (30) N-protected amino; (31) N-protected aminoalkyl, where the alkylene group is of one to six carbon atoms; (32) oxo; (33) thioalkoxy of one to six carbon atoms; (34) thioalkoxyalkyl, where the alkyl and alkylene groups are independently of one to six carbon atoms; (35) —(CH$_2$)$_q$CO$_2$R$^A$, where q is an integer of from zero to four, and R$^A$ is selected from the group consisting of (a) alkyl, (b) aryl, and (c) alkaryl, where the alkylene group is of one to six carbon atoms; (36) —(CH$_2$)$_q$CONR$^B$R$^C$, where q is an integer of from zero to four and where R$^B$ and R$^C$ are independently selected from the group consisting of (a) hydrogen, (b) alkyl, (c) aryl, and (d) alkaryl, where the alkylene group is of one to six carbon atoms; (37) —(CH$_2$)$_q$SO$_2$R$^D$, where q is an integer of from zero to four and where R$^D$ is selected from the group consisting of (a) alkyl, (b) aryl, and (c) alkaryl, where the alkylene group is of one to six carbon atoms; (38) —(CH$_2$)$_q$SO$_2$NR$^E$R$^F$, where q is an integer of from zero to four and where each of R$^E$ and R$^F$ is, independently, selected from the group consisting of (a) hydrogen, (b) alkyl, (c) aryl, and (d) alkaryl, where the alkylene group is of one to six carbon atoms; (39) —(CH$_2$)$_q$NR$^G$R$^H$, where q is an integer of from zero to four and where each of R$^G$ and R$^H$ is, independently, selected from the group consisting of (a) hydrogen; (b) an N-protecting group; (c) alkyl of one to six carbon atoms; (d) alkenyl of two to six carbon atoms; (e) alkynyl of two to six carbon atoms; (f) aryl; (g) alkaryl, where the alkylene group is of one to six carbon atoms; (h) cycloalkyl of three to eight carbon atoms; and (i) alkcycloalkyl, where the cycloalkyl group is of three to eight carbon atoms, and the alkylene group is of one to ten carbon atoms, with the proviso that no two groups are bound to the nitrogen atom through a carbonyl group or a sulfonyl group; (40) thiol; (41) perfluoroalkyl; (42) perfluoroalkoxy; (43) aryloxy; (44) cycloalkoxy; (45) cycloalkylalkoxy; and (46) arylalkoxy.

The term "arylalkoxy," as used herein, represents an alkaryl group attached to the parent molecular group through an oxygen atom. Exemplary unsubstituted arylalkoxy groups are of from 7 to 16 carbons.

The term "aryloxy" represents a chemical substituent of formula —OR', where R' is an aryl group of 6 to 18 carbons, unless otherwise specified.

The terms "aryloyl" and "aroyl" as used interchangeably herein, represent an aryl group that is attached to the parent molecular group through a carbonyl group. Exemplary unsubstituted aryloyl groups are of 7 or 11 carbons.

The term "azido" represents an N$_3$ group, which can also be represented as N=N=N.

The term "azidoalkyl" represents an azido group attached to the parent molecular group through an alkyl group.

The term "bridged heterocyclyl" represents a heterocyclic compound, as otherwise described herein, having a bridged multicyclic structure in which one or more carbon atoms and/or heteroatoms bridges two non-adjacent members of a monocyclic ring. An exemplary bridged heterocyclyl group is a quinuclidinyl group.

The term "bridged alkheterocyclyl" represents a bridged heterocyclic compound, as otherwise described herein, attached to the parent molecular group through an alkylene group.

The term "carbonyl," as used herein, represents a C(O) group, which can also be represented as C=O.

The term "carboxaldehyde" represents a CHO group.

The term "carboxaldehydealkyl" represents a carboxaldehyde group attached to the parent molecular group through an alkylene group.

The term "cycloalkyl," as used herein represents a monovalent saturated or unsaturated non-aromatic cyclic hydrocarbon group of from three to eight carbons, unless otherwise specified, and is exemplified by cyclopropyl, cyclobutyl, cyclopentyl, cyclohexyl, cycloheptyl, bicyclo[2.2.1.]heptyl and the like. The cycloalkyl groups of this invention can be optionally substituted with (1) alkanoyl of one to six carbon atoms; (2) alkyl of one to six carbon atoms; (3) alkoxy of one to six carbon atoms; (4) alkoxyalkyl, where the alkyl and alkylene groups are independently of one to six carbon atoms; (5) alkylsulfinyl of one to six carbon atoms; (6) alkylsulfinylalkyl, where the alkyl and alkylene groups are independently of one to six carbon atoms; (7) alkylsulfonyl of one to six carbon atoms; (8) alkylsulfonylalkyl, where the alkyl and alkylene groups are independently of one to six carbon atoms; (9) aryl; (10) amino; (11) aminoalkyl of one to six carbon atoms; (12) heteroaryl; (13) alkaryl, where the alkylene group is of one to six carbon atoms; (14) aryloyl; (15) azido; (16) azidoalkyl of one to six carbon atoms; (17) carboxaldehyde; (18) (carboxaldehyde)alkyl, where the alkylene group is of one to six carbon atoms; (19) cycloalkyl of three to eight carbon atoms; (20) alkcycloalkyl, where the cycloalkyl group is of three to eight carbon atoms and the alkylene group is of one to ten carbon atoms; (21) halo; (22) haloalkyl of one to six carbon atoms; (23) heterocyclyl; (24) (heterocyclyl)oxy; (25) (heterocyclyl)oyl; (26) hydroxy; (27) hydroxyalkyl of one to six carbon atoms; (28) nitro; (29) nitroalkyl of one to six carbon atoms; (30) N-protected amino; (31) N-protected aminoalkyl, where the alkylene group is of one to six carbon atoms; (32) oxo; (33) thioalkoxy of one to six carbon atoms; (34) thioalkoxyalkyl, where the alkyl and alkylene groups are independently of one to six carbon atoms; (35) —(CH$_2$)$_q$CO$_2$R$^A$, where q is an integer of from zero to four, and R$^A$ is selected from the group consisting of (a) alkyl, (b) aryl, and (c) alkaryl, where the alkylene group is of one to six carbon atoms; (36) —(CH$_2$)$_q$CONR$^B$R$^C$, where q is an integer of from zero to four and where R$^B$ and R$^C$ are independently selected from the group consisting of (a) hydrogen, (b) alkyl, (c) aryl, and (d) alkaryl, where the alkylene group is of one to six carbon atoms; (37) —(CH$_2$)$_q$SO$_2$R$^D$, where q is an integer of from zero to four and where R$^D$ is selected from the group consisting of (a) alkyl, (b) aryl, and (c) alkaryl, where the alkylene group is of one to six carbon atoms; (38) —(CH$_2$)$_q$SO$_2$NR$^E$R$^F$, where q is an integer of from zero to four and where each of R$^E$ and R$^F$ is, independently, selected from the group consisting of (a) hydrogen, (b) alkyl, (c) aryl, and (d) alkaryl, where the alkylene group is of one to six carbon atoms; (39) —(CH$_2$)$_q$NR$^G$R$^H$, where q is an integer of from zero to four and where each of R$^G$ and R$^H$ is, independently, selected from the group consisting of (a) hydrogen; (b) an N-protecting group; (c) alkyl of one to six carbon atoms; (d) alkenyl of two to six carbon atoms; (e) alkynyl of two to six carbon atoms; (f) aryl; (g) alkaryl, where the alkylene group is of one to six carbon atoms; (h) cycloalkyl of three to eight carbon atoms; and (i) alkcycloalkyl, where the cycloalkyl group is of three to eight carbon atoms, and the alkylene group is of one to ten carbon atoms, with the proviso that no two groups are bound to the nitrogen atom through a carbonyl group or a sulfonyl group; (40) thiol; (41) perfluoroalkyl; (42) perfluoroalkoxy; (43) aryloxy; (44) cycloalkoxy; (45) cycloalkylalkoxy; and (46) arylalkoxy.

The terms "cycloalkyloxy" or "cycloalkoxy", as used interchangeably herein, represent a cycloalkyl group, as defined herein, attached to the parent molecular group through an oxygen atom. Exemplary unsubstituted cycloalkyloxy groups are of from 3 to 8 carbons.

The term an "effective amount" or a "sufficient amount" of an agent, as used herein, is that amount sufficient to effect beneficial or desired results, such as clinical results, and, as such, an "effective amount" depends upon the context in which it is being applied. For example, in the context of administering an agent that is an inhibitor of NOS, an effective amount of an agent is, for example, an amount sufficient to achieve a reduction in NOS activity as compared to the response obtained without administration of the agent.

The terms "halide" or "halogen" or "halo" or "Hal," as used herein, represent bromine, chlorine, iodine, or fluorine.

The term "heteroaryl," as used herein, represents that subset of heterocycles, as defined herein, which are aromatic: i.e., they contain 4n+2 pi electrons within the mono- or multicyclic ring system. Exemplary unsubstituted heteroaryl groups are of from 1 to 9 carbons.

The terms "heterocycle" or "heterocyclyl," as used interchangeably herein represent a 5-, 6- or 7-membered ring, unless otherwise specified, containing one, two, three, or four heteroatoms independently selected from the group consisting of nitrogen, oxygen and sulfur. The 5-membered ring has zero to two double bonds and the 6- and 7-membered rings have zero to three double bonds. The term "heterocycle" also includes bicyclic, tricyclic and tetracyclic groups in which any of the above heterocyclic rings is fused to one, two, or three rings independently selected from the group consisting of an aryl ring, a cyclohexane ring, a cyclohexene ring, a cyclopentane ring, a cyclopentene ring and another monocyclic heterocyclic ring, such as indolyl, quinolyl, isoquinolyl, tetrahydroquinolyl, benzofuryl, benzothienyl and the like. Heterocyclics include pyrrolyl, pyrrolinyl, pyrrolidinyl, pyrazolyl, pyrazolinyl, pyrazolidinyl, imidazolyl, imidazolinyl, imidazolidinyl, pyridyl, piperidinyl, homopiperidinyl, pyrazinyl, piperazinyl, pyrimidinyl, pyridazinyl, oxazolyl, oxazolidinyl, isoxazolyl, isoxazolidiniyl, morpholinyl, thiomorpholinyl, thiazolyl, thiazolidinyl, isothiazolyl, isothiazolidinyl, indolyl, quinolinyl, isoquinolinyl, benzimidazolyl, benzothiazolyl, benzoxazolyl, furyl, thienyl, thiazolidinyl, isothiazolyl, isoindazoyl, triazolyl, tetrazolyl, oxadiazolyl, uricyl, thiadiazolyl, pyrimidyl, tetrahydrofuranyl, dihydrofuranyl, tetrahydrothienyl, dihydrothienyl, dihydroindolyl, tetrahydroquinolyl, tetrahydroisoquinolyl, pyranyl, dihydropyranyl, dithiazolyl, benzofuranyl, benzothienyl and the like. Heterocyclic groups also include compounds of the formula

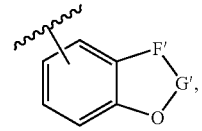

where

F' is selected from the group consisting of —CH$_2$—, —CH$_2$O— and —O—, and G' is selected from the group consisting of —C(O)— and —(C(R')(R"))$_v$—, where each of R' and R" is, independently, selected from the group consisting of hydrogen or alkyl of one to four carbon atoms, and v is one to three and includes groups, such as 1,3-benzodioxolyl, 1,4-benzodioxanyl, and the like. Any of the heterocycle groups mentioned herein may be optionally substituted with one, two, three, four or five substituents independently selected from the group consisting of: (1) alkanoyl of one to six carbon atoms; (2) alkyl of one to six carbon atoms; (3) alkoxy of one to six carbon atoms; (4) alkoxyalkyl, where the alkyl and alkylene groups are independently of one to six carbon atoms; (5) alkylsulfinyl of one to six carbon atoms; (6) alkylsulfinylalkyl, where the alkyl and alkylene groups are independently of one to six carbon atoms; (7) alkylsulfonyl of one to six carbon atoms; (8) alkylsulfonylalkyl, where the alkyl and alkylene groups are independently of one to six carbon atoms; (9) aryl; (10) amino; (11) aminoalkyl of one to six carbon atoms; (12) heteroaryl; (13) alkaryl, where the alkylene group is of one to six carbon atoms; (14) aryloyl; (15) azido; (16) azidoalkyl of one to six carbon atoms; (17) carboxaldehyde; (18) (carboxaldehyde)alkyl, where the alkylene group is of one to six carbon atoms; (19) cycloalkyl of three to eight carbon atoms; (20) alkcycloalkyl, where the cycloalkyl group is of three to eight carbon atoms and the alkylene group is of one to ten carbon atoms; (21) halo; (22) haloalkyl of one to six carbon atoms; (23) heterocyclyl; (24) (heterocyclyl)oxy; (25) (heterocyclyl)oyl; (26) hydroxy; (27) hydroxyalkyl of one to six carbon atoms; (28) nitro; (29) nitroalkyl of one to six carbon atoms; (30) N-protected amino; (31) N-protected aminoalkyl, where the alkylene group is of one to six carbon atoms; (32) oxo; (33) thioalkoxy of one to six carbon atoms; (34) thioalkoxyalkyl, where the alkyl and alkylene groups are independently of one to six carbon atoms; (35) —(CH$_2$)$_q$CO$_2$R$^A$, where q is an integer of from zero to four, and R$^A$ is selected from the group consisting of (a) alkyl, (b) aryl, and (c) alkaryl, where the alkylene group is of one to six carbon atoms; (36) —$(CH_2)_q CONR^B R^C$, where q is an integer of from zero to four and where $R^B$ and $R^C$ are independently selected from the group consisting of (a) hydrogen, (b) alkyl, (c) aryl, and (d) alkaryl, where the alkylene group is of one to six carbon atoms; (37) —$(CH_2)_q SO_2 R^D$, where q is an integer of from zero to four and where $R^D$ is selected from the group consisting of (a) alkyl, (b) aryl, and (c) alkaryl, where the alkylene group is of one to six carbon atoms; (38) —$(CH_2)_q SO_2 NR^E R^F$, where q is an integer of from zero to four and where each of $R^E$ and $R^F$ is, independently, selected from the group consisting of (a) hydrogen, (b) alkyl, (c) aryl, and (d) alkaryl, where the alkylene group is of one to six carbon atoms; (39) —$(CH_2)_q NR^G R^H$, where q is an integer of from zero to four and where each of $R^G$ and $R^H$ is, independently, selected from the group consisting of (a) hydrogen; (b) an N-protecting group; (c) alkyl of one to six carbon atoms; (d) alkenyl of two to six carbon atoms; (e) alkynyl of two to six carbon atoms; (f) aryl; (g) alkaryl, where the alkylene group is of one to six carbon atoms; (h) cycloalkyl of three to eight carbon atoms; and (i) alkcycloalkyl, where the cycloalkyl group is of three to eight carbon atoms, and the alkylene group is of one to ten carbon atoms, with the proviso that no two groups are bound to the nitrogen atom through a carbonyl group or a sulfonyl group; (40) thiol; (41) perfluoroalkyl; (42) perfluoroalkoxy; (43) aryloxy; (44) cycloalkoxy; (45) cycloalkylalkoxy; and (46) arylalkoxy.

The terms "heterocyclyloxy" and "(heterocycle)oxy," as used interchangeably herein, represent a heterocycle group, as defined herein, attached to the parent molecular group through an oxygen atom.

The terms "heterocyclyloyl" and "(heterocycle)oyl," as used interchangeably herein, represent a heterocycle group, as defined herein, attached to the parent molecular group through a carbonyl group.

The term "hydroxy" or "hydroxyl," as used herein, represents an —OH group.

The term "hydroxyalkyl," as used herein, represents an alkyl group, as defined herein, substituted by one to three hydroxy groups, with the proviso that no more than one hydroxy group may be attached to a single carbon atom of the alkyl group and is exemplified by hydroxymethyl, dihydroxypropyl, and the like.

The terms "inhibit" or "suppress" or "reduce," as relates to a function or activity, such as NOS activity, means to reduce the function or activity when compared to otherwise same conditions except for a condition or parameter of interest, or alternatively, as compared to another condition.

The term "N-protected amino," as used herein, refers to an amino group, as defined herein, to which is attached an N-protecting or nitrogen-protecting group, as defined herein.

The terms "N-protecting group" and "nitrogen protecting group," as used herein, represent those groups intended to protect an amino group against undesirable reactions during synthetic procedures. Commonly used N-protecting groups are disclosed in Greene, "Protective Groups In Organic Synthesis," $3^{rd}$ Edition (John Wiley & Sons, New York, 1999), which is incorporated herein by reference. N-protecting groups include acyl, aroyl, or carbamyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, 4-nitrobenzoyl, and chiral auxiliaries such as protected or unprotected D, L or D, L-amino acids such as alanine, leucine, phenylalanine, and the like; sulfonyl groups such as benzenesulfonyl, p-toluenesulfonyl, and the like; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxy carbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxy carbonyl, fluorenyl-9-methoxycarbonyl, cyclopentyloxycarbonyl, adamantyloxycarbonyl, cyclohexyloxycarbonyl, phenylthiocarbonyl, and the like, arylalkyl groups such as benzyl, triphenylmethyl, benzyloxymethyl, and the like and silyl groups such as trimethylsilyl, and the like. Preferred N-protecting groups are formyl, acetyl, benzoyl, pivaloyl, t-butylacetyl, alanyl, phenylsulfonyl, benzyl, t-butyloxycarbonyl (Boc), and benzyloxycarbonyl (Cbz).

The term "nitro," as used herein, represents an —$NO_2$ group.

The term "oxo" as used herein, represents =O.

The term "perfluoroalkyl," as used herein, represents an alkyl group, as defined herein, where each hydrogen radical bound to the alkyl group has been replaced by a fluoride radical. Perfluoroalkyl groups are exemplified by trifluoromethyl, pentafluoroethyl, and the like.

The term "perfluoroalkoxy," as used herein, represents an alkoxy group, as defined herein, where each hydrogen radical bound to the alkoxy group has been replaced by a fluoride radical.

The term "pharmaceutically acceptable salt," as used herein, represents those salts which are, within the scope of sound medical judgment, suitable for use in contact with the tissues of humans and animals without undue toxicity, irritation, allergic response and the like and are commensurate with a reasonable benefit/risk ratio. Pharmaceutically acceptable salts are well known in the art. For example, S. M Berge et al. describe pharmaceutically acceptable salts in detail in *J. Pharmaceutical Sciences* 66:1-19, 1977. The salts can be prepared in situ during the final isolation and purification of the compounds of the invention or separately by reacting the free base group with a suitable organic acid. Representative acid addition salts include acetate, adipate, alginate, ascorbate, aspartate, benzenesulfonate, benzoate, bisulfate, borate, butyrate, camphorate, camphersulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts and the like. Representative alkali or alkaline earth metal salts include sodium, lithium, potassium, calcium, magnesium and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine and the like.

The term "pharmaceutically acceptable prodrugs" as used herein, represents those prodrugs of the compounds of the present invention which are, within the scope of sound medical judgment, suitable for use in contact with the tissues of humans and animals with undue toxicity, irritation, allergic response, and the like, commensurate with a reasonable benefit/risk ratio, and effective for their intended use, as well as the zwitterionic forms, where possible, of the compounds of the invention.

The term "Ph" as used herein means phenyl.

The term "prodrug," as used herein, represents compounds which are rapidly transformed in vivo to the parent compound of the above formula, for example, by hydrolysis in blood. Prodrugs of the compounds of the invention may be conventional esters that are hydrolyzed to their active carboxylic acid form. Some common esters which have been utilized as prodrugs are phenyl esters, aliphatic ($C_8$-$C_{24}$) esters, acyloxymethyl esters, carbamates and amino acid esters. In another example, a compound of the invention that contains an OH group may be acylated at this position in its prodrug form. A thorough discussion is provided in T. Higuchi and V. Stella, Pro-drugs as Novel Delivery Systems, Vol. 14 of the A.C.S. Symposium Series, Edward B. Roche, ed., Bioreversible Carriers in Drug Design, American Pharmaceutical Association and Pergamon Press, 1987, and Judkins et al., *Synthetic Communications* 26(23):4351-4367, 1996, each of which is incorporated herein by reference.

Each of the terms "selectively inhibits nNOS" or "a selective nNOS inhibitor" refers to a substance, such as, for example, a compound of the invention, that inhibits or binds the nNOS isoform more effectively than the eNOS and/or iNOS isoform by an in vitro assay, such as, for example, those assays described herein. Selective inhibition can be expressed in terms of an $IC_{50}$ value, a $K_i$ value, or the inverse of a percent inhibition value, which is lower when the substance is tested in an nNOS assay than when tested in an eNOS and/or iNOS assay. Preferably, the $IC_{50}$ or $K_i$ value is 2 times lower. More preferably, the $IC_{50}$ or $K_i$ value is 5 times lower. Most preferably, the $IC_{50}$ or $K_i$ value is 10, or even 50 times lower.

The term "solvate" as used herein means a compound of the invention wherein molecules of a suitable solvent are incorporated in the crystal lattice. A suitable solvent is physiologically tolerable at the dosage administered. Examples of suitable solvents are ethanol, water and the like. When water is the solvent, the molecule is referred to as a "hydrate."

The term "spiroalkyl," as used herein, represents an alkylene diradical, both ends of which are bonded to the same carbon atom of the parent group to form a spirocyclic group.

The term "sulfonyl," as used herein, represents an —S(O)$_2$— group.

The term "thioalkheterocyclyl," as used herein, represents a thioalkoxy group substituted with a heterocyclyl group.

The term "thioalkoxy," as used herein, represents an alkyl group attached to the parent molecular group through a sulfur atom. Exemplary unsubstituted alkylthio groups are of from 1 to 6 carbons.

The term "thiol" represents an —SH group.

As used herein, and as well understood in the art, "treatment" is an approach for obtaining beneficial or desired results, such as clinical results. Beneficial or desired results can include, but are not limited to, alleviation or amelioration of one or more symptoms or conditions; diminishment of extent of disease, disorder, or condition; stabilized (i.e. not worsening) state of disease, disorder, or condition; preventing spread of disease, disorder, or condition; delay or slowing the progress of the disease, disorder, or condition; amelioration or palliation of the disease, disorder, or condition; and remission (whether partial or total), whether detectable or undetectable. "Treatment" can also mean prolonging survival as compared to expected survival if not receiving treatment. "Palliating" a disease, disorder, or condition means that the extent and/or undesirable clinical manifestations of the disease, disorder, or condition are lessened and/or time course of the progression is slowed or lengthened, as compared to the extent or time course in the absence of treatment. The term also includes prophylactic treatment.

DETAILED DESCRIPTION

Novel benzimidazole compounds having the ability to inhibit NOS while serving as an opioid receptor agonist are provided. These compounds are useful for treating or reducing the risk of diseases or disorders that benefit from a regulation of nitric oxide concentration and/or the prevention or reduction of pain. For example, the compounds of the invention are useful for treating migraine and acute, chronic, and neuropathic pain.

Accordingly, the present invention features a compound of Formula I, and pharmaceutically acceptable salts, solvates and prodrugs thereof:

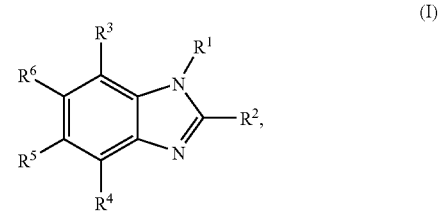

(I)

$R^1$ is optionally substituted $C_{1-6}$ alkyl, optionally substituted $C_{1-4}$ alkaryl, or optionally substituted $C_{1-4}$ alkheterocyclyl;

$R^2$ is H, Hal, optionally substituted $C_{1-6}$ alkyl, optionally substituted $C_{6-10}$ aryl, optionally substituted $C_{1-4}$ alkaryl, optionally substituted $C_{2-9}$ bridged heterocyclyl, optionally substituted $C_{1-4}$ bridged alkheterocyclyl, optionally substituted $C_{2-9}$ heterocyclyl, or optionally substituted $C_{1-4}$ alkheterocyclyl;

each of $R^3$ and $R^4$ is, independently, H, F, $C_{1-6}$ alkyl, or $C_{1-6}$ alkoxy;

$R^5$ is H, nitro, $R^{5A}C(NH)NH(CH_2)_{r5}$, $R^{5A}NHC(NH)NH(CH_2)_{r5}$, or $R^{5A}NHC(S)NH(CH_2)_{r5}$, where r5 is an integer from 0 to 2 and $R^5$ is optionally substituted $C_{1-6}$ alkyl, optionally substituted $C_{6-10}$ aryl, optionally substituted $C_{1-4}$ alkaryl, optionally substituted $C_{2-9}$ heterocyclyl, optionally substituted $C_{1-4}$ alkheterocyclyl, optionally substituted $C_{1-6}$ thioalkoxy, optionally substituted $C_{1-6}$ thioalkyl, optionally substituted $C_{1-4}$ thioalkaryl, optionally substituted aryloyl, optionally substituted $C_{1-4}$ thioalkheterocyclyl; or nitro; and $R^6$ is H, nitro, $R^{6A}C(NH)NH(CH_2)_{r6}$, $R^{6A}NHC(NH)NH(CH_2)_{r6}$, or $R^{6A}NHC(S)NH(CH_2)_{r6}$, where r6 is an integer from 0 to 2 and $R^{6A}$ is optionally substituted $C_{1-6}$ alkyl, optionally substituted $C_{6-10}$ aryl, optionally substituted $C_{1-4}$ alkaryl, optionally substituted $C_{2-9}$ heterocyclyl, optionally substituted $C_{1-4}$ alkheterocyclyl, optionally substituted $C_{1-6}$ thioalkoxy, optionally substituted $C_{1-4}$ thioalkaryl, optionally substituted aryloyl, optionally substituted $C_{1-4}$ thioalkheterocyclyl, or nitro;

where one, but not both, of $R^5$ and $R^6$ is H.

The compounds of the invention may have the formula:

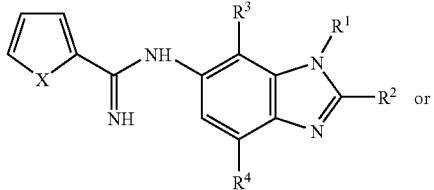

or

-continued

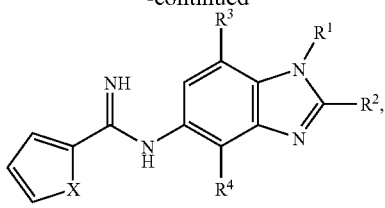

wherein X is O or S.

Other examples of a compound of formula I include those in which $R^2$ is

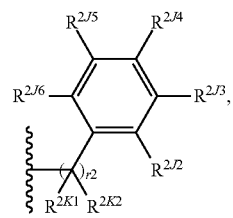

where each of $R^{2J2}$, $R^{2J3}$, $R^{2J4}$, $R^{2J5}$, and $R^{2J6}$ is, independently, $C_{1-6}$ alkyl; OH; $C_{1-6}$ alkoxy; SH; $C_{1-6}$ thioalkoxy; Halo; $NO_2$; CN; $CF_3$; $OCF_3$; $NR^{2Ja}R^{2Jb}$, where each of $R^{2Ja}$ and $R^{2Jb}$ is, independently, H or $C_{1-6}$ alkyl; $C(O)R^{2Jc}$, where $R^{2Jc}$ is H or $C_{1-6}$ alkyl; $CO_2R^{2Jd}$, where $R^{2Jd}$ is H or $C_{1-6}$ alkyl; tetrazolyl; $C(O)NR^{2Je}R^{2Jf}$, where each of $R^{2Je}$ and $R^{2Jf}$ is, independently, H or $C_{1-6}$ alkyl; $OC(O)R^{2Jg}$, where $R^{2Jg}$ is $C_{1-6}$ alkyl; $NHC(O)R^{2Jh}$, where $R^{2Jh}$ is H or $C_{1-6}$ alkyl; $SO_3H$; $S(O)_2NR^{2Ji}R^{(x)Jj}$, where each of $R^{2Ji}$ and $R^{2Jj}$ is, independently, H or $C_{1-6}$ alkyl; $S(O)R^{2Jk}$, where $R^{2Jk}$ is $C_{1-6}$ alkyl; and $S(O)_2R^{2Jl}$, where $R^{2Jl}$ is $C_{1-6}$ alkyl, r2 is an integer of 0 to 2, and each of $R^{2K1}$ and $R^{2K2}$ is, independently H or $C_{1-6}$ alkyl.

In one embodiment, $R^{2J4}$ is methoxy, ethoxy, n-propyloxy, isopropyloxy, dimethylamino, diethylamino, thiomethoxy, thioethoxy, n-propyl, isopropyl, or cyclopropyl; $R^{2J2}$, $R^{2J3}$, $R^{2J5}$, $R^{2J6}$, $R^{2K1}$, and $R^{2K2}$ are H; and r2 is 1.

In another preferred embodiment, $R^1$ is optionally substituted $C_{1-4}$ alkheterocyclyl, or an alkylamine-substituted $C_{1-6}$ alkyl, e.g., ethyl substituted at the 2-position with N,N-dimethylamine, N,N-diethylamine, N-aziridine (i.e., azacyclopropane), N-azetidane (i.e., azacyclobutane), N-pyrrolidine (i.e., azacyclopentane), N-piperidine (i.e., azacyclohexane), N-methyl-2-pyrrolidine, N-methyl-4-piperidine, or N-morpholine (i.e., 1-aza-4-oxacyclohexane).

Exemplary compounds of the invention have the following structures:

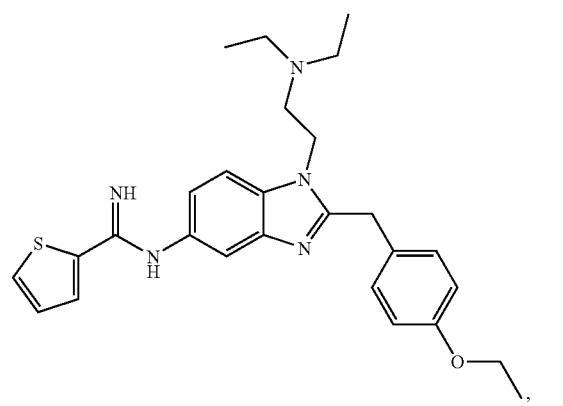

10

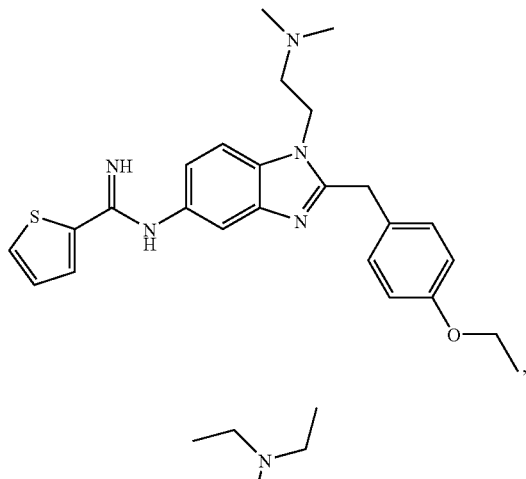

11

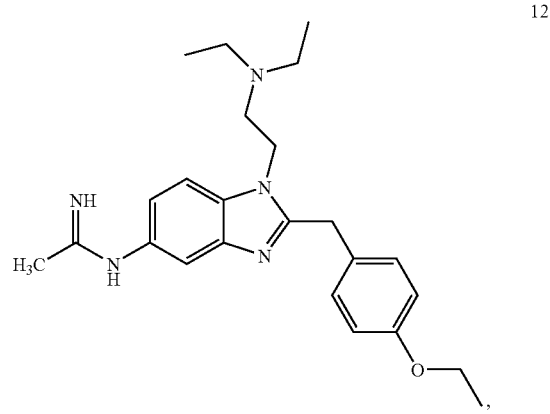

12

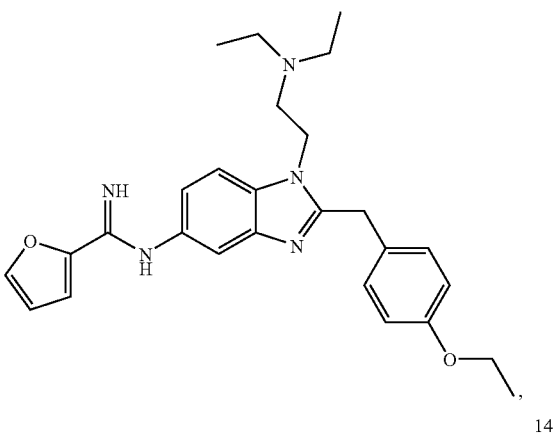

13

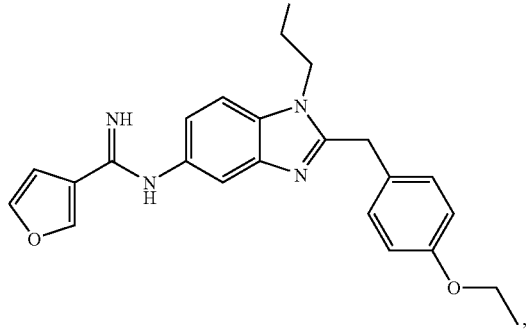

14

-continued

37
-continued
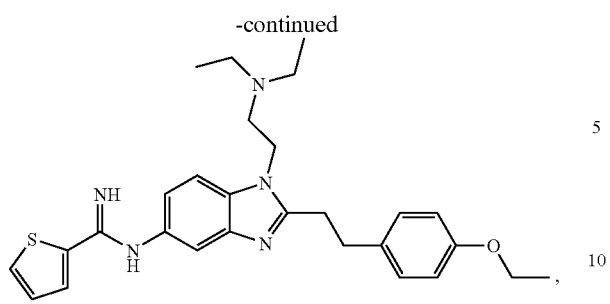
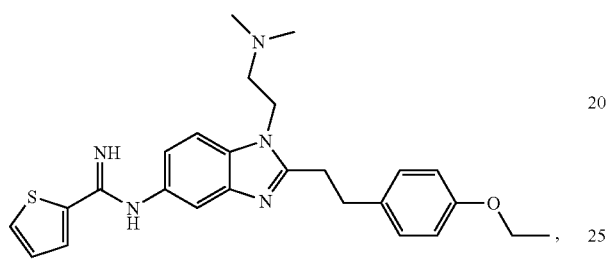
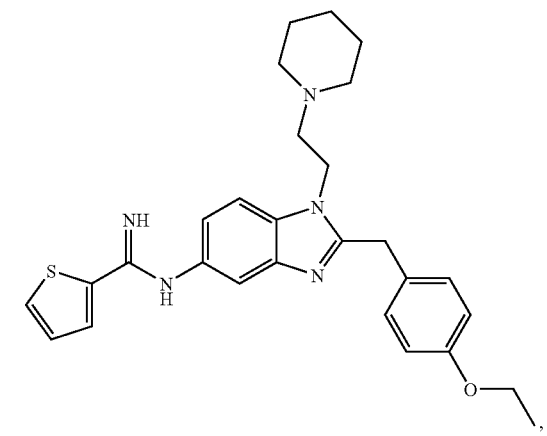
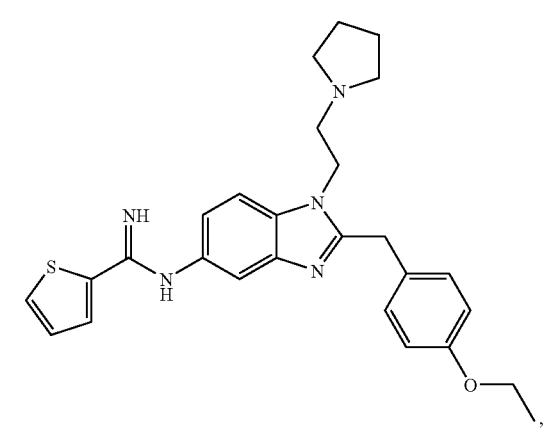
38
-continued
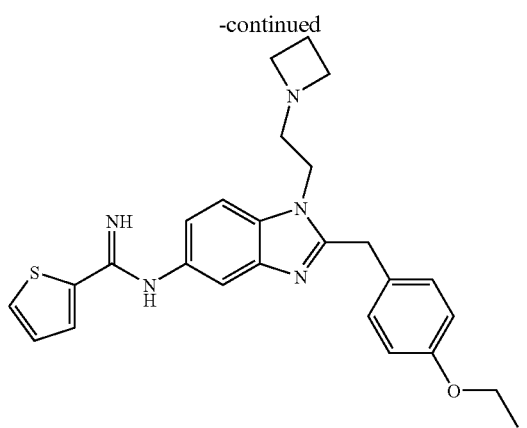
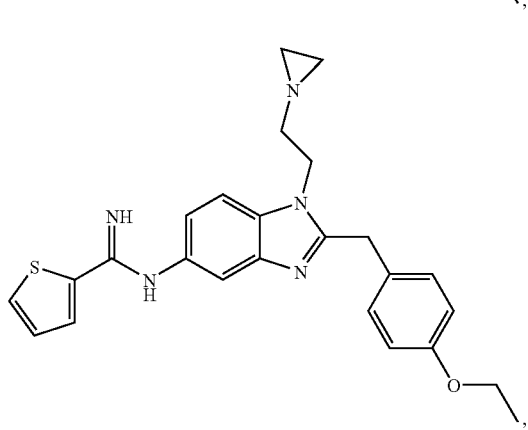
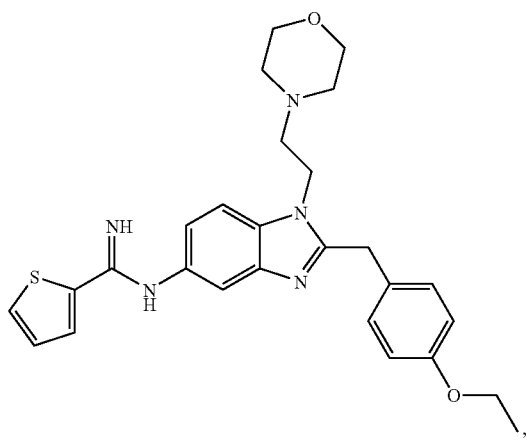
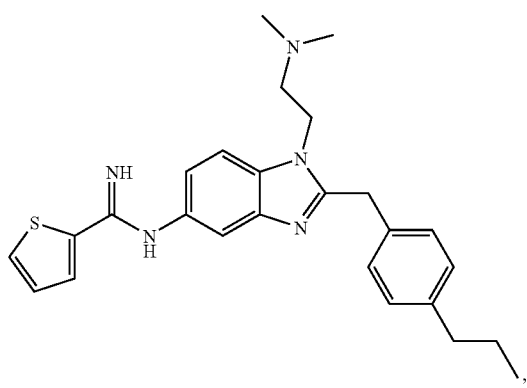

39
-continued
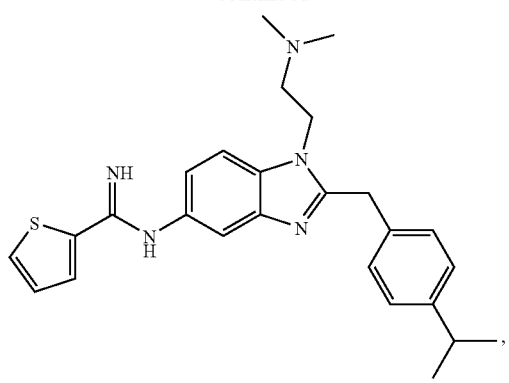
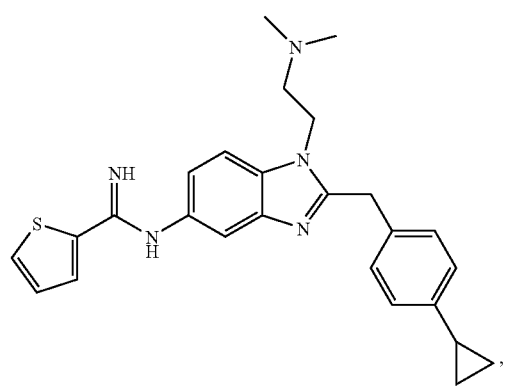
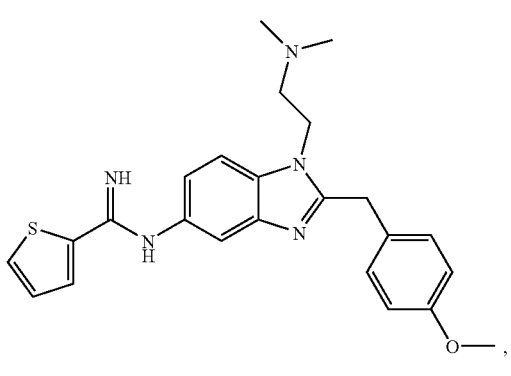
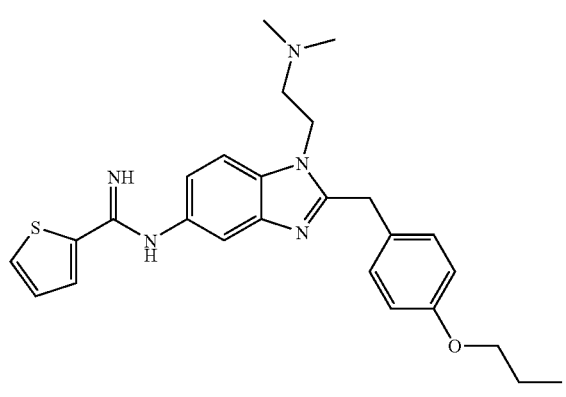
40
-continued
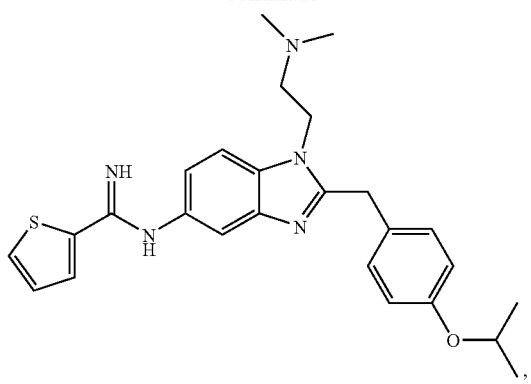
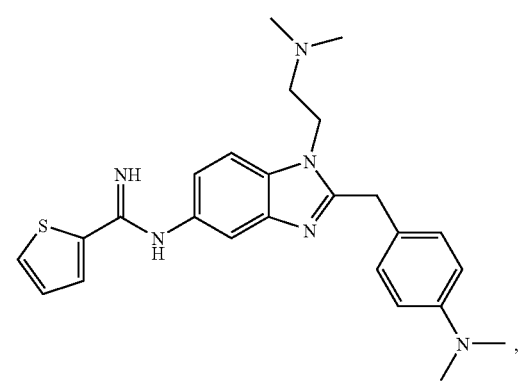
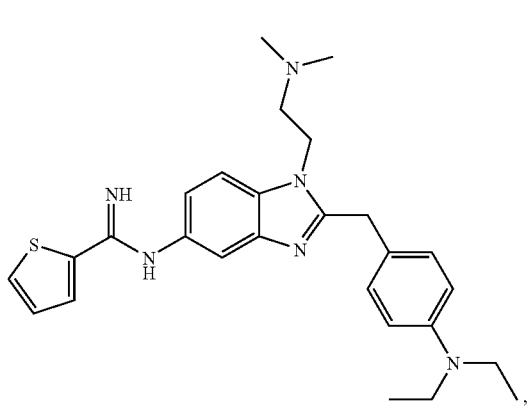
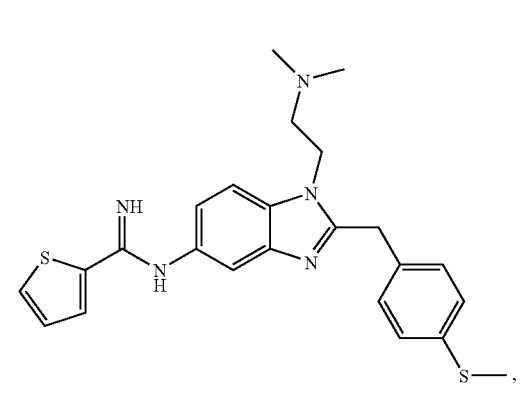

41
-continued
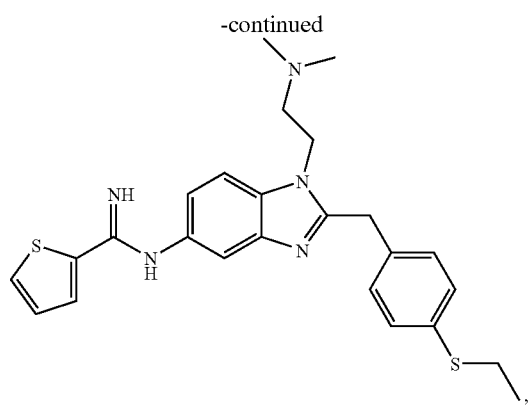
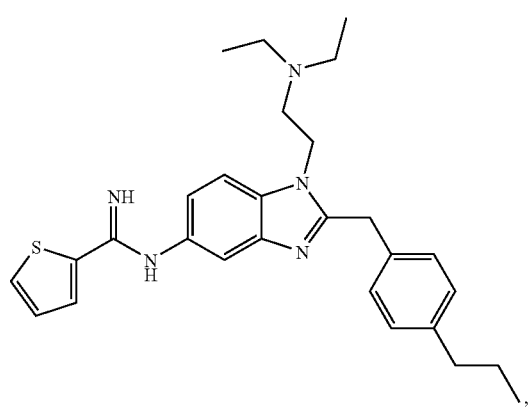
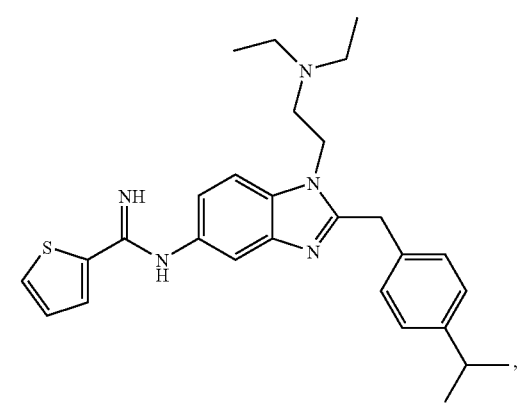
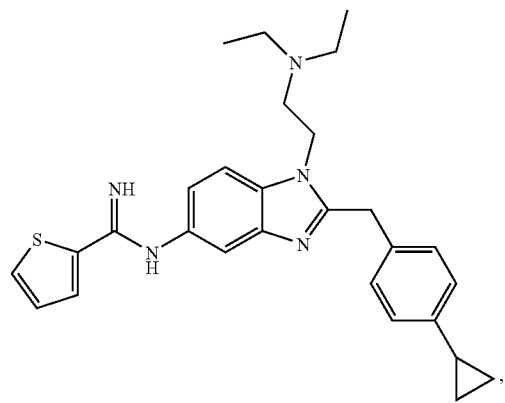
42
-continued
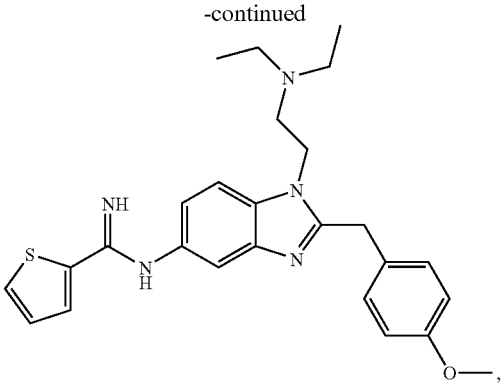
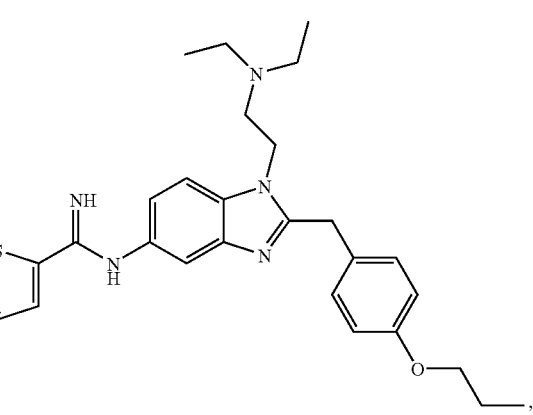
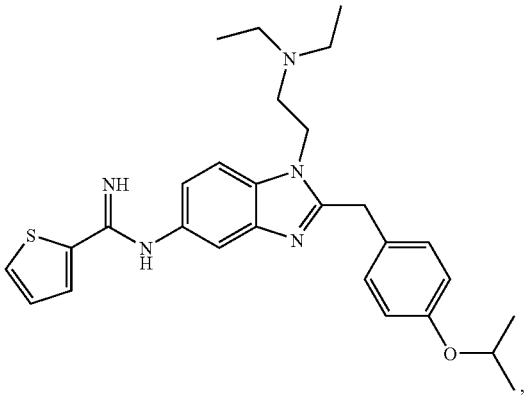
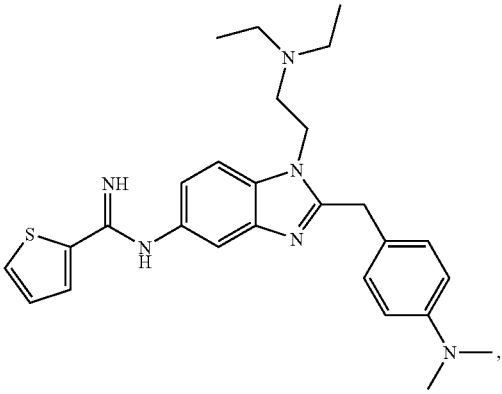

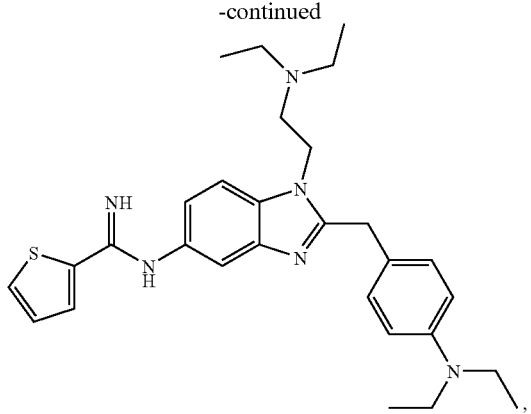

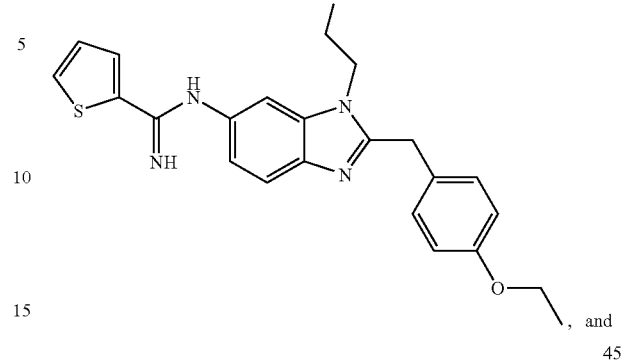

, and

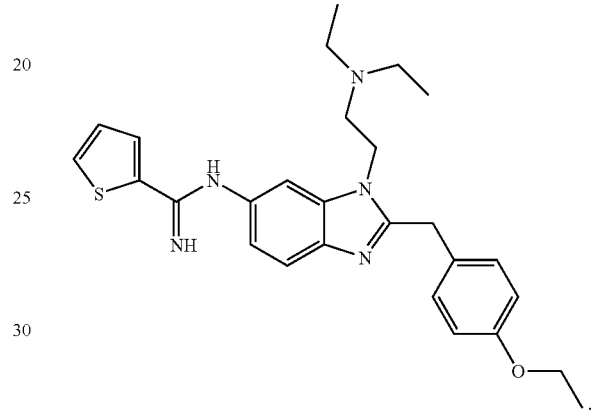

.

Methods of Preparing Compounds of the Invention

Compounds of the invention can be prepared by processes analogous to those established in the art. For example, a compound of the invention may be prepared by the reaction sequences shown in Schemes 1-10.

As shown in Scheme 1, a compound of formula IIIa or IIIb, where $R^3$ and $R^4$ are as defined elsewhere herein for a compound of formula I and Y is nitro or halo, are prepared by displacement of a leaving group LG with an amine of formula $R^1NH_2$, where $R^1$ is $(CH_2)_{m1}X^1$, with $X^1$ being

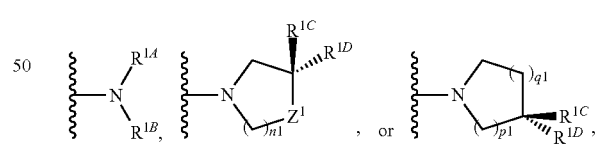

where $R^{1A}$, $R^{1B}$, $R^{1C}$, $R^{1D}$, $Z^1$, m1, n1, p1, and q1 are as defined elsewhere herein for a compound of formula I. The reaction can be performed by conventional means, such as, for example, in a protic solvent such as ethanol at reflux, or optionally in an aprotic polar solvent such as DMF. A suitable base may also be used in conjunction with the solvent. Suitable leaving groups (LG) include halogens or triflate. Preferably, the LG is fluoro or chloro. A compound of formula IIIa or IIIb can be reduced to a compound of formula IVa or IVb, respectively, with aqueous ammonium sulfide $((NH_4)_2S)$ in hot ethanol as described by von A. Hunger et al., in *Helv. Chim. Acta.* 132:1033-1047, 1960.

Scheme 1

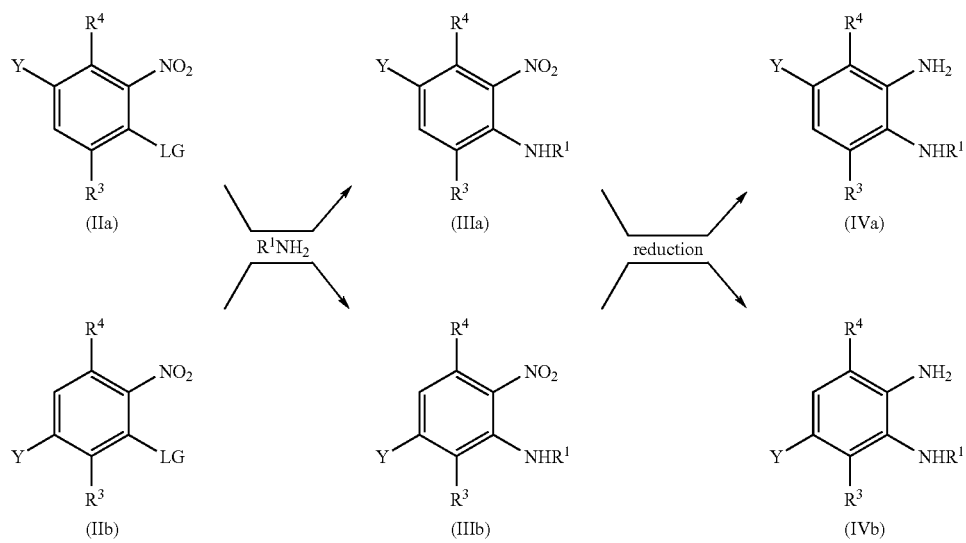

As shown in Scheme 2, a compound of formula IVa or IVb can then be reacted directly with a compound of formula V, where LG is Cl, F, or a suitable mixed anhydride, or with the corresponding carboxylic acid (LG=OH) under standard amide-forming coupling conditions, to give a compound of formula VIa or VIb, respectively. In one example, $R^2$ is 4-ethoxybenzyl and the reaction is performed in refluxing dichloromethane with amide-forming coupling reagent is EEDQ (ethoxy-1-ethoxycarbonyl-1,2-dihydroquinoline) present in a stoichiometric amount. In another example, $R^2$ is 4-ethoxybenzyl and the reaction is performed in DMF with a stoichiometric amount of the water-soluble carbodiimide EDAC(N-(3-dimethylaminpropyl)-N'-ethylcarbodiimide), a suitable base (eg. triethylamine), and HOBt (hydroxybenzotriazole) present.

Scheme 2

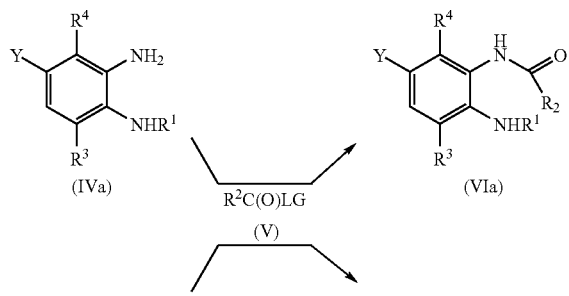

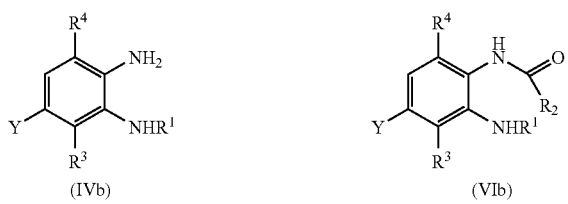

As shown in Scheme 3, a compound of formula VIIa or VIIb can be prepared by dehydration of a compound of formula VIa and VIb, respectively, using a suitable dehydrating reagent such as, for example, $PCl_5$, EEDQ, or Burgess dehydrating reagent, in a suitable solvent or cosolvent such as, for example, dichloromethane or chloroform, preferably at reflux. Alternatively, a compound of formula VIIa or VIIb may be prepared in one step by reacting a compound of formula IVa or IVb, respectively, with a compound of formula V, utilizing an excess of EEDQ according to known methods (e.g., Thomas et al., *Tett. Lett.* 38(29):5099-5102, 1997; or Carroll and Coleman, *J. Med. Chem.* 18(3): 318-320, 1975).

Scheme 3

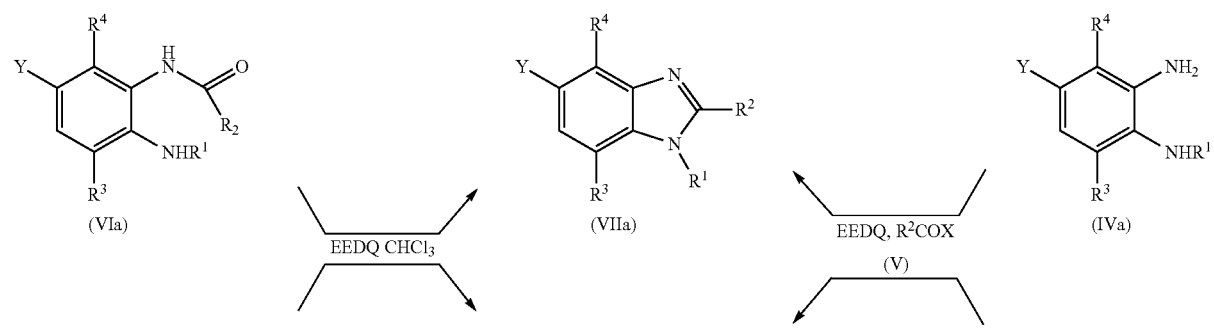

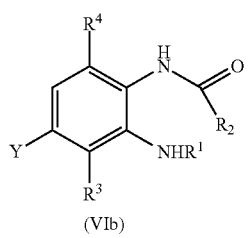

(VIb)

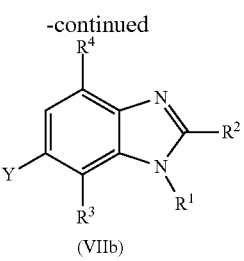

(VIIb)

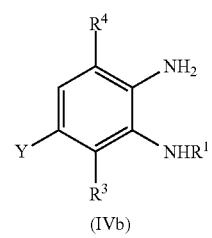

(IVb)

As shown in Scheme 4, a compound of formula VII may be alkylated under standard conditions with a compound having the formula: $R^1$-LG, where $R^1$ is as previously defined elsewhere herein and LG is a chloro, bromo, iodo, or a sulfonate, to give a mixture of alkylation products VIIa and VIb. The ratio of the 5-Y and 6-Y-substituted isomers can be controlled by suitable choice of solvent and temperature as described in U.S. Pat. No. 2,935,514. The mixture can then be purified by standard chromatography techniques or recrystallization procedures (for example, those described in U.S. Pat. No. 2,935,514).

As shown in Scheme 5, a compound of formula VIIa or VIIb, where each of $R^1$, $R^2$, $R^3$, and $R^4$ is as defined elsewhere herein and Y is $NO_2$, can be subjected to reducing conditions to prepare a compound of formula VIIIa or VIIIb, respectively, where Y is $NH_2$. For example, reducing conditions can include the use of $SnCl_2$ in a polar solvent, such as, for example, ethanol at refluxing temperatures. Alternatively, reducing conditions can include hydrogenation using a suitable catalyst, such as palladium on charcoal, in ethanol or another solvent or combinations of solvents. Alternatively, a compound of formula VIIIa or VIIIb can also be prepared by metal catalyzed amination of a compound of formula VIIa or VIIb, respectively, where Y is chloro, bromo, iodo, or triflate (Wolfe, et al. *J. Org. Chem.* 65:1158-1174, 2000) in the presence of a suitable ammonia equivalent, such as benzophenone imine, $LiN(SiMe_3)_2$, $Ph_3SiNH_2$, $NaN(SiMe_3)_2$, or lithium amide (Huang and Buchwald, *Org. Lett.* 3(21):3417-3419, 2001). Examples of suitable metal catalysts include, for example, a palladium catalyst coordinated to suitable ligands. A suitable leaving group for palladium catalyzed amination may also be nonaflate (Anderson, et al., *J. Org. Chem.* 68:9563-9573, 2003) or boronic acid (Antilla and Buchwald, *Org. Lett.* 3(13):2077-2079, 2001) when the metal is a copper salt, such as Cu(II) acetate, in the presence of suitable additives, such as 2,6-lutidine. A preferred leaving group is bromo in the presence of palladium (0) or palladium (II) catalyst. Suitable palladium catalysts include tris-dibenzylideneacetone dipalladium ($Pd_2$ $dba_3$) and palladium acetate ($PdOAc_2$), preferably $Pd_2$ $dba_3$. Suitable ligands for palladium can vary greatly and may include, for example, Xant-Phos, BINAP, DPEphos, dppf, dppb, DPPP, (o-biphenyl)-P(t-Bu)$_2$, (o-biphenyl)-P(Cy)$_2$, P(t-Bu)$_3$, P(Cy)$_3$, and others (Huang and Buchwald, *Org. Lett.* 3(21):3417-3419, 2001). Preferably the ligand is P(t-Bu)$_3$. Suitable solvents for the Pd-catalyzed amination include THF, dioxane, toluene, xylene, and DME at temperatures between room temperature and reflux.

Scheme 4

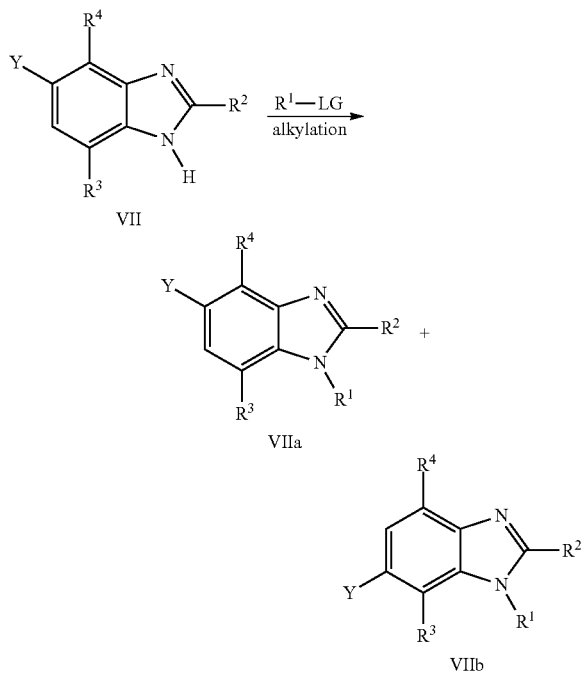

Scheme 5

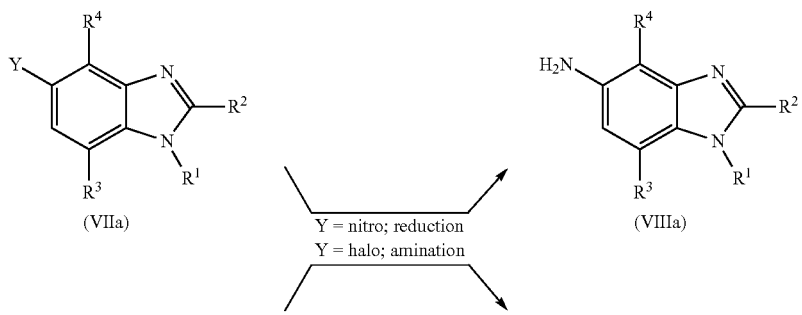

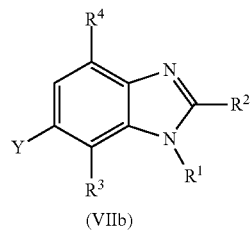

(VIIb)

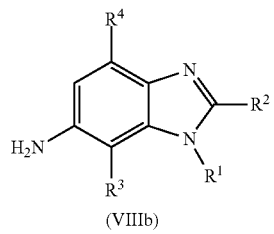

(VIIIb)

A compound of formula XIa or XIb, where each of $R^{5A}$ or $R^{5B}$ is as defined elsewhere herein and Q is an aryl group (e.g., a phenyl group), a $C_1$ alkaryl group (e.g., a naphthylmethyl group), or an alkyl group (e.g., a methyl group) are either commercially available or may be prepared according to Scheme 6 by reacting thiol-containing compounds of formula X with a cyano compound of formula IXa or IXb, respectively. Other examples of this transformation are described in the prior art (see, for example, Baati et al., *Synlett* 6:927-9, 1999; EP 262873 1988, Collins et al., *J. Med. Chem.* 41:15, 1998).

Scheme 6

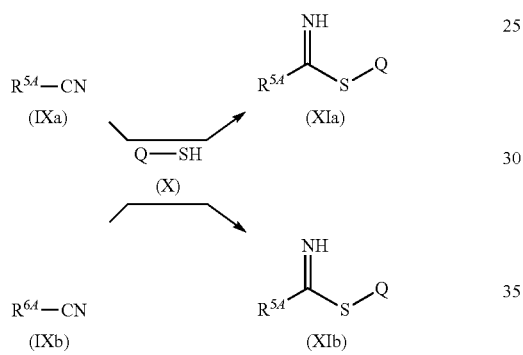

As shown in Scheme 7, a compound of formula XIIa or XIIb, where each of $R^1$, $R^2$, $R^3$, $R^4$, $R^{5A}$, and $R^{5B}$ is as defined elsewhere herein, can be prepared by reacting a compound of formula VIIIa or VIIb with a compound of formula XIa or XIb, respectively, where Q is defined as above, in a suitable solvent, such as, for example, ethanol or methanol.

Scheme 7

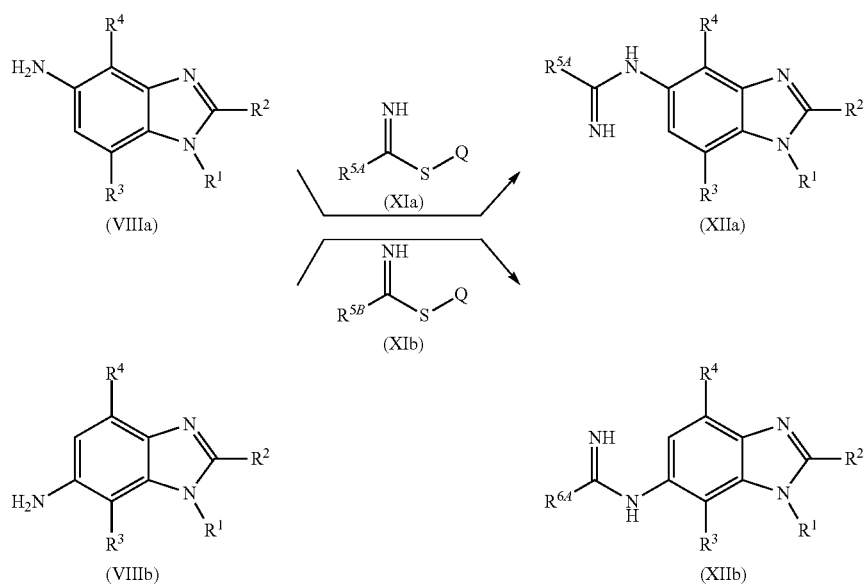

As shown in Scheme 8, a compound of formula XIVa or XIVb, where each of $R^1$, $R^2$, $R^3$, and $R^4$ is as defined elsewhere herein, can be prepared by reacting a compound of formula VIIIa or VIIb with a compound of formula XIIIa or XIIIb, respectively, where each of $R^{5B}$ and $R^{6B}$ is $C_{1-6}$ alkyl, $C_{6-10}$ aryl, $C_{1-4}$ alkaryl, $C_{2-9}$ heteroaryl, $C_{1-4}$ alkheteroaryl, —C(O)$C_{1-6}$ alkyl, —C(O)$C_{6-10}$ aryl, —C(O)$C_{1-4}$ alkaryl, —C(O)$C_{2-9}$ heteroaryl, or —C(O)$C_{1-4}$ alkheteroaryl. The reaction can be performed in an inert solvent, such as tetrahydrofuran or dichloromethane, at ambient temperature or with heating. A compound of formula XIVa or XIVb, where the thiourea is bonded to a carbonyl moiety, can be hydrolyzed under standard conditions, such as, for example, aqueous sodium hydroxide in tetrahydrofuran to produce a compound of XVa or XVb, respectively.

Scheme 8

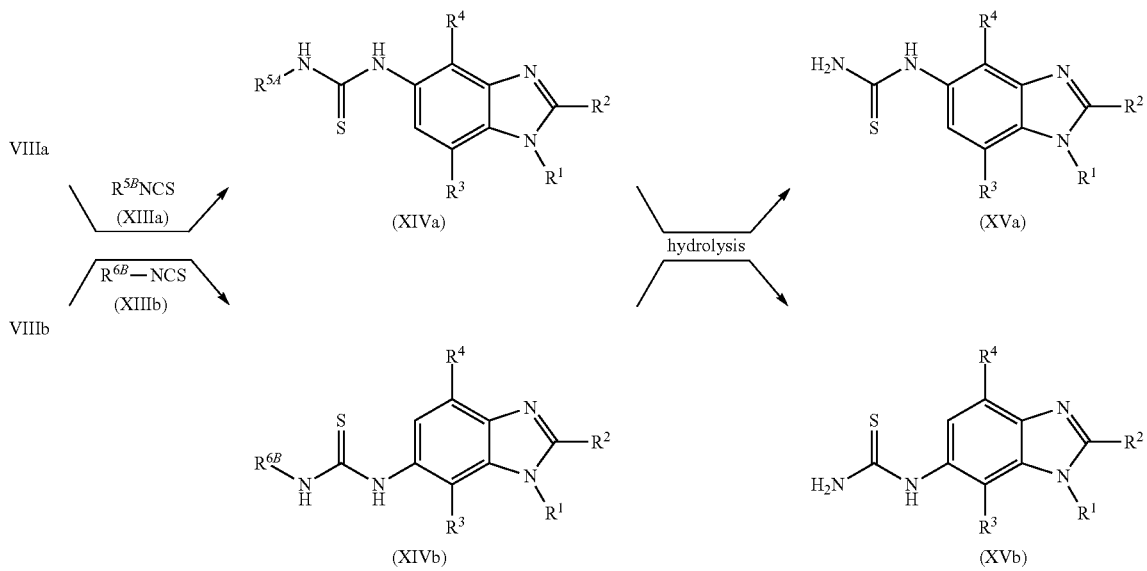

As shown in Scheme 9, a compound of XVIa or XVIb can be produced by reacting a compound of formula XIVa or XIVb, respectively, where $R^{5B}$ or $R^{6B}$ is H, with an alkylating agent, such as, for example, $R^{5C}$-LG or $R^{6C}$-LG, where $R^{5C}$ or $R^{6C}$ can be $C_{1-6}$ alkyl, $C_{1-4}$ alkaryl, or $C_{1-4}$ alkheteroaryl and LG is a suitable leaving group, such as, for example, chloro, bromo, iodo, or sulfonate (e.g., mesylate or tosylate) in a suitable solvent such as dichloromethane or DMF.

Scheme 9

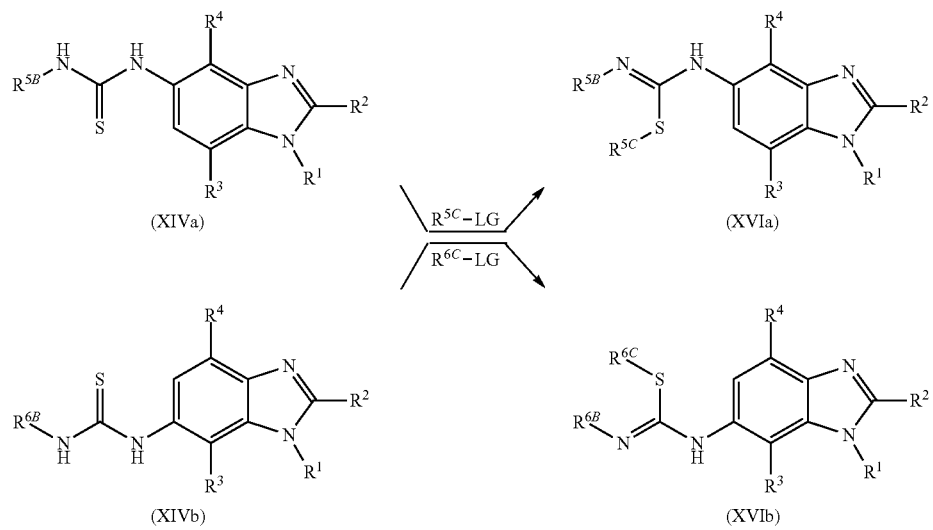

In some cases the chemistries outlined above may have to be modified, for instance, by the use of protective groups to prevent side reactions due to reactive groups, such as reactive groups attached as substituents. This may be achieved by means of conventional protecting groups as described in "Protective Groups in Organic Chemistry," McOmie, Ed., Plenum Press, 1973 and in Greene and Wuts, "Protective Groups in Organic Synthesis," John Wiley & Sons, 3$^{rd}$ Edition, 1999.

The compounds of the invention, and intermediates in the preparation of the compounds of the invention, may be isolated from their reaction mixtures and purified (if necessary) using conventional techniques, including extraction, chromatography, distillation and recrystallization.

The formation of a desired compound salt is achieved using standard techniques. For example, the neutral compound is treated with an acid in a suitable solvent and the formed salt is isolated by filtration, extraction, or any other suitable method.

The formation of solvates of the compounds of the invention will vary depending on the compound and the solvate. In general, solvates are formed by dissolving the compound in the appropriate solvent and isolating the solvate by cooling or adding an antisolvent. The solvate is typically dried or azeotroped under ambient conditions.

Preparation of an Optical Isomer of a Compound of the Invention May be performed by reaction of the appropriate optically active starting materials under reaction conditions which will not cause racemization. Alternatively, the individual enantiomers may be isolated by separation of a racemic mixture using standard techniques, such as, for example, fractional crystallization or chiral HPLC.

A radiolabeled compound of the invention may be prepared using standard methods known in the art. For example, tritium may be incorporated into a compound of the invention using standard techniques, such as, for example, by hydrogenation of a suitable precursor to a compound of the invention using tritium gas and a catalyst. Alternatively, a compound of the invention containing radioactive iodine may be prepared from the corresponding trialkyltin (suitably trimethyltin) derivative using standard iodination conditions, such as [$^{125}$I] sodium iodide in the presence of chloramine-T in a suitable solvent, such as dimethylformamide. The trialkyltin compound may be prepared from the corresponding non-radioactive halo, suitably iodo, compound using standard palladium-catalyzed stannylation conditions, such as, for example, hexamethylditin in the presence of tetrakis(triphenylphosphine) palladium (0) in an inert solvent, such as dioxane, and at elevated temperatures, suitably 50-100° C.

Pharmaceutical Uses

The present invention features all uses for a compound of formula I, including their use in therapeutic methods, whether alone or in combination with another therapeutic substance, their use in compositions for inhibiting NOS activity, their use in diagnostic assays, and their use as research tools.

The compounds of the invention have useful NOS inhibiting activity, and therefore are useful for treating, preventing, or reducing the risk of, diseases or conditions that are ameliorated by a reduction in NOS activity. Such diseases or conditions include those in which the synthesis or oversynthesis of nitric oxide plays a contributory part.

In addition, compounds of formula I have useful activity at opioid receptors, particularly the mu opioid receptor, and therefore are useful in the prevention, amelioration, or treatment of diseases or conditions which benefit from the agonism, partial agonism, or antagonism of opioid receptors, such as, for example, the use of a compound of formula I to antagonize opioid receptors in the prevention or treatment of pain.

Accordingly, the present invention features a method of treating, preventing, or reducing the risk of, a disease or condition caused by NOS activity, and/or of preventing, ameliorating, or reducing pain, that includes administering an effective amount of a compound of the invention to a cell or animal in need thereof. Such diseases or conditions include, for example, migraine headache with and without aura or allodynia, neuropathic pain, chronic tension type headache, chronic pain, prevention of the development of chronic pain from acute pain, acute pain (e.g., post-operative pain), acute spinal cord injury, post stroke pain (CPSP), hyperalgesia, diabetic neuropathy, diabetic nephropathy, glaucoma, macular degeneration, an inflammatory disease, including a reversible obstructive airway disease (e.g., asthma or adult respiratory distress syndrome (ARDS)), stroke, reperfusion injury, head trauma, cardiogenic shock, traumatic shock, coronary artery bypass graft (CABG) associated neurological damage, HCA, AIDS associated dementia, neurotoxicity, neurodegeneration, Parkinson's disease, Alzheimer's disease, ALS, Huntington's disease, multiple sclerosis, metamphetamine-induced neurotoxicity, drug addiction, such as, for example, cocaine addiction, morphine/opioid-induced tolerance or opioid-induced hyperalgesia, dependence, or withdrawal, ethanol tolerance, dependence, or withdrawal, epilepsy, anxiety, depression, attention deficit disorder, psychosis, gastrointestinal disorders, and irritable bowel syndrome.

Compounds of Formula I of the present invention have been found to exhibit selective inhibition of the neuronal isoform of NOS. NO produced by the nNOS isoform during cerebral ischemia may contribute to the initial metabolic deterioration of the ischemic penumbra, resulting in larger infarcts. Therefore, selective inhibition of nNOS activity is particularly beneficial for reducing the risk of or treating a condition selected from stroke, reperfusion injury, neurodegeneration, head trauma, CABG neurological damage, migraine, neuropathic pain, and chronic pain. Following are exemplary conditions that may be treated using the compounds of the invention and their association with NOS activity.

(1) Migraine

The first observation by Asciano Sobrero in 1847 that small quantities of nitroglycerine, an NO releasing agent, causes severe headache lead to the nitric oxide hypothesis of migraine (Olesen et al., *Cephalagia* 15:94-100, 1995). Serotonergic 5HT$_{1D/1B}$ agonists, such as sumatriptan, which are used clinically in the treatment of migraine, are known to prevent the cortical spreading depression in the lissencephalic and gyrencephalic brain during migraine attack, a process resulting in widespread release of NO. Indeed, it has been shown that sumatriptan modifies the artificially enhanced cortical NO levels following infusion of glyceryl trinitate in rats (Read et al., *Brain Res.* 847:1-8, 1999; ibid, 870(1-2):44-53, 2000). In a human randomized double-blinded clinical trial for migraine, a 67% response rate after single i.v. administration of L-N$^G$ methylarginine hydrochloride (L-NMMA, an NOS inhibitor) was observed. The effect was not attributed to a simple vasoconstriction since no effect was observed on transcranial doppler determined velocity in the middle cerbral artery (Lassen et al., *Lancet* 349:401-402, 1997). In an open pilot study using the NO scavenger hydroxycobalamin, a reduction in the frequency of migraine attack of 50% was observed in 53% of the patients and a reduction in the total duration of migraine attacks was also observed (van der Kuy et al., *Cephalgia* 22(7):513-519, 2002).

(2) Migraine with Allodynia

Clinical studies have shown that as many as 75% of patients develop cutaneous allodynia (exaggerated skin sensitivity) during migraine attacks and that its development during migraine is detrimental to the anti-migraine action of triptan $5HT_{1B/1D}$ agonists (Burstein et al., *Ann. Neurol.* 47:614-624, 2000; Burstein et al., *Brain,* 123:1703-1709, 2000). While the early administration of triptans such as sumatriptan can terminate migraine pain, late sumatriptan intervention is unable to terminate migraine pain or reverse the exaggerated skin sensitivity in migraine patients already associated with allodynia (Burstein et al., *Ann. Neurol.* DOI: 10.1002/ana.10785, 2003; Burstein and Jakubowski, *Ann. Neurol.,* 55:27-36, 2004). The development of peripheral and central sensitization correlates with the clinical manifestations of migraine. In migraine patients, throbbing occurs 5-20 minutes after the onset of headache, whereas cutaneous allodynia starts between 20-120 minutes (Burstein et al., *Brain,* 123:1703-1709, 2000). In the rat, experimentally induced peripheral sensitization of meningeal nociceptors occurs within 5-20 minutes after applying an inflammatory soup (I.S.) to the dura (Levy and Strassman, *J. Physiol.,* 538:483-493, 2002), whereas central sensitization of trigeminovascular neurons develops between 20-120 minutes (Burstein et al., *J. Neurophysiol.* 79:964-982, 1998) after I.S. administration. Parallel effects on the early or late administration of antimigraine triptans like sumatriptan on the development of central sensitization have been demonstrated in the rat (Burstein and Jakubowski, vide supra). Thus, early but not late sumatriptan prevents the long-term increase in I.S.-induced spontaneous activity seen in central trigeminovascular neurons (a clinical correlate of migraine pain intensity). In addition, late sumatriptan intervention in rats did not prevent I.S.-induced neuronal sensitivity to mechanical stimulation at the periorbital skin, nor decreased the threshold to heat (a clinical correlate of patients with mechanical and thermal allodynia in the periorbital area). In contrast, early sumatriptan prevented I.S. from inducing both thermal and mechanical hypersensitivity. After the development of central sensitization, late sumatriptan intervention reverses the enlargement of dural receptive fields and increases in sensitivity to dural indentation (a clinical correlate of pain throbbing exacerbated by bending over) while early intervention prevents its development.

Previous studies on migraine compounds such as sumatriptan (Kaube et al., *Br. J. Pharmacol.* 109:788-792, 1993), zolmitriptan (Goadsby et al., *Pain* 67:355-359, 1996), naratriptan (Goadsby et al., *Br. J. Pharmacol.,* 328:37-40, 1997), rizatriptan (Cumberbatch et al., *Eur. J. Pharmacol.,* 362:43-46, 1998), or L-471-604 (Cumberbatch et al., *Br. J. Pharmacol.* 126:1478-1486, 1999) examined their effects on nonsensitized central trigeminovascular neurons (under normal conditions) and thus do not reflect on their effects under the pathophysiolocal conditions of migraine. While triptans are effective in terminating the throbbing of migraine whether administered early or late, the peripheral action of sumatriptan is unable to terminate migraine pain with allodynia following late intervention via the effects of central sensitization of trigeminovascular neurons. The limitations of triptans suggest that improvement in the treatment of migraine pain can be achieved by utilizing drugs that can abort ongoing central sensitization, such as the compounds of the present invention.

It has been shown that systemic nitroglycerin increases nNOS levels and c-Fos-immunoreactive neurons (a marker neuronal activation) in rat trigeminal nucleus caudalis after 4 hours, suggesting NO likely mediates central sensitization of trigeminal neurons (Pardutz et al., *Neuroreport* 11(14):3071-3075, 2000). In addition, L-NAME can attenuate Fos expression in the trigeminal nucleus caudalis after prolonged (2 hrs) electrical stimulation of the superior sagittal sinus (Hoskin et al. *Neurosci. Lett.* 266(3):173-6, 1999). Taken together with ability of NOS inhibitors to abort acute migraine attack (Lassen et al., *Cephalalgia* 18(1):27-32, 1998), the compounds of the invention, alone or in combination with other antinociceptive agents, represent excellent candidate therapeutics for aborting migraine in patients after the development of allodynia.

(3) Chronic Headache (CTTH)

NO contributes to the sensory transmission in the peripheral (Aley et al., *J. Neurosci.* 1:7008-7014, 1998) and central nervous system (Meller and Gebhart, *Pain* 52:127-136, 1993). Substantial experimental evidence indicates that central sensitization, generated by prolonged nociceptive input from the periphery, increases excitability of neurons in the CNS and is caused by, or associated with, an increase in NOS activation and NO synthesis (Bendtsen, *Cephalagia* 20:486-508, 2000; Woolf and Salter, *Science* 288:1765-1769, 2000). It has been shown that experimental infusion of the NO donor, glyceryl trinitrate, induces headache in patients. In a double-blinded study, patients with chronic tension-type headache receiving L-NMMA (an NOS inhibitor) had a significant reduction in headache intensity (Ashina and Bendtsen, *J. Headache Pain* 2:21-24, 2001; Ashina et al., *Lancet* 243 (9149):287-9, 1999). Thus the NOS inhibitors of the present invention may be useful for the treatment of chronic tension-type headache.

(4) Acute Spinal Cord Injury, Chronic or Neuropathic Pain

In humans, NO evokes pain on intracutaneous injection (Holthusen and Arndt, *Neurosci. Lett.* 165:71-74, 1994), thus showing a direct involvement of NO in pain. Furthermore, NOS inhibitors have little or no effect on nociceptive transmission under normal conditions (Meller and Gebhart, *Pain* 52:127-136, 1993). NO is involved in the transmission and modulation of nociceptive information at the periphery, spinal cord and supraspinal level (Duarte et al., *Eur. J. Pharmacol.* 217:225-227, 1992; Haley et al., *Neuroscience* 31:251-258, 1992). Lesions or dysfunctions in the CNS may lead to the development of chronic pain symptoms, known as central pain, and includes spontaneous pain, hyperalgesia, and mechanical and cold allodynia (Pagni, *Textbook of Pain,* Churchill Livingstone, Edinburgh, 1989, pp. 634-655; Tasker In: *The Management of Pain,* pp. 264-283, J. J. Bonica (Ed.), Lea and Febiger, Philadelphia, Pa., 1990; Casey, Pain and Central Nervous System Disease: The Central Pain Syndromes, pp. 1-11 K. L. Casey (Ed.), Raven Press, New York, 1991). It has been demonstrated that systemic administration (i.p.) of the NOS inhibitors 7-NI and L-NAME relieve chronic allodynia-like symptoms in rats with spinal cord injury (Hao and Xu, *Pain* 66:313-319, 1996). The effects of 7-NI were not associated with a significant sedative effect and were reversed by L-arginine (NO precursor). The maintenance of thermal hyperalgesia is believed to be mediated by nitric oxide in the lumbar spinal cord and can be blocked by intrathecal administration of a nitric oxide synthase inhibitor like L-NAME or soluble guanylate cyclase inhibitor methylene blue (*Neuroscience* 50(1):7-10, 1992). Thus the NOS inhibitors of the present invention may be useful for the treatment of chronic or neuropathic pain.

(5) Diabetic Neuropathy

The endogenous polyamine metabolite agmatine is a metabolite of arginine that is both an NOS inhibitor and N-methyl-D-aspartate (NMDA) channel antagonist. Agmatine is effective in both the spinal nerve ligation (SNL) model of neuropathic pain as well as the streptozotocin model of diabetic neuropathy (Karadag et al., *Neurosci. Lett.* 339(1): 88-90, 2003). Thus compounds possessing NOS inhibitory activity, such as, for example, a compound of formula I, a combination of an NOS inhibitor and an NMDA antagonist should be effective in treating diabetic neuropathy and other neuropathic pain conditions.

(6) Inflammatory Diseases and Neuroinflammation

LPS, a well known pharmacological tool, induces inflammation in many tissues and activates NFκB in all brain regions when administered intravenously. It also activates pro-inflammatory genes when injected locally into the striaitum (Stern et al., *J. Neuroimmunology*, 109:245-260, 2000). Recently it has been shown that both the NMDA receptor antagonist MK801 and the brain selective nNOS inhibitor 7-NI both reduce NFκB activation in the brain and thus reveal a clear role for glutamate and NO pathway in neuroinflammation (Glezer et al., *Neuropharmacology* 45(8):1120-1129, 2003). Thus, the administration of a compound of the invention, either alone or in combination with an NMDA antagonist, should be effective in treating diseases arising from neuroinflammation.

(7) Stroke and Reperfusion Injury

The role of NO in cerebral ischemia can be protective or destructive depending on the stage of evolution of the ischemic process and on the cellular compartment producing NO (Dalkara et al., *Brain Pathology* 4:49, 1994). While the NO produced by eNOS is likely beneficial by acting as a vasodilator to improve blood flow to the affected area (Huang et al., *J. Cereb. Blood Flow Metab.* 16:981, 1996), NO produced by nNOS contributes to the initial metabolic deterioration of the ischemic penumbra, resulting in larger infarcts (Hara et al., *J. Cereb. Blood Flow Metab.* 16:605, 1996). The metabolic derangement that occurs during ischemia and subsequent reperfusion results in the expression and release of several cytokines that activate iNOS in several cell types including some of the central nervous system. NO can be produced at cytotoxic levels by iNOS, and increased levels of iNOS contribute to progressive tissue damage in the penumbra, leading to larger infarcts (Parmentier et al., *Br. J. Pharmacol.* 127:546, 1999). Inhibition of i-NOS has been shown to ameliorate cerebral ischemic damage in rats (*Am. J. Physiol.* 268:R286, 1995).

It has been shown that a synergistic neuroprotective effect is observed upon the combined administration of an NMDA antagonist (eg MK-801 or LY293558) with nNOS selective inhibitors (7-NI or ARL17477) in global cerebral ischemia (Hicks et al., *Eur. J. Pharmacol.* 381:113-119, 1999). Thus the compounds of the invention, administered either alone or in combination with NMDA antagonists, or compounds possessing mixed nNOS/NMDA activity, may be effective in treating conditions of stroke and other neurodegenerative disorders.

(8) Complications Resulting from Coronary Artery Bypass Surgery

Cerebral damage and cognitive dysfunction still remains as a major complication of patients undergoing coronary artery bypass surgery (CABG) (Roch et al., *N. Eng. J. Med.* 335: 1857-1864, 1996; Shaw et al., *Q. J. Med.* 58:59-68, 1986). This cerebral impairment following surgery is a result of ischemia from preoperative cerebral microembolism. In a randomized trial of the NMDA antagonist remacemide, patients showed a significant overall postoperative improvement in learning ability in addition to reduced deficits (Arrowsmith et al., *Stroke* 29:2357-2362, 1998). Given the involvement of excitotoxicity produced by excessive release of glutamate and calcium influx, it is expected that a neuroprotective agent, such as a compound of the invention or an NMDA antagonist, either alone or in combination, may have a beneficial effect improving neurological outcomes after CABG.

(9) AIDS-Associated Dementia

HIV-1 infection can give rise to dementia. The HIV-1 coat protein gp-120 kills neurons in primary cortical cultures at low picomolar levels and requires external glutamate and calcium (Dawson et al., 90(8):3256-3259, 1993). This toxicity can be attenuated by administration of a compound of the invention, either alone or in combination with another therapeutic agent, such as, for example, an NMDA antagonist.

Examples of NMDA antagonist useful for any of the combinations of the invention include aptiganel; besonprodil; budipine; conantokin G; delucemine; dexanabinol; felbamate; fluorofelbamate; gacyclidine; glycine; ipenoxazone; kaitocephalin; lanicemine; licostinel; midafotel; milnacipran; neramexane; orphenadrine; remacemide; topiramate; (αR)-α-amino-5-chloro-1-(phosphonomethyl)-1H-benzimidazole-2-propanoic acid; 1-aminocyclopentane-carboxylic acid; [5-(aminomethyl)-2-[[[(5S)-9-chloro-2,3,6,7-tetrahydro-2,3-dioxo-1H-,5H-pyrido[1,2,3-de]quinoxalin-5-yl] acetyl]amino]phenoxy]-acetic acid; α-amino-2-(2-phosphonoethyl)-cyclohexanepropanoic acid; α-amino-4-(phosphonomethyl)-benzeneacetic acid; (3E)-amino-4-(phosphonomethyl)-3-heptenoic acid; 3-[(1E)-2-carboxy-2-phenylethenyl]-4,6-dichloro-1H-indole-2-carboxylic acid; 8-chloro-2,3-dihydropyridazino[4,5-b]quinoline-1,4-dione 5-oxide salt with 2-hydroxy-N,N,N-trimethyl-ethanaminium; N'-[2-chloro-5-(methylthio)phenyl]-N-methyl-N-[3-(methylthio)phenyl]-guanidine; N'-[2-chloro-5-(methylthio)phenyl]-N-methyl-N-[3-[(R)-methylsulfinyl]phenyl]-guanidine; 6-chloro-2,3,4,9-tetrahydro-9-methyl-2,3-dioxo-1H-indeno[1,2-b]pyrazine-9-acetic acid; 7-chlorothiokynurenic acid; (3S,4aR,6S,8aR)-decahydro-6-(phosphonomethyl)-3-isoquinolinecarboxylic acid; (−)-6,7-dichloro-1,4-dihydro-5-[3-(methoxymethyl)-5-(3-pyridinyl)-4-H-1,2,4-triazol-4-yl]-2,3-quinoxalinedione; 4,6-dichloro-3-[(E)-(2-oxo-1-phenyl-3-pyrrolidinylidene) methyl]-1H-indole-2-carboxylic acid; (2R,4S)-rel-5,7-dichloro-1,2,3,4-tetrahydro-4-[[[(phenylamino)carbonyl] amino]-2-quinolinecarboxylic acid; (3R,4S)-rel-3,4-dihydro-3-[4-hydroxy-4-(phenylmethyl)-1-piperidinyl-]-2H-1-benzopyran-4,7-diol; 2-[(2,3-dihydro-1H-inden-2-yl) amino]-acetamide; 1,4-dihydro-6-methyl-5-[(methylamino) methyl]-7-nitro-2,3-quinoxalinedione; [2-(8,9-dioxo-2,6-diazabicyclo[5.2.0]non-1 (7)-en-2-yl)ethyl]-phosphonic acid; (2R,6S)-1,2,3,4,5,6-hexahydro-3-[(2S)-2-methoxypropyl]-6,11,11-trimethyl-2,6-methano-3-benzazocin-9-ol; 2-hydroxy-5-[[(pentafluorophenyl)methyl]amino]-benzoic acid; 1-[2-(4-hydroxyphenoxy)ethyl]-4-[(4-methylphenyl) methyl]-4-piperidinol; 1-[4-(1H-imidazol-4-yl)-3-butynyl]-4-(phenylmethyl)-piperidine; 2-methyl-6-(phenylethynyl)-pyridine; 3-(phosphonomethyl)-L-phenylalanine; and 3,6,7-tetrahydro-2,3-dioxo-N-phenyl-1H,5H-pyrido[1,2,3-de] quinoxaline-5-acetamide or those described in U.S. Pat. Nos. 6,071,966; 6,034,134; and 5,061,703.

(10) Cardiogenic Shock

Cardiogenic shock (CS) is the leading cause of death for patients with acute myocardial infarction that is consistent with increased levels of NO and inflammatory cytokines. High levels of NO and peroxynitrite have many effects, including a direct inhibition on myocardial contractability, suppression of mitochondrial respiration in myocardium, alteration in glucose metabolism, reduced catacholamine responsivity, and induction of systemic vasodilation (Hochman, *Circulation* 107:2998, 2003). In a clinical study in 11 patients with persistent shock, administration of the NOS inhibitor L-NMMA resulted in increases in urine output and blood pressure and survival rate of 72% up to 30 days (Cotter et al., *Circulation* 101:1258-1361, 2000). In a randomized trial of 30 patients, it was reported that L-NAME reduced patient mortality from 67% to 27% (Cotter et al., *Eur. Heart. J.* 24(14):1287-95, 2003). Similarly, administration of a compound of the invention, either alone or in combination with another therapeutic agent, may be useful for the treatment of cardiogenic shock.

(11) Anxiety and Depression

Recent studies of rats and mice in the forced swimming test (FST) indicate that NOS inhibitors have antidepressant activity in mice (Harkin et al. *Eur. J. Pharm.* 372:207-213, 1999) and that their effect is mediated by a serotonin dependent mechanism (Harkin et al., *Neuropharmacology* 44(5):616-623, 1993). 7-NI demonstrates anxiolytic activity in the rat plus-maze test (Yildiz et al., *Pharmacology, Biochemistry and Behavior* 65:199-202, 2000), whereas the selective nNOS inhibitor TRIM is effective in both the FST model of depression and anxiety in the light-dark compartment test (Volke et al., *Behavioral Brain Research* 140(1-2):141-7, 2003). Administration of a compound of the invention to an afflicted individual, either alone or in combination with another therapeutic agent, such as, for example, an antidepressant, may be useful for the treatment of anxiety or depression.

(12) Attention Deficit Hyperactivity Disorder

Non-selective attention (NSA) to environmental stimuli in Spontaneously Hypertensive (SHR) and Naples Low-Excitability (NHE) rats has been used as an animal model of Attention-Deficit Hyperactivity Disorder (ADHD) (Aspide et al., *Behav. Brain Res.* 95(1):23-33, 1998). These genetically altered animals show increased episodes of rearing that have a shorter duration than observed in normal animals. A single injection of L-NAME at 10 mg/kg produced an increase in rearing duration. Similarly, using the more neuronally selective 7-NINA, an increase in the rearing duration was observed after rapid administration (i.p.), while a slow release single release dose or a slow multiple release dose (s.c. in DMSO) resulted in the opposite effect. Thus, administration of a compound of the invention may be useful for the treatment of ADHD.

(13) Psychosis

Phencyclidine (PCP) is a non-competitive NMDA channel blocker that produces behavioral side effects in human and mammals consistent with those observed in patients with psychosis. In two animal models of psychosis, the nNOS selective inhibitor AR-R17477 antagonized PCP-induced hyperlocomotion and PCP-induced deficit in prepulse inhibition of the acoustic response startle (Johansson et al., *Pharmacol Toxicol*. 84(5):226-33, 1999). These results suggest the involvement of nNOS in psychosis. Therefore, administration of a compound of the invention to an afflicted individual may be useful for the treatment of this or related diseases or disorders.

(14) Head Trauma

The mechanism of neurological damage in patients with head trauma parallels that of stroke and is related to excitotoxic calcium influx from excessive glutamate release, oxidative stress and free radical production from mitochondrial dysfunction and inflammation (*Drug & Market Development* 9(3):60-63, 1998). Animals treated with nitric oxide synthase inhibitors, such as 7-NI and 3-bromo-7-nitroindazole, have shown an improvement in neurological deficits after experimental traumatic brain injury (TBI) (Mesenge et al., *J. Neurotrauma* 13:209-14, 1996). Administration of a compound of the invention to an afflicted individual may also be useful for the treatment of neurological damage in head trauma injuries.

(15) Hypothermic Cardiac Arrest

Hypothermic cardiac arrest (HCA) is a technique used to protect from ischemic damage during cardiac surgery when the brain is sensitive to damage during the period of blood flow interruption. Various neuroprotective agents have been used as adjunct agents during HCA and reducing nitric oxide production during HCA is predicted to result in improvements in neurological function. This is based on previous studies that showed glutamate excitotoxicity plays a role in HCA-induced neurologic damage (Redmond et al., *J. Thorac. Cardiovasc. Surg.* 107:776-87, 1994; Redmond et al., *Ann. Thorac. Surg.* 59:579-84, 1995) and that NO mediates glutamate excitotoxicity (Dawson and Snyder, *J. Neurosci.* 14:5147-59, 1994). In a study of 32 dogs undergoing 2 hours of HCA at 18° C., a neuronal NOS inhibitor was shown to reduce cerebral NO production, significantly reduce neuronal necrosis, and resulted in superior neurologic function relative to controls (Tseng et al., *Ann. Thorac. Surg.* 67:65-71, 1999). Administration of a compound of the invention may also be useful for protecting patients from ischemic damage during cardiac surgery.

(16) Neurotoxicity and Neurodegenerative Diseases

Mitochondrial dysfunction, glutamate excitotoxicity, and free radical induced oxidative damage appear to be the underlying pathogenesis of many neurodegenerative diseases, including amyotrophic lateral sclerosis (ALS), Parkinson's disease (PD), Alzheimer's disease (AD), and Huntington's disease (HD) (Schulz et al., *Mol. Cell. Biochem.* 174(1-2): 193-197, 1997; Beal, *Ann. Neurol.* 38:357-366, 1995), and NO is a primary mediator in these mechanisms. For example, it was shown by Dawson et al., in PNAS 88(14):6368-6371, 1991, that NOS inhibitors like 7-NI and L-NAME prevent neurotoxicity elicited by N-methyl-D-aspartate and related excitatory amino acids.

(a) Parkinson's Disease

Studies have also shown that NO plays an important role in 1-methyl-4-phenyl-1,2,3,6-tetrahydropyridine (MPTP) neurotoxicity, a commonly used animal model of Parkinson's disease (Matthews et al., *Neurobiology of Disease* 4:114-121, 1997). MPTP is converted to MPP+ by MAO-B and is rapidly taken up by the dopamine transporter into the mitochondria of dopamine containing neurons with subsequent activation of nNOS resulting in neuronal death. Mutant mice lacking the nNOS gene, but not the eNOS gene, have reduced lesions in the substantia nigra after MPP+ injection into the striatum. In primate studies, 7-NI exerts a profound neuroprotective and antiparkinsonium effect after MPTP challenge (Hantraye et al., *Nature Med.* 2:1017-1021, 1996) as did the non-specific inhibitor L-NAME (T. S. Smith et. al. Neuroreport 1994, 5, 2598-2600).

(b) Alzheimer's Disease (AD)

The pathology of AD is associated with β-amyloid plaques infiltrated with activated microglia and astrocytes. When cultured rat microglia are exposed to beta-amyloid, there is a prominent microglial release of nitric oxide, especially in the presence of gamma-interferon (Goodwin et al., *Brain Research* 692(1-2):207-14, 1995). In cortical neuronal cultures, treatment with nitric oxide synthase inhibitors provides neuroprotection against toxicity elicited by human beta-amyloid (Resink et al., *Neurosci. Abstr.* 21:1010, 1995). Consistent with the glutamate hypothesis of excitoxicity in neurodegerative disorders, the weak NMDA antagonist amantadine increases the life expectancy of PD patients (Uitti et al., *Neurology* 46(6):1551-6, 1996). In a preliminary, placebocontrolled study of patients with vascular- or Alzheimer's-type dementia, the NMDA antagonist memantine was associated with improved Clinical Global Impression of Change and Behavioral Rating Scale for Geriatric Patients scores (Winblad and Poritis, *Int. J. Geriatr. Psychiatry* 14:135-46, 1999).

(c) Amyotrophic Lateral Sclerosis

Amyotrophic lateral sclerosis (ALS) is a fatal neurodegenerative disease characterized by selective motor neuronal death. Accumulating evidence suggests that the pathogenesis of ALS is the insufficient clearance of glutamate through the glutamate transporter, and the specific distribution of $Ca^{2+}$-permeable AMPA receptors in spinal motor neurons, indicates a glutamate-induced neurotoxicity. Increased nNOS immunoreactivity is found in the spinal cords (Sasaki et al., *Acta Neuropathol. (Berl)* 101(4):351-7, 2001) and glial cells (Anneser et al., *Exp. Neurol* 171(2):418-21, 2001) of ALS patients, implicating NO as an important factor in the pathogenesis of ALS.

(d) Huntington's Disease

The pathogenesis of Huntington's disease (HD) arising from a mutation in the Htt protein is linked to excitotoxicity, oxidative stress and apoptosis, in all of which excessive NO has a clear role (Peterson et al., *Exp. Neurol.* 157:1-18, 1999). Oxidative damage is one of the major consequences of defects in energy metabolism and is present in HD models after injection of excitotoxins and mitochondrial inhibitors (A. Petersen et. al., *Exp. Neurol.* 157:1-18, 1999). This mitochrondrial dysfunction is associated with the selective and progressive neuronal loss in HD (Brown et al., *Ann. Neurol* 41:646-653, 1997). NO can directly impair the mitochondrial respiratory chain complex IV (Calabrese et al., *Neurochem. Res.* 25:1215-41, 2000). Striatal medium spiny neurons appear to be the primary target for the generation of motor dysfunction in HD. Hyperphosphorylation and activation of NMDA receptors on these neurons likely participates in the generation of motor dysfunction. It has been shown clinically that the NMDA antagonist amantadine improve choreiform dyskinesias in HD (Verhagen Metman et al., *Neurology* 59:694-699, 2002). Given the role of nNOS in NMDA mediated neurotoxicity, it is expected that nNOS inhibitors, especially those with mixed nNOS/NMDA, or combinations of drugs with nNOS and NMDA activity will also be useful in ameliorating the effects and or progression of HD. For example, pretreatment of rats with 7-nitroindazole attenuates the striatal lesions elicited by stereotaxic injections of malonate, an injury that leads to a condition resembling Huntington's disease (Hobbs et. al., *Ann. Rev. Pharm. Tox.* 39:191-220, 1999). In a R6/1 transgenic mouse model of HD expressing a human mutated htt exon1, a 116 CAG repeat, mice at 11, 19 and 35 weeks show a progressive increase in lipid peroxidation with normal levels of superoxide dismutase (SOD) at 11 weeks similar to wild type (WT) mice; a maximum level at 19 weeks, above that observed in WT mice and corresponding to the early phase of disease progression; and finally, decreasing levels at 35 weeks below that observed in WT mice (Pérez-Sevriano et al., *Brain Res.* 951:36-42, 2002). The increase in SOD activity is attributable to a compensatory neuroprotective mechanism, with decreased levels at 35 weeks corresponding to a failed protective mechanism. Concomitant with the levels of SOD, levels of calcium dependent NOS was the same for 11 week mice in both WT and R6/1 mice, but increased significantly at 19 weeks and decreased at 35 weeks relative to WT control mice. Levels of nNOS expression also increased dramatically relative to controls at 19 weeks but were decreased significantly relative to controls at 35 weeks. No significant differences were observed in levels of eNOS expression, nor could iNOS protein be detected during progression of the disease. The progressive phenotypic expression of the disease, as measured by increased weight loss, feet clasping behavior, and horizontal and vertical movements, are consistent with changes in NOS activity and nNOS expression. Finally, the effects of L-NAME administration to both R6/2 transgenic HD mice and WT mice showed improved levels of clasping behavior at a 10 mg/kg dose similar to controls, which worsened at the highest dose of 500 mg/kg (Deckel et al., *Brain Res.* 919 (1):70-81, 2001). An improvement in weight increase in HD mice was also significant at the 10 mg/kg dose, but decreased relative to controls at high dose levels of L-NAME. These results demonstrate that administration of an appropriate dose of an NOS inhibitor, such as, for example, a compound of the invention, can be beneficial in the treatment of HD.

(e) Multiple Sclerosis (MS)

MS is in an inflammatory demyelinating disease of the CNS involving cytokines and other inflammatory mediators. Many studies suggest that NO and its reactive derivative peroxynitrite are implicated in the pathogenesis of MS (Acar et al. *J. Neurol.* 250(5):588-92, 2003; Calabrese et al., *Neurochem. Res.* 28(9):1321-8, 2003). In experimental autoimmune encephalomyelitis (EAE), a model of MS, nNOS levels are slightly increased in the spinal cord of EAE rats and treatment with 7-nitroindazole results in a significant delay in the onset of EAE paralysis (Shin, *J. Vet. Sci.* 2(3):195-9, 2001).

(f) Methamphetamine-Induced Neurotoxicity

Methamphetamine is neurotoxic by destroying dopamine nerve terminals in vivo. It has been shown that methamphetamine-induced neurotoxicity can be attenuated by treatment with NOS inhibitors in vitro (Sheng et al., *Ann. N.Y. Acad. Sci.* 801:174-186, 1996) and in in vivo animal models (Itzhak et al., *Neuroreport* 11(13):2943-6, 2000). Similary, the nNOS selective inhibitor AR-17477AR, at 5 mg/kg s.c in mice, was able to prevent the methamphetamine-induced loss of the neurofilament protein NF68 in mouse brain and prevent the loss of striaital dopamine and homovanillic acid (HVA) (Sanchez et al., *J. Neurochem.* 85(2):515-524, 2003).

Administration of a compound of the invention, either alone or in combination with another therapeutic agent, such as, for example, an NMDA antagonist, may be useful for the protection or treatment of any of the neurodegenerative diseases described herein. Further, the compounds of the invention may be tested in standard assays used to assess neuroprotection (see for example, *Am. J. Physiol.* 268:R286, 1995).

(17) Chemical Dependencies and Drug Addictions (e.g., Dependencies on Drugs, Alcohol and Nicotine)

A key step in the process of drug-induced reward and dependence is the regulation of dopamine release from mesolimbic dopaminergic neurons. Chronic application of cocaine alters the expression of the key protein controlling the synaptic level of dopamine—the dopamine transporter (DAT).

(a) Cocaine Addiction

Studies have shown that animals reliably self-administer stimulants intravenously and that dopamine is critical in their reinforcing effects. Recently NO containing neurons have been shown to co-localize with dopamine in areas of the striatum and ventral tegmental area and that NO can modulate stimulant-evoked dopamine (DA) release. Administration of dopamine D1 receptor antagonists decrease the levels of straital NADPH-diaphorase staining, a marker for NOS activity, while D2 antagonists produce the opposite effect. L-Arginine, the substrate of NOS, is also a potent modulator of DA release. Also, multiple NO-generating agents increase DA efflux or inhibit reuptake both in vitro and in vivo. L-NAME has been shown to significantly alter cocaine reinforcement by decreasing the amount of self-administration and by increasing the inter-response time between successive cocaine injections (Pudiak and Bozarth, *Soc. Neurosci. Abs.* 22:703, 1996). This indicates that NOS inhibition may be useful in the treatment of cocaine addiction.

(b) Morphine/Opioid Induced Tolerance and Withdrawal Symptoms

There is much evidence supporting the role of both the NMDA and NO pathways in opioid dependence in adult and infant animals. Adult or neonatal rodents injected with morphine sulfate develop behavioral withdrawal after precipitation with naltrexone. The withdrawal symptoms after naltrexone initiation can be reduced by administration of NOS inhibitors, such as 7-NI or L-NAME (Zhu and Barr, *Psychopharmacology* 150(3):325-336, 2000). In a related study, it was shown that the more nNOS selective inhibitor 7-NI attenuated more of the morphine induced withdrawal symptoms including mastication, salivation and genital effects than the less selective compounds (Vaupel et al., *Psychopharmacology (Berl.)* 118(4):361-8, 1995).

(c) Ethanol Tolerance and Dependence

Among the factors that influence alcohol dependence, tolerance to the effects of ethanol is an important component because it favors the exaggerated drinking of alcoholic beverages (Le and Kiianmaa, *Psychopharmacology (Berl.)* 94:479-483, 1988). In a study with rats, ethanol tolerance to motor incoordination and hypothermia develop rapidly and can be blocked by i.c.v administration of 7-NI without altering cerebral ethanol concentrations (Wazlawik and Morato, *Brain Res. Bull.* 57(2):165-70, 2002). In other studies, NOS inhibition with L-NAME (Rezvani et al., *Pharmacol. Biochem. Behav.* 50:265-270, 1995) or by i.c.v. injection of nNOS antisense (Naassila et. al., Pharmacol. Biochem. Behav. 67:629-36, 2000) reduced ethanol consumption in these animals.

Administration of a compound of the invention, either alone or in combination with another therapeutic agent, such as, for example, an NMDA antagonist, may be useful for the treatment of chemical dependencies and drug addictions.

(18) Epilepsy

Co-administration of 7-NI with certain anticonvulsants, such as carbamazepine, shows a synergistic protective effect against amygdala-kindled seizures in rats at concentrations that do not alter roto-rod performance (Borowicz et al., *Epilepsia* 41(9):112-8, 2000). Thus, an NOS inhibitor, such as, for example, a compound of the invention, either alone or in combination with another therapeutic agent, such as, for example, an antiepileptic agent, may be useful for the treatment of epilepsy or a similar disorder. Examples of antiepileptic agents useful in a combination of the invention include carbamazepine, gabapentin, lamotrigine, oxcarbazepine, phenyloin, topiramate, and valproate.

(19) Diabetic Nephropathy

Urinary excretion of NO byproducts is increased in diabetic rats after streptozotocin treatment and increased NO synthesis has been suggested to be involved in diabetic glomerular hyperfiltration. The neuronal isoform nNOS is expressed in the loop of Henle and mucula densa of the kidney and inhibition of this isoform using 7-NI reduces glomerular filtration without affecting renal arteriole pressure or renal blood flow (Sigmon et al., *Gen. Pharmacol.* 34(2):95-100, 2000). Both the non-selective NOS inhibitor L-NAME and the nNOS selective 7-NI normalize renal hyperfiltration in diabetic animals (Ito et al., *J. Lab Clin. Med.* 138(3):177-185, 2001). Therefore, administration of a compound of the invention may be useful for the treatment of diabetic nephropathy.

Combination Formulations, and Uses Thereof

In addition to the formulations described above, one or more compounds of the invention can be used in combination with other therapeutic agents. For example, one or more compounds of the invention can be combined with another NOS inhibitor. Exemplary inhibitors useful for this purpose include, without limitation, those described in U.S. Pat. No. 6,235,747; U.S. patent application Ser. Nos. 09/127,158, 09/325,480, 09/403,177, 09/802,086, 09/826,132, 09/740, 385, 09/381,887, 10/476,958, 10/483,140, 10/484,960, 10/678,369, 10/819,853, 10/938,891; International Publication Nos. WO 97/36871, WO 98/24766, WO 98/34919, WO 99/10339, WO 99/11620, and WO 99/62883.

In another example, one or more compounds of the invention can be combined with an antiarrhythmic agent. Exemplary antiarrhythmic agents include, without limitation, lidocaine and mixiletine.

GABA-B agonists, alpha-2-adrenergic receptor agonists, cholecystokinin antagonists, $5HT_{1B/1D}$ agonists, or CGRP antagonists can also be used in combination with one or more compounds of the invention. Non-limiting examples of alpha-2-adrenergic receptor agonists include clonidine, lofexidine, and propanolol. Non-limiting examples of cholecystokinin antagonists include L-365,260; CI-988; LY262691; $SO_{509}$, or those described in U.S. Pat. No. 5,618,811. Non-limiting examples of $5HT_{1B/1D}$ agonists that may be used in combination with a compound of the invention include dihydroegotamine, eletriptan, frovatriptan, naratriptan, rizatriptan, sumatriptan, or zolmitriptan. Non-limiting examples of CGRP antagonists that may be used in combination with a compound of the invention include quinine analogues as described in International Publication No. WO9709046, non-peptide antagonists as described in International Publication Nos. WO0132648, WO0132649, WO9811128, WO9809630, WO9856779, WO0018764, or other antagonists such as SB-(+)-273779 or BIBN-4096BS.

Substance P antagonists, also known as $NK_1$ receptor antagonists, are also useful in combination with one or more compounds of the invention. Exemplary inhibitors useful for this purpose include, without limitation, those compounds disclosed in U.S. Pat. Nos. 3,862,114, 3,912,711, 4,472,305, 4,481,139, 4,680,283, 4,839,465, 5,102,667, 5,162,339, 5,164,372, 5,166,136, 5,232,929, 5,242,944, 5,300,648, 5,310,743, 5,338,845, 5,340,822, 5,378,803, 5,410,019, 5,411,971, 5,420,297, 5,422,354, 5,446,052, 5,451,586, 5,525,712, 5,527,811, 5,536,737, 5,541,195, 5,594,022, 5,561,113, 5,576,317, 5,604,247, 5,624,950, and 5,635,510; International Publication Nos. WO 90/05525, WO 91/09844, WO 91/12266, WO 92/06079, WO 92/12151, WO 92/15585, WO 92/20661, WO 92/20676, WO 92/21677, WO 92/22569, WO 93/00330, WO 93/00331, WO 93/01159, WO 93/01160, WO 93/01165, WO 93/01169, WO 93/01170, WO 93/06099, WO 93/10073, WO 93/14084, WO 93/19064, WO 93/21155, WO 94/04496, WO 94/08997, WO 94/29309, WO 95/11895, WO 95/14017, WO 97/19942, WO 97/24356, WO 97/38692, WO 98/02158, and WO 98/07694; European Patent Publication Nos. 284942, 327009, 333174, 336230, 360390, 394989, 428434, 429366, 443132, 446706, 484719, 499313, 512901, 512902, 514273, 514275, 515240, 520555, 522808, 528495, 532456, and 591040.

Suitable classes of antidepressant agents that may be used in combination with a compound of the invention include, without limitation, norepinephrine re-uptake inhibitors, selective serotonin re-uptake inhibitors (SSRIs), selective noradrenaline/norepinephrine reuptake inhibitors (NARIs), monoamine oxidase inhibitors (MAOs), reversible inhibitors of monoamine oxidase (RIMAs), dual serotonin/noradrenaline re-uptake inhibitors (SNRIs), α-adrenoreceptor antagonists, noradrenergic and specific serotonergic antidepressants (NaSSAs), and atypical antidepressants.

Non-limiting examples of norepinephrine re-uptake inhibitors include tertiary amine tricyclics and secondary amine tricyclics, such as, for example, adinazolam, amineptine, amitriptyline, amoxapine, butriptyline, clomipramine, demexiptiline, desmethylamitriptyline, desipramine, dibenzepin, dimetacrine, doxepin, dothiepin, femoxetine, fluacizine, imipramine, imipramine oxide, iprindole, lofepramine, maprotiline, melitracen, metapramine, norclolipramine, nortriptyline, noxiptilin, opipramol, perlapine, pizotifen, pizotyline, propizepine, protriptyline, quinupramine, tianeptine, trimipramine, trimipramineamiltriptylinoxide, and pharmaceutically acceptable salts thereof.

Non-limiting examples of selective serotonin re-uptake inhibitors include, for example, fluoxetine, fluvoxamine, paroxetine, and sertraline, and pharmaceutically acceptable salts thereof.

Non-limiting examples of selective noradrenaline/norepinephrine reuptake inhibitors include, for example, atomoxetine, bupropion; reboxetine, and tomoxetine.

Non-limiting examples of selective monoamine oxidase inhibitors include, for example, isocarboxazid, phenezine, tranylcypromine and selegiline, and pharmaceutically acceptable salts thereof. Other monoamine oxidase inhibitors useful in a combination of the invention include clorgyline, cimoxatone, befloxatone, brofaromine, bazinaprine, BW-616U (Burroughs Wellcome), BW-1370U87 (Burroughs Wellcome), CS-722 (RS-722) (Sankyo), E-2011 (Eisai), harmine, harmaline, moclobemide, PharmaProjects 3975 (Hoechst), RO 41-1049 (Roche), RS-8359 (Sankyo), T-794 (Tanabe Seiyaku), toloxatone, K-Y 1349 (Kalir and Youdim), LY-51641 (Lilly), LY-121768 (Lilly), M&B 9303 (May & Baker), MDL 72394 (Marion Merrell), MDL 72392 (Marion Merrell), sercloremine, and MO 1671, and pharmaceutically acceptable salts thereof. Suitable reversible inhibitors of monoamine oxidase that may be used in the present invention include, for example, moclobemide, and pharmaceutically acceptable salts thereof.

Non-limiting examples of dual serotonin/norepinephrine reuptake blockers include, for example, duloxetine, milnacipran, mirtazapine, nefazodone, and venlafaxine.

Non-limiting examples of other antidepressants that may be used in a method of the present invention include adinazolam, alaproclate, amineptine, amitriptyline/chlordiazepoxide combination, atipamezole, azamianserin, bazinaprine, befuraline, bifemelane, binodaline, bipenamol, brofaromine, caroxazone, cericlamine, cianopramine, cimoxatone, citalopram, clemeprol, clovoxamine, dazepinil, deanol, demexiptiline, dibenzepin, dothiepin, droxidopa, enefexine, estazolam, etoperidone, fengabine, fezolamine, fluotracen, idazoxan, indalpine, indeloxazine, levoprotiline, litoxetine; medifoxamine, metralindole, mianserin, minaprine, montirelin, nebracetam, nefopam, nialamide, nomifensine, norfluoxetine, orotirelin, oxaflozane, pinazepam, pirlindone, ritanserin, rolipram, sercloremine, setiptiline, sibutramine, sulbutiamine, sulpiride, teniloxazine, thozalinone, thymoliberin, tiflucarbine, tofenacin, tofisopam, toloxatone, veralipride, viqualine, zimelidine, and zometrapine, and pharmaceutically acceptable salts thereof, and St. John's wort herb, or Hypencuin perforatum, or extracts thereof.

In another example, opioids can be used in combination with one or more compounds of the invention. Exemplary opioids useful for this purpose include, without limitation, alfentanil, butorphanol, buprenorphine, dextromoramide, dezocine, dextropropoxyphene, codeine, dihydrocodeine, diphenoxylate, etorphine, fentanyl, hydrocodone, hydromorphone, ketobemidone, loperamide, levorphanol, levomethadone, meperidine, meptazinol, methadone, morphine, morphine-6-glucuronide, nalbuphine, naloxone, oxycodone, oxymorphone, pentazocine, pethidine, piritramide, propoxylphene, remifentanil, sulfentanyl, tilidine, and tramadol.

In yet another example, anti-inflammatory compounds, such as steroidal agents or non-steroidal anti-inflammatory drugs (NSAIDs), can be used in combination with one or more compounds of the invention. Non-limiting examples of steroidal agents include prednisolone and cortisone. Non-limiting examples of NSAIDs include acemetacin, aspirin, celecoxib, deracoxib, diclofenac, diflunisal, ethenzamide, etofenamate, etoricoxib, fenoprofen, flufenamic acid, flurbiprofen, lonazolac, lornoxicam, ibuprofen, indomethacin, isoxicam, kebuzone, ketoprofen, ketorolac, naproxen, nabumetone, niflumic acid, sulindac, tolmetin, piroxicam, meclofenamic acid, mefenamic acid, meloxicam, metamizol, mofebutazone, oxyphenbutazone, parecoxib, phenidine, phenylbutazone, piroxicam, propacetamol, propyphenazone, rofecoxib, salicylamide, suprofen, tiaprofenic acid, tenoxicam, valdecoxib, 4-(4-cyclohexyl-2-methyloxazol-5-yl)-2-fluorobenzenesulfonamide, N-[2-(cyclohexyloxy)-4-nitrophenyl]methanesulfonamide, 2-(3,4-difluorophenyl)-4-(3-hydroxy-3-methylbutoxy)-5-[4-(methylsulfonyl)phenyl]-3 (2H)-pyridazinone, and 2-(3,5-difluorophenyl)-3-[4-(methylsulfonyl)phenyl]-2-cyclopenten-1-one). Compounds of the invention may also be use in combination with acetaminophen.

Any of the above combinations can be used to treat any appropriate disease, disorder, or condition. Exemplary uses for combinations of a compound of the invention and another therapeutic agent are described below.

(1) Opioid-NOS Inhibitor Combinations in Chronic, Neuropathic Pain

Nerve injury can lead to abnormal pain states known as neuropathic pain. Some of the clinical symptoms include tactile allodynia (nociceptive responses to normally innocuous mechanical stimuli), hyperalgesia (augmented pain intensity in response to normally painful stimuli), and spontaneous pain. Spinal nerve ligation (SNL) in rats is an animal model of neuropathic pain that produces spontaneous pain, allodynia, and hyperalgesia, analogous to the clinical symptoms observed in human patients (Kim and Chung, *Pain* 50:355-363, 1992; Seltzer, *Neurosciences* 7:211-219, 1995).

Neuropathic pain can be particularly insensitive to opioid treatment (Benedetti et al., *Pain* 74:205-211, 1998) and is still considered to be relatively refractory to opioid analgesics (MacFarlane et al., *Pharmacol. Ther.* 75:1-19, 1997; Watson, *Clin. J. Pain* 16:S49-S55, 2000). While dose escalation can overcome reduced opioid effectiveness, it is limited by increased side effects and tolerance. Morphine administration is known to activate the NOS system, which limits the analgesic action of this drug (Machelska et al., *NeuroReport* 8:2743-2747, 1997; Wong et al., *Br. J. Anaesth.* 85:587, 2000; Xiangqi and Clark, *Mol. Brain. Res.* 95:96-102, 2001). However, it has been shown that the combined systemic administration of morphine and L-NAME can attenuate mechanical and cold allodynia at subthreshold doses at which neither drug administered alone was effective (Ulugol et al., *Neurosci. Res. Com.* 30(3):143-153, 2002). The effect of L-NAME co-administration on morphine analgesia appears to be mediated by nNOS, as L-NAME loses its ability to potentiate morphine analgesia in nNOS null-mutant mice (Clark and Xiangqi, *Mol. Brain. Res.* 95:96-102, 2001). Enhanced analgesia has been demonstrated in the tail-flick or paw pressure models using coadministration of L-NAME or 7-NI with either a mu-, delta-, or kappa-selective opioid agonist (Machelska et al., *J. Pharmacol. Exp. Ther.* 282:977-984, 1997).

While opioids are an important therapy for the treatment of moderate to severe pain, in addition to the usual side effects that limit their utility, the somewhat paradoxical appearance of opioid-induced hyperalgesia may actually render paitents more sensitive to pain and potentially aggravate their pain (Angst and Clark, Anesthesiology, 2006, 104(3), 570-587; Chu et. al. J. Pain 2006, 7(1) 43-48). The development of tolerance and opioid induced hyperalgesia is consistent with increased levels of NO production in the brain. The reduced analgesic response to opioids is due to an NO-induced upregulated hyperalgesic response (Heinzen and Pollack, Brain Res. 2004, 1023, 175-184).

Thus, the combination of an nNOS inhibitor with an opioid (for example, those combinations described above) can enhance opioid analgesia in neuropathic pain and prevent the development of opioid tolerance and opioid-induced hyperalgesia.

(2) Antidepressant-NOS Inhibitor Combinations for Chronic Pain, Neuropathic Pain, Chronic Headache or Migraine Many antidepressants are used for the treatment of neuropathic pain (McQuay et al., *Pain* 68:217-227, 1996) and migraine (Tomkins et al., *Am. J. Med.* 111:54-63, 2001), and act via the serotonergic or noradrenergic system. NO serves as a neuromodulator of these systems (Garthwaite and Boulton, *Annu. Rev. Physiol.* 57:683, 1995). 7-NI has been shown to potentiate the release of noradrenaline (NA) by the nicotinic acetylcholine receptor agonist DMPP via the NA transporter (Kiss et al., *Neuroscience Lett.* 215:115-118, 1996). It has been shown that local administration of antidepressants, such as paroxetine, tianeptine, and imipramine decrease levels of hippocampal NO (Wegener et al., *Brain Res.* 959:128-134, 2003). It is likely that NO is important in the mechanism by which antidepressants are effective for treating pain and depression, and that a combination of an nNOS inhibitor with an antidepressant, such as, for example, those combinations described above, will produce better treatments.

(3) Serotonin $5HT_{1B/1D/1F}$ Agonist or CGRP Antagonist and NOS Inhibitor Combinations in Migraine Administration of Glyceryl trinitrate (GTN), an NO donor, induces immediate headaches in normal individuals and results in delayed migraine attacks in migraineurs with a 4-6 hour latency period (Iversen et al., *Pain* 38:17-24, 1989). In patients with migraine attack, levels of CGRP (Calcitonin Gene Related Peptide), a potent vasodialator, in the carotid artery correlate with the onset and ablation of migraine attack (Durham, *Curr Opin Investig Drugs* 5(7):731-5, 2004). Sumatriptan, an antimigraine drug having affinity at $5HT_{1B}$, $5HT_{1D}$, and $5HT_{1F}$ receptors, reduces GTN-induced immediate headache and in parallel contracts cerebral and extracerebral arteries (Iversen and Olesen, *Cephalagia* 13(Suppl 13):186, 1993). The antimigraine drug rizatriptan also reduces plasma levels of CGRP following migraine pain reduction (Stepien et al., *Neurol. Neurochir. Pol.* 37(5):1013-23, 2003). Both NO and CGRP have therefore been implicated as a cause for migraine. Serotonin $5HT_{1B/1D}$ agonists have been shown to block NMDA receptor-evoked NO signaling in brain cortex slices (Strosznajder et al., Cephalalgia 19(10):859, 1999). These results suggest that a combination of a compound of the invention and a selective or non-selective $5HT_{1B/1D/1F}$ agonist or a CGRP antagonist, such as those combinations described above, would be useful for the treatment of migraine.

Pharmaceutical Compositions

The compounds of the invention are preferably formulated into pharmaceutical compositions for administration to human subjects in a biologically compatible form suitable for administration in vivo. Accordingly, in another aspect, the present invention provides a pharmaceutical composition comprising a compound of the invention in admixture with a suitable diluent or carrier.

The compounds of the invention may be used in the form of the free base, in the form of salts, solvates, and as prodrugs. All forms are within the scope of the invention. In accordance with the methods of the invention, the described compounds or salts, solvates, or prodrugs thereof may be administered to a patient in a variety of forms depending on the selected route of administration, as will be understood by those skilled in the art. The compounds of the invention may be administered, for example, by oral, parenteral, buccal, sublingual, nasal, rectal, patch, pump, or transdermal administration and the pharmaceutical compositions formulated accordingly. Parenteral administration includes intravenous, intraperitoneal, subcutaneous, intramuscular, transepithelial, nasal, intrapulmonary, intrathecal, rectal, and topical modes of administration. Parenteral administration may be by continuous infusion over a selected period of time.

A compound of the invention may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, a compound of the invention may be incorporated with an excipient and used in the form of ingestible tablets, buccal tablets, troches, capsules, elixirs, suspensions, syrups, wafers, and the like.

A compound of the invention may also be administered parenterally. Solutions of a compound of the invention can be prepared in water suitably mixed with a surfactant, such as hydroxypropylcellulose. Dispersions can also be prepared in glycerol, liquid polyethylene glycols, DMSO and mixtures thereof with or without alcohol, and in oils. Under ordinary conditions of storage and use, these preparations may contain a preservative to prevent the growth of microorganisms. Conventional procedures and ingredients for the selection and preparation of suitable formulations are described, for example, in Remington's Pharmaceutical Sciences (2003-20th edition) and in The United States Pharmacopeia: The National Formulary (USP 24 NF19), published in 1999.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that may be easily administered via syringe.

Compositions for nasal administration may conveniently be formulated as aerosols, drops, gels, and powders. Aerosol formulations typically include a solution or fine suspension of the active substance in a physiologically acceptable aqueous or non-aqueous solvent and are usually presented in single or multidose quantities in sterile form in a sealed container, which can take the form of a cartridge or refill for use with an atomizing device. Alternatively, the sealed container may be a unitary dispensing device, such as a single dose nasal inhaler or an aerosol dispenser fitted with a metering valve which is intended for disposal after use. Where the dosage form comprises an aerosol dispenser, it will contain a propellant, which can be a compressed gas, such as compressed air or an organic propellant, such as fluorochlorohydrocarbon. The aerosol dosage forms can also take the form of a pump-atomizer.

Compositions suitable for buccal or sublingual administration include tablets, lozenges, and pastilles, where the active ingredient is formulated with a carrier, such as sugar, acacia, tragacanth, or gelatin and glycerine. Compositions for rectal administration are conveniently in the form of suppositories containing a conventional suppository base, such as cocoa butter.

The compounds of the invention may be administered to an animal alone or in combination with pharmaceutically acceptable carriers, as noted above, the proportion of which is determined by the solubility and chemical nature of the compound, chosen route of administration, and standard pharmaceutical practice.

The dosage of the compounds of the invention, and/or compositions comprising a compound of the invention, can vary depending on many factors, such as the pharmacodynamic properties of the compound; the mode of administration; the age, health, and weight of the recipient; the nature and extent of the symptoms; the frequency of the treatment, and the type of concurrent treatment, if any; and the clearance rate of the compound in the animal to be treated. One of skill in the art can determine the appropriate dosage based on the above factors. The compounds of the invention may be administered initially in a suitable dosage that may be adjusted as required, depending on the clinical response. In general, satisfactory results may be obtained when the compounds of the invention are administered to a human at a daily dosage of between 0.05 mg and 3000 mg (measured as the solid form). A preferred dose ranges between 0.05-500 mg/kg, more preferably between 0.5-50 mg/kg.

A compound of the invention can be used alone or in combination with other agents that have NOS activity, or in combination with other types of treatment (which may or may not inhibit NOS) to treat, prevent, and/or reduce the risk of stroke, neuropathic or migraine pain, or other disorders that benefit from NOS inhibition. In combination treatments, the dosages of one or more of the therapeutic compounds may be reduced from standard dosages when administered alone. In this case, dosages of the compounds when combined should provide a therapeutic effect.

In addition to the above-mentioned therapeutic uses, a compound of the invention can also be used in diagnostic assays, screening assays, and as a research tool.

In diagnostic assays, a compound of the invention may be useful in identifying or detecting NOS activity. For such a use, the compound may be radiolabelled (as described elsewhere herein) and contacted with a population of cells of an organism. The presence of the radiolabel on the cells may indicate NOS activity.

In screening assays, a compound of the invention may be used to identify other compounds that inhibit NOS, for example, as first generation drugs. As research tools, the compounds of the invention may be used in enzyme assays and assays to study the localization of NOS activity. Such information may be useful, for example, for diagnosing or monitoring disease states or progression. In such assays, a compound of the invention may also be radiolabeled.

The following non-limiting examples are illustrative of the present invention:

Example 1

Preparation of the Compounds of Formula 10-16

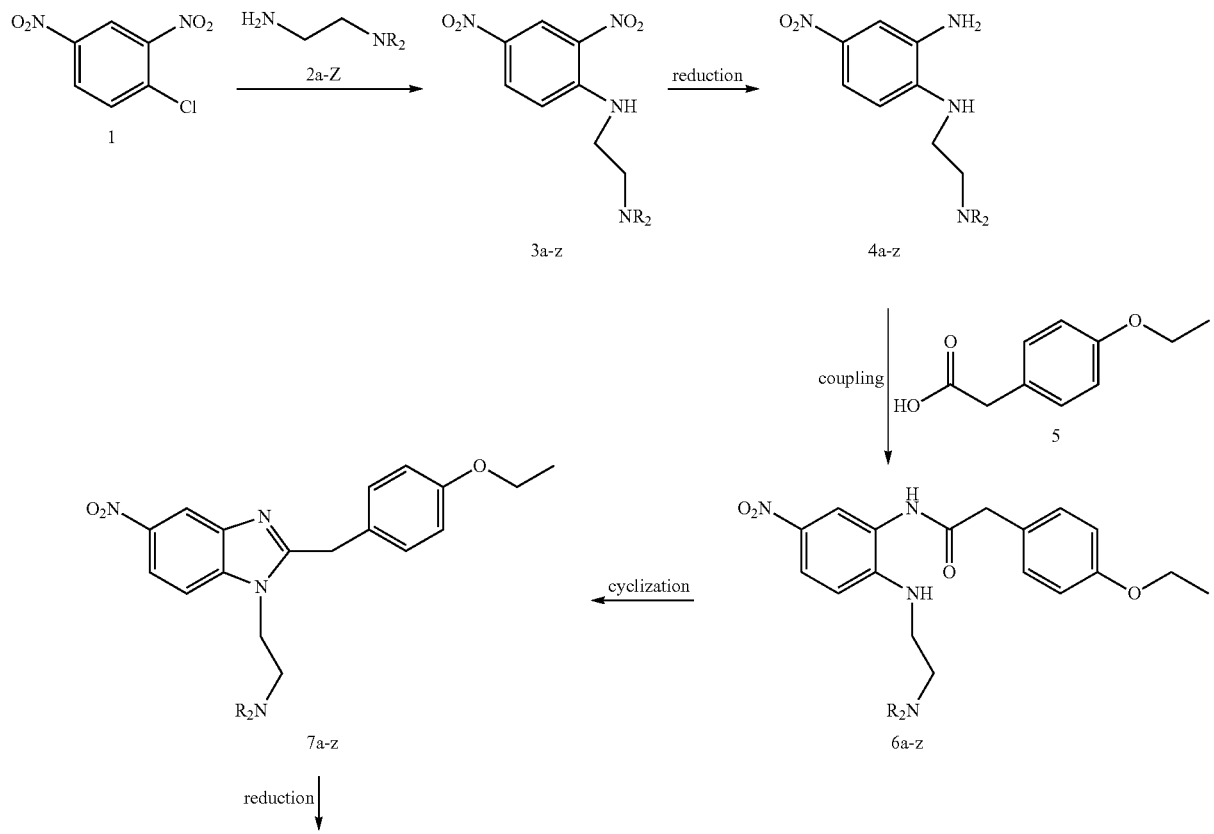

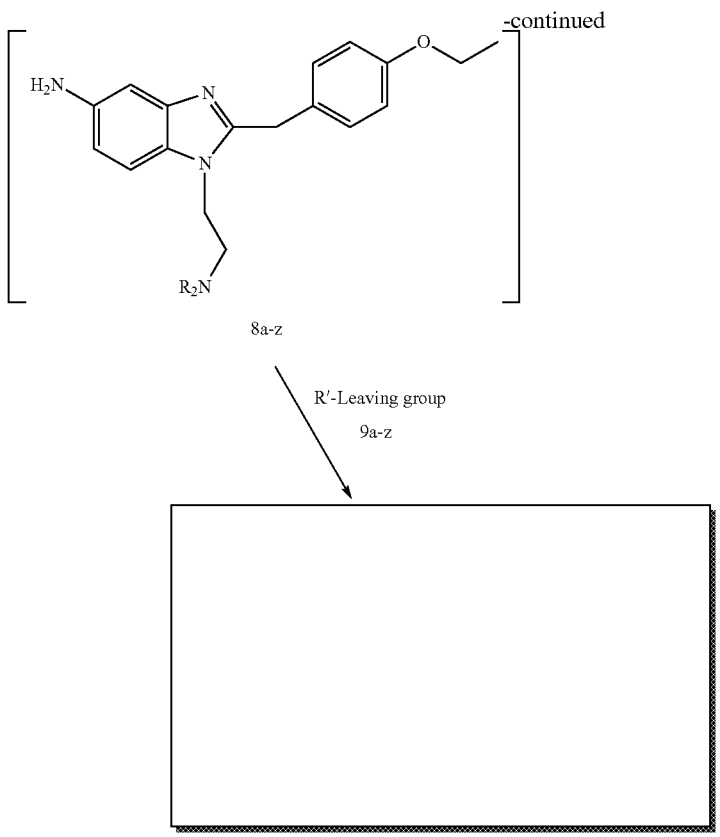

8a-z

↓ R'-Leaving group
9a-z

Preparation of 3a-z: Chloro-2,4-dinitrobenzene 1 (1.00 g, 4.937 mmol) was dissolved in anhydrous EtOH (20 mL) in a small argon purged flask and warmed in an oil bath to 40° C. Addition of N,N-diethylethylenediamine 2a (0.63 g, 5.430 mmol) occurred dropwise. The reaction was stirred at reflux for 24 hours then cooled to room temperature. The mixture was basified by the addition of aqueous 1M ammonium hydroxide solution to adjust pH to 10-11. The solid that precipitated was collected on a sintered glass funnel and briefly dried. Recrystallization of the crude solid from EtOH yielded a yellow powder 3a N'-(2,4-Dinitro-phenyl)-N,N-diethyl-ethane-1,2-diamine. Yield: 0.94 grams (67.4%). $^1$H NMR (DMSO) δ: 0.99 (t, 6H, J=7.1), 2.56 (m, 4H), 2.70 (t, 2H, J=6.1), 3.49 (q, 2H, J=5.5), 7.19 (d, 1H, J=9.7), 8.28 (dd, 1H, J=9.5, 2.6), 8.67 (d, 1H), 9.05 (br s, 1H); MS (APCI): 283 (MH$^+$, 100%)

In a like manner, utilizing N,N-dimethylethylenediamine 2b, compound 3b N'-(2,4-Dinitro-phenyl)-N,N-dimethyl-ethane-1,2-diamine was prepared. Yield: 760 mg (60.4%). $^1$H NMR (dmso) δ: 2.24 (s, 6H), 2.57 (t, 2H, J=6.1), 3.53 (q, 2H, J=6.0), 7.21 (d, 1H, J=9.6), 8.29 (dd, 1H, J=9.6, 2.7), 8.87 (d, 1H, J=2.7), 8.94 (br s, 1H); MS (ESI): 255 (MH$^+$, 100%)

Preparation of 4a-z: N'-(2,4-Dinitro-phenyl)-N,N-diethyl-ethane-1,2-diamine 3a (0.63 g, 2.322 mmol) was dissolved in anhydrous EtOH (9 mL) in a 2 neck 100 mL argon purged flask. The reaction vessel was fitted with a condenser and dropping funnel and heated in an oil bath to 65° C. H$_2$O (7.5 mL), EtOH (15 mL) and aqueous (NH$_4$)$_2$S (50 wt %, 1.064 g, 7.807 mmol) were charged to the dropping funnel and added to the hot reaction mixture dropwise over 30 minutes. The reaction was heated at 65-70° C. for 2 hours then cooled to room temperature overnight. Mixture was acidified by the addition of aqueous 1M HCl to adjust pH to 0-1. The reaction mixture was filtered to remove any insoluble material and the filtrate was concentrated under reduced pressure to remove EtOH. The resulting aqueous solution was basified by the addition of aqueous 2M ammonium hydroxide solution to adjust pH to 9-10. The aqueous solution was diluted with dichloromethane and transferred to a separatory funnel and the organic layer collected. The aqueous layer was further extracted with dichloromethane and the combined organic layers were washed with H$_2$O, brine, and dried over magnesium sulphate, filtered and concentrated to afford a dark red oil. The product was purified using silica gel dry column chromatography with a solvent system of (5% 2M NH$_3$ in methanol/95% dichloromethane) to afford an orange oil/solid 4a N1-(2-Diethylamino-ethyl)-4-nitro-benzene-1,2-diamine. Yield: 0.476 grams (84.5%). $^1$H NMR (DMSO) δ 0.96 (t, 6H, J=7.1), 2.52 (m, 4H), 2.62 (t, 2H, J=6.8), 3.24 (m, 2H), 5.09 (br s, 2H), 5.82 (br s, 1H), 6.49 (d, 1H, J=8.9), 7.42 (d, 1H, J=2.6), 7.53 (dd, 1H, J=8.9, 2.6); MS (ESI): 253 (MH$^+$, 100%)

In a like manner, compound 4b N1-(2-Dimethylamino-ethyl)-4-nitro-benzene-1,2-diamine was prepared. Yield: 465 mg (70.2%) $^1$H NMR (dmso) δ: 2.19 (s, 6H), 2.47 (m, 2H), 3.26 (q, 2H, J=6.0), 5.14 (br s, 2H), 5.79 (br s, 1H), 6.49 (d, 1H, J=8.8), 7.41 (d, 1H, J=2.8), 7.54 (dd, 1H, J=8.7, 2.8); MS (ESI): 225 (MH$^+$, 100%)

Preparation of 6a-z: N1-(2-Diethylamino-ethyl)-4-nitro-benzene-1,2-diamine 4a (0.47 g, 1.863 mmol) was dissolved in anhydrous dichloromethane (110 mL) in a small, argon purged flask fitted with an condenser and magnetic stirbar. (4-Ethoxy-phenyl)-acetic acid 5 (0.352 g, 1.956 mmol) followed by 2-Ethoxy-1-ethoxycarbonyl-1,2-dihydroquinoline (0.552 g, 2.235 mmol) are added quickly as solids and resulting solution heated in an oil bath at 35° C. for 18 hours. After cooling to room temperature the solvent was removed under reduced pressure and the resulting residue partitioned between H$_2$O and chloroform and 3M ammonium hydroxide solution added to adjust pH to 11-12. The mixture was transferred to a separatory funnel and the organic layer collected. The aqueous layer was further extracted with chloroform and the combined organic layers were washed with brine, dried over magnesium sulphate, filtered and concentrated to afford crude solid. Recrystallization of the crude solid from ethyl acetate yielded a yellow powder 6a N-[2-(2-Diethylamino-ethylamino)-5-nitro-phenyl]-2-(4-ethoxy-phenyl)-acetamide. Yield: 0.305 grams (39.5%). $^1$H NMR (DMSO) δ: 0.94 (t, 6H, J=7.1), 1.31 (t, 3H, J=6.9), 2.50 (m, 4H), 2.59 (t, 2H, J=6.5), 3.26 (m, 2H), 3.55 (s, 2H), 4.02 (q, 2H, J=6.9), 6.21 (br s, 1H), 6.75 (d, 1H, J=9.9), 6.87 (d, 2H, J=8.4), 7.24 (d, 2H, J=8.4), 7.97 (m, 2H), 9.54 (br s, 1H); MS (ESI): 415 (MH$^+$, 100%)

In a like manner, starting with 4b and using anhydrous tetrahydrofuran as the reaction solvent compound 6b N-[2-(2-Dimethylamino-ethylamino)-5-nitro-phenyl]-2-(4-ethoxy-phenyl)-acetamide was prepared. Yield: 0.280 grams (35.2%) $^1$H NMR (DMSO) δ: 1.31 (t, 3H, J=6.9), 2.20 (s, 6H), 2.50 (m, 2H), 3.26 (m, 2H), 3.61 (s, 2H), 4.00 (q, 2H, J=6.9), 6.21 (br s, 1H), 6.76 (d, 1H, J=9.1), 6.87 (d, 2H, J=8.5), 7.25 (d, 2H, J=8.5), 7.97 (d, 1H, J=9.1), 8.01 (m, 1H), 9.55 (br s, 1H); MS (ESI): 387 (MH$^+$, 45%), 369 (MH$^+$—H$_2$O, 100%).

Preparation of 7a-z: N-[2-(2-Diethylamino-ethylamino)-5-nitro-phenyl]-2-(4-ethoxy-phenyl)-acetamide 6a (295 mg, 0.712 mmol), Phosphorous pentachloride (148.3 mg, 0.712 mmol) were dissolved in anhydrous chloroform (10 mL) in a small, argon purged flask fitted with a condenser and magnetic stirbar. The solution was heated to reflux in an oil bath for 4 hours and cooled to room temperature overnight. The mixture was diluted with H$_2$O and chloroform and 2M ammonium hydroxide solution added to adjust pH to 9-10. The mixture was transferred to a separatory funnel and the organic layer collected. The aqueous layer was further extracted with chloroform and the combined organic layers were washed with brine, dried over magnesium sulphate, filtered and concentrated to afford crude. The product was purified using dry silica gel column chromatography eluting with 25 mL portions of solvent system (2.5% 2M NH$_3$ in methanol/95% dichloromethane) to afford a yellow residue. Recrystallization from diethyl ether/hexanes at 0° C. yielded a pale yellow solid 7a {2-[2-(4-Ethoxy-benzyl)-5-nitro-benzoimidazol-1-yl]-ethyl}-diethyl-amine. Yield: 177 mg (62.7%). $^1$H NMR (DMSO) δ:: 0.71 (t, 6H, J=7.0), 1.29 (t, 3H, J=7.0), 2.37 (q, 4H, J=7.1), 2.50 (m, 2H), 3.98 (q, 2H, J=6.9), 4.25 (m, 2H), 4.32 (s, 2H), 6.87 (d, 2H, J=8.4), 7.19 (d, 2H, J=8.4), 7.71 (d, 1H, J=8.9), 8.14 (dd, 2H, J=8.9, 2.1), 8.45 (d, 1H, J=2.1); MS (ESI): 397 (MH$^+$, 100%)

In a like manner, compound 7b {2-[2-(4-Ethoxy-benzyl)-5-nitro-benzoimidazol-1-yl]-ethyl}-dimethyl-amine was prepared. Yield: 112 mg (58.7%) $^1$H NMR (DMSO) δ: 1.29 (t, 3H, J=7.0), 2.12 (s, 6H), 2.34 (m, 2H), 3.97 (q, 2H, J=6.9), 4.31 (m, 2H+s, 2H), 6.88 (d, 2H, J=8.7), 7.20 (d, 2H, J=8.5), 7.72 (d, 1H, J=8.9), 8.14 (dd, 1H, J=8.8, 2.1), 8.46 (d, 1H, J=2.0); MS (ESI): 369 (MH$^+$, 100%).

Preparation of 10: {2-[2-(4-Ethoxy-benzyl)-5-nitro-benzoimidazol-1-yl]-ethyl}-diethyl-amine 7a (150 mg, 0.378 mmol) was dissolved in anhydrous ethanol (10 mL) in a dry argon purged flask. Palladium, 10 wt % on activated carbon, (40.3 mg, 0.0378 mmol) is quickly added and the atmosphere from the flask evacuated by vacuum pump and replaced with hydrogen from a balloon. The atmosphere is evacuated and the flask and replaced with hydrogen twice more and the mixture stirred under a hydrogen atmosphere at room temperature. After 3 hours, thin layer chromatography in a solvent system of (5% 2M NH$_3$ in methanol/95% dichloromethane) showed complete conversion to 8a 1-(2-Diethylamino-ethyl)-2-(4-ethoxy-benzyl)-1H-benzoimidazol-5-ylamine, which is utilized without isolation. The mixture is filtered through a pad of celite to remove insolubles, the pad washed with anhydrous ethanol (10 mL) and the ethanolic solution of the amine 8a is charged to a small, argon purged flask fitted with a magnetic stirbar.

Thiophene-2-carboximidothioic acid methyl ester hydroiodide 9a (140 mg, 0.491 mmol) is added to the flask and the reaction was stirred under Ar at ambient temperature for 67 hours. The solution was diluted with diethyl ether (80 ml) and cooled in and ice bath resulting in the formation of an off-white precipitate that was collected on a sintered glass funnel and washed with ether. The hygroscopic solid was solubilized on the funnel in methanol and the solvent collected and evaporated to yield crude solid. The solid was partitioned between H$_2$O and ethyl acetate and 1M sodium hydroxide solution added to adjust pH to 8. The mixture was transferred to a separatory funnel and the organic layer collected. The aqueous layer was further extracted with ethyl acetate and the combined organic layers were washed with brine (twice), dried over magnesium sulphate, filtered and concentrated to afford yellow residue 10 N-[1-(2-Diethylamino-ethyl)-2-(4-ethoxy-benzyl)-1H-benzo-imidazol-5-yl]-thiophene-2-carboxamidine. Yield: 94 mg (52.2%). $^1$H NMR (DMSO) δ: 0.82 (t, 6H, J=7.1), 1.29 (t, 3H, J=7.0), 2.45 (q, 4H, J=7.0), 2.45-2.50 (m, 2H), 3.98 (q, 2H, J=7.0), 4.07-4.13 (m, 2H), 4.22 (s, 2H), 6.31 (br s, 2H), 6.72 (d, 1H, J=7.7), 6.88 (d, 2H, J=8.7), 6.99 (s, 1H), 7.08-7.11 (m, 1H), 7.17 (d, 2H, J=8.4), 7.35 (d, 1H, J=8.4), 7.59 (d, 1H, J=5.1), 7.72 (d, 1H, J=3.4); MS (ESI): 476 (MH$^+$, 100%)

Preparation of 11: In a like manner, starting with 7b, compound 11 N-[1-(2-Dimethylamino-ethyl)-2-(4-ethoxy-benzyl)-1H-benzoimidazol-5-yl]-thiophene-2-carboxamidine was prepared. Yield: 67 mg (61.3%). $^1$H NMR (dmso) δ: 1.31 (t, 3H, J=7.0), 2.84 (s, 6H), 4.00 (q, 2H, J=7.0) 4.31 (s, 2H), 4.48-4.65 (m, 2H), 6.90 (d, 2H, J=8.5), 7.24 (d, 2H, J=8.5), 7.31 (d, 1H, J=8.7), 7.36-7.42 (m, 1H), 7.70-7.81 (2×m, 1H+1H), 8.11 (d, 1H, J=2.8), 8.17 (d, 1H, J=4.7); MS (ESI): 448 (MH$^+$, 100%)

Preparation of 12: {2-[2-(4-Ethoxy-benzyl)-5-nitro-benzoimidazol-1-yl]-ethyl}-diethyl-amine 7a (100 mg, 0.252 mmol) was reduced to the amine 8a as outlined above and the resulting ethanolic solution charged to a small, argon purged flask fitted with a magnetic stirbar and cooled to 0° C. Thioacetimidic acid naphthalen-2-yl methyl ester hydrobromide 9b (Tet. Lett. Vol 38, (1997), pp 179-182), (74.6 mg, 0.252 mmol) is added to the flask and the reaction was stirred under Ar at 0° C. for 1 hour then at ambient temperature for 68 hours. The solution was concentrated to remove ethanol and the residue was partitioned between H$_2$O and diethyl ether. The aqueous layer was separated and washed with diethyl ether. The aqueous layer was diluted with ethyl acetate and 1M sodium hydroxide solution added to adjust pH to 8-9. The mixture was transferred to a separatory funnel and the organic layer collected. The aqueous layer was further extracted with ethyl acetate and the combined organic layers were washed with brine (twice), dried over magnesium sulphate, filtered and concentrated to afford crude. The product was purified using silica gel column chromatography eluting with 10% 2M NH$_3$ in methanol/90% dichloromethane to afford a colorless oil 12 N-[1-(2-Diethylamino-ethyl)-2-(4-ethoxy-benzyl)-1H-benzoimidazol-5-yl]-acetamidine. Yield: 65 mg (63.2%) $^1$H NMR (MeOD) δ: 1.38 (t, 6H, J=7.1), 1.40 (t, 3H, J=5.4), 2.47 (s, 3H), 3.30-3.40 (m, 4H), 3.49-3.57 (m, 2H), 4.06 (q, 2H, J=7.0), 4.73 (s, 2H), 5.03-5.13 (m, 2H), 7.01 (d, 2H, J=8.6), 7.40 (d, 2H, J=8.6), 7.61 (dd, 1H, J=8.8, 1.8), 7.81 (d, 1H, J=1.7), 8.30 (d, 1H, J=8.8). MS (ESI): 408 (MH$^+$, 100%)

Preparation of 13: {2-[2-(4-Ethoxy-benzyl)-5-nitro-benzoimidazol-1-yl]-ethyl}-diethyl-amine 7a (108 mg, 0.272 mmol) was reduced to the amine 8a as outlined above and the resulting ethanolic solution charged to a small, argon purged flask fitted with a magnetic stirbar. Furan-2-carboximidothioic acid benzyl ester hydrobromide 9c (168 mg, 0.564 mmol) is added to the flask and the reaction was stirred under Ar at ambient temperature for 19.5 hours. The solution was diluted with diethyl ether (100 mL) and cooled in and ice bath resulting in the formation of a off-white precipitate that was collected on a sintered glass funnel and washed with ether. The hygroscopic solid was solubilized on the funnel in methanol and the solvent collected and evaporated to yield crude solid. The solid was partitioned between H$_2$O and ethyl acetate and 1M sodium hydroxide solution added to adjust pH to 11. The mixture was transferred to a separatory funnel and the organic layer collected. The aqueous layer was further extracted with ethyl acetate and the combined organic layers were washed with brine (twice), dried over magnesium sulphate, filtered and concentrated to afford crude. The product was purified using silica gel column chromatography eluting with 5% 2M NH$_3$ in methanol/95% dichloromethane to afford an off white solid 13 N-(1-(2-(diethylamino)ethyl)-2-(4-ethoxybenzyl)-1H-benzo[d]imidazol-5-yl)-furan-2-carboximidamide. Yield: 125 mg (100%) $^1$H NMR (DMSO) δ: 0.83 (t, 6H, J=7.1), 1.27 (t, 3H, J=6.9), 2.39-2.50 (2×m, 6H), 3.97 (q, 2H, J=6.9), 4.09 (t, 2H, J=6.8), 4.21 (s, 2H), 6.10 (br s, 2H), 6.58-6.63 (m, 1H), 6.72 (d, 1H, J=7.9), 6.86 (d, 2H, J=8.5), 6.99 (br s, 1H), 7.10 (d, 1H, J=3.1), 7.17 (d, 2H, J=8.6), 7.34 (d, 1H, J=8.6), 7.78 (s, 1H).

Preparation of 14: {2-[2-(4-Ethoxy-benzyl)-5-nitro-benzoimidazol-1-yl]-ethyl}-diethyl-amine 7a (108 mg, 0.273 mmol) was reduced to the amine 8a as outlined above and the resulting ethanolic solution charged to a small, argon purged flask fitted with a magnetic stirbar. Furan-3-carboximidothioic acid benzyl ester hydrobromide 9d (171 mg, 0.574 mmol) is added to the flask and the reaction was stirred under Ar at ambient temperature for 20 hours. The solvent was evaporated and the residue partitioned between H$_2$O and ethyl acetate and 3M sodium hydroxide solution added to adjust pH to 11. The mixture was transferred to a separatory funnel and the organic layer collected. The aqueous layer was further extracted with ethyl acetate and the combined organic layers were washed with brine (twice), dried over magnesium sulphate, filtered and concentrated to afford crude. The product was purified using silica gel column chromatography eluting with 5% 2M NH$_3$ in methanol/95% dichloromethane to afford a pale yellow oil 14 N-(1-(2-(diethylamino)ethyl)-2-(4-ethoxybenzyl)-1H-benzo[d]imidazol-5-yl)furan-2-carboximidamide. Yield: 62.8 mg (50.0%) $^1$H NMR (DMSO) δ; 0.83 (t, 6H, J=7.0), 1.29 (t, 3H, J=7.0), 2.37-2.50 (2×m, 6H), 3.99 (q, 2H, J=6.9), 4.10 (t, 2H, J=6.8), 4.21 (s, 2H), 5.98-6.09 (br, 1-2H), 6.71 (d, 1H, J=9.6), 6.86 (d, 2H, J=8.7), 6.88-6.92 (m, 1H), 6.96 (br, 1H), 7.18 (d, 2H, J=8.5), 7.33 (d, 1H, J=8.5), 7.68-7.73 (m, 1H), 8.23 (s, 1H). MS (ESI): 460 (MH$^+$, 95%)

Preparation of 15: {2-[2-(4-Ethoxy-benzyl)-5-nitro-benzoimidazol-1-yl]-ethyl}-diethyl-amine 7a (120 mg, 0.303 mmol) was reduced to the amine 8a as outlined above and the resulting ethanolic solution charged to a small, argon purged flask fitted with a magnetic stirbar and condenser. H$_2$O (7 mL) and N-methyl-N-nitroso-N'-nitroguanidine 9e (37.0 mg, 0.251 mmol) prepared according to J. Am. Chem. Soc. 71, 1968-1970, (1949) are charged to flask and mixture heated to reflux for 1 hour then cooled to room temperature overnight. TLC shows incomplete conversion thus (13.4 mg, 0.091 mmol) 9e added and mixture refluxed for a further 5 hours. Cooled to room temperature and concentrated to remove ethanol. The aqueous layer was transferred to a separatory funnel and extracted with ethyl acetate and the organic layer collected. The aqueous layer was further extracted with ethyl acetate and the combined organic layers were washed with brine (twice), dried over magnesium sulphate, filtered and concentrated to afford crude. The product was purified using silica gel column chromatography eluting with 2.5% 2M NH$_3$ in methanol/97.5% dichloromethane to 5% 2M NH$_3$ in methanol/95% dichloromethane afford after triturating with diethyl ether a beige solid 15 1-(1-(2-(diethylamino)ethyl)-2-(4-ethoxybenzyl)-1H-benzo[d]imidazol-5-yl)-3-nitroguanidine Yield: 35 mg (31%) $^1$H NMR (DMSO) δ; 0.79 (t, 6H, J=7.0), 1.29 (t, 3H, J=7.0), 2.40-2.50 (2×m, 6H), 3.98 (q, 2H, J=6.9), 4.13 (t, 2H, J=6.1), 4.26 (s, 2H), 6.85 (d, 2H, J=8.6), 7.06 (dd, 1H, J=8.8, 1.7), 7.15 (d, 2H, J=8.4), 7.44-7.52 (m, 2H), 7.94-8.30 (br, 2H), 9.60-9.89 (br, 1H). MS (ESI): 454 (MH$^+$, 100%)

Preparation of 16: {2-[2-(4-Ethoxy-benzyl)-5-nitro-benzoimidazol-1-yl]-ethyl}-diethyl-amine 7a (108 mg, 0.273 mmol) was reduced to the amine 8a as outlined above and the resulting ethanolic solution charged to a small, argon purged flask fitted with a magnetic stirbar. Thiophene-3-carboximidothioic acid benzyl ester hydrobromide 9f (182 mg, 0.575 mmol) is added to the flask and the reaction was stirred under Ar at ambient temperature for 108 hours. The solvent was evaporated and the residue partitioned between H$_2$O and ethyl acetate and 3M sodium hydroxide solution added to adjust pH to 10. The mixture was transferred to a separatory funnel and the organic layer collected. The aqueous layer was further extracted with ethyl acetate and the combined organic layers were washed with brine (twice), dried over magnesium sulphate, filtered and concentrated to afford crude. The product was purified using silica gel dry column chromatography eluting with 5% 2M NH$_3$ in methanol/95% dichloromethane then purified using a second silica gel column eluting with 60% methanol/40% dichloromethane to afford a pale yellow solid 16 N-(1-(2-(diethylamino)ethyl)-2-(4-ethoxybenzyl)-1H-benzo[d]imidazol-5-yl)thiophene-3-carboximidamide. Yield: 40 mg (30.8%) $^1$H NMR (DMSO) δ; 0.83 (t, 6H, J=7.0), 1.30 (t, 3H, J=6.9), 2.38-2.50 (2×m, 6H), 3.97 (q, 2H, J=7.0), 4.10 (t, 2H, J=6.5), 4.22 (s, 2H), 6.12 (br, 2H), 6.73 (d, 1H, J=8.3), 6.86 (d, 2H, J=8.4), 6.97 (d, 1H, J=1.8), 7.19 (d, 2H, J=8.6), 7.34 (d, 1H, J=8.4), 7.53-7.55 (m, 1H), 7.61-7.66 (m, 1H), 8.13 (d, 1H, J=3.0). MS (ESI): 476 (MH$^+$, 25%), 377 (100%).

Example 2

Preparation of the Compounds of Formula 20-22

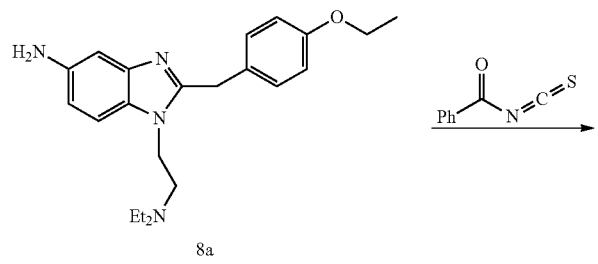

8a

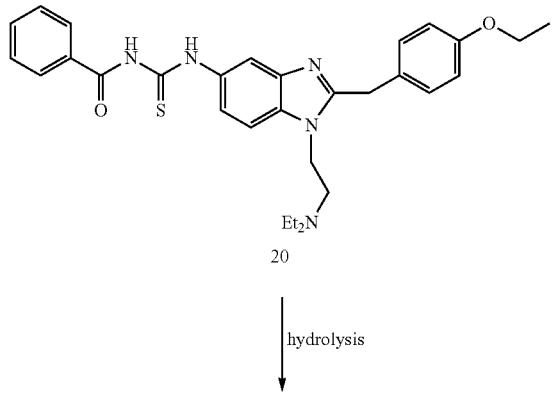

20

| hydrolysis

 →alkylation 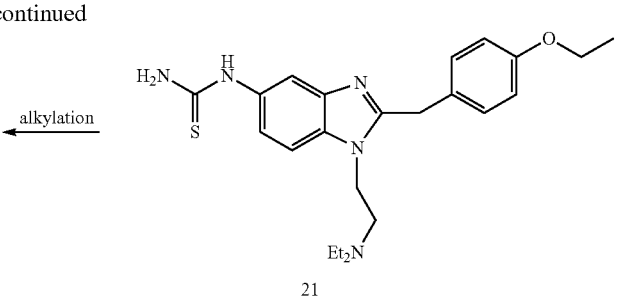

21

Preparation of 20: {2-[2-(4-Ethoxy-benzyl)-5-nitro-benzoimidazol-1-yl]-ethyl}-diethyl-amine 7a (377 mg, 0.950 mmol) was reduced to the amine 8a as outlined above and the resulting ethanolic solution charged to a small, argon purged flask fitted with a magnetic stirbar. Anhydrous tetrahydrofuran (10 mL) added followed by dropwise addition of benzoyl isothiocyanate (178 mg, 1.093 mmol) and mixture stirred under Ar at ambient temperature for 3 hours then allowed to stand overnight at room temperature. 3-(Dimethylamino)propyl functionalized silica gel (205 mg, 0.286 mmol) added and mixture stirred for 1 hour, filtered and concentrated to yield crude. The product was purified using silica gel column chromatography eluting with 2.5% 2M $NH_3$ in methanol/97.5% dichloromethane to afford a pale yellow oil. Trituration with diethyl ether/hexanes yielded an off white solid 20 N-(1-(2-(diethylamino)ethyl)-2-(4-ethoxybenzyl)-1H-benzo[d]-imidazol-5-ylcarbamothioyl)benzamide. Yield: 160 mg (31.7%) $^1$H NMR (DMSO) δ: 0.80 (t, 6H, J=7.0), 1.30 (t, 3H, J=7.0), 2.34-2.50 (2×m, 6H), 3.98 (q, 2H, J=7.0), 4.16 (t, 2H, J=6.3), 4.27 (s, 2H), 6.87 (d, 2H, J=8.4), 7.18 (d, 2H, J=8.5), 7.34 (d, 1H, J=8.4), 7.44-7.59 (2×m, 3H), 7.62-7.69 (m, 1H), 7.94-8.03 (2×m, 3H), 11.48 (br s, 1H), 12.60 (br s, 1H). MS (ESI): 530 ($MH^+$, 100%)

Preparation of 22: N-(1-(2-(diethylamino)ethyl)-2-(4-ethoxybenzyl)-1H-benzo[d]-imidazol-5-ylcarbamothioyl) benzamide 20 (272 mg, 0.513 mmol) was dissolved in anhydrous tetrahydrofuran (10 mL) in a small, argon purged flask fitted with an condenser and magnetic stirbar. 2M NaOH (0.513 mL, 1.026 mmol) added and the solution was heated to reflux for 6 hours and cooled to room temperature overnight. The solution was concentrated and the residue was partitioned between $H_2O$ and ethyl acetate, transferred to a separatory funnel and the organic layer collected. The aqueous layer was further extracted with ethyl acetate and the combined organic layers were washed with brine (twice), dried over magnesium sulphate, filtered and concentrated to afford an off white solid which was slurried in hot ethyl acetate to yield white solid 21 [1-(2-Diethylamino-ethyl)-2-(4-ethoxy-benzyl)-1H-benzoimidazol-5-yl]-thiourea. Yield: 110 mg (50.3%). $^1$H NMR (DMSO) δ: 0.80 (t, 6H, J=7.1), 1.29 (t, 3H, J=7.0), 2.41 (q, 4H, J=7.0), 2.45-2.50 (m, 2H), 3.96 (q, 2H, J=6.9), 4.12 (t, 2H, J=6.7), 4.24 (s, 2H), 6.86 (d, 2H, J=8.6), 7.09 (dd, 1H, J=8.4, 1.5), 7.16 (d, 2H, J=8.7), 7.24 (br, 1-2H), 7.40 (d, 1H, J=8.5), 7.51 (s, 1H), 9.56 (s, 1H). MS (ESI): 426 ($MH^+$, 100%)

1-(2-Diethylamino-ethyl)-2-(4-ethoxy-benzyl)-1H-benzoimidazol-5-yl]-thiourea 21 (75 mg, 0.176 mmol) was dissolved in anhydrous dimethylformamide (5 mL) in a small, argon purged flask fitted with a magnetic stirbar. Iodoethane (14 ul, 0.176 mmol) and potassium carbonate (48.6 mg, 0.352 mmol) added and the flask sealed. After 20 hours stirring at room temperature a further portion of iodoethane (4.3 ul, 0.053 mmol) was added and the mixture stirred for 2 further hours. The reaction mixture was diluted with $H_2O$ and ethyl acetate, transferred to a separatory funnel and the organic layer collected. The aqueous layer was further extracted with ethyl acetate and the combined organic layers were washed with brine, dried over magnesium sulphate, filtered and concentrated to afford crude. The product was purified using dry silica gel column chromatography eluting with 25 mL portions of solvent system (5% 2M $NH_3$ in methanol/95% dichloromethane) then subjected to a second silica gel column eluting with 5% methanol/95% dichloromethane to 10% methanol/90% dichloromethane to yield a colorless residue. 22    1-[1-(2-Diethylamino-ethyl)-2-(4-ethoxy-benzyl)-1H-benzoimidazol-5-yl]-2-ethyl-isothiourea. Yield: 47 mg (58.8%) $^1$H NMR (DMSO) δ: 80.81 (t, 6H, J=7.0), 1.09-1.29 (m, 3H), 1.29 (t, 3H, J=6.9), 2.36-2.50 (2×m, 6H), 2.81-3.04 (m, 2H), 3.97 (q, 2H, J=6.9), 4.07 (t, 2H, J=6.7), 4.19 (s, 2H), 5.95-6.42 (2×br, 2H), 6.57-6.73 (m, 1H), 6.87 (d, 2H, J=8.4), 6.85-6.95 (br, 1H), 7.15 (d, 2H, J=8.4), 7.27 (d, 1H, J=8.2). MS (ESI): 454 ($MH^+$, 100%)

Example 3

Preparation of the Compounds of Formula 30-36

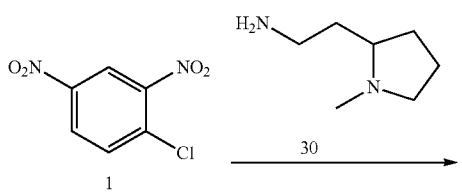

-continued
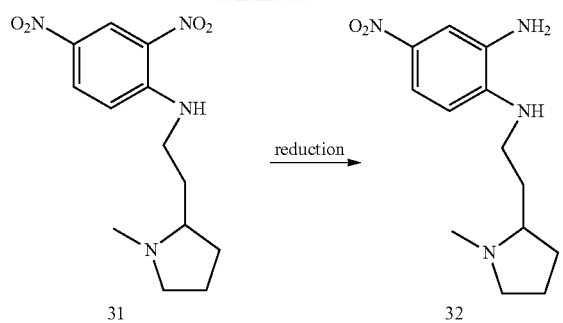
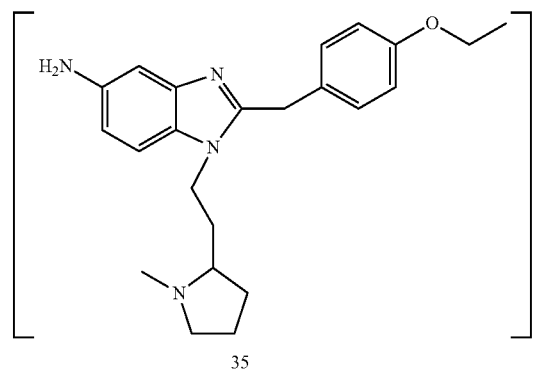

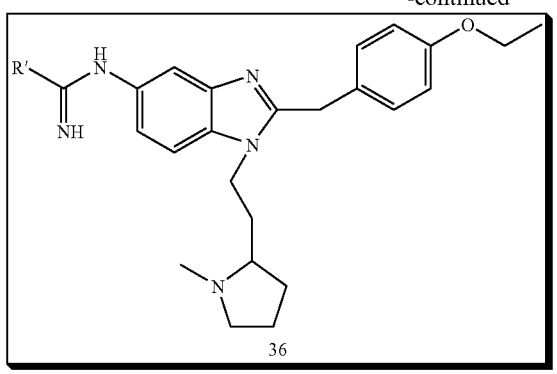

36

Preparation of 31: Chloro-2,4-dinitrobenzene 1 (1.00 g, 4.937 mmol) was dissolved in anhydrous EtOH (20 mL) in a small argon purged flask and warmed in an oil bath to 40° C. Addition of 2-(1-methylpyrrolidin-2-yl)ethanamine 30 (0.696 g, 5.431 mmol) occurred dropwise. The reaction was stirred at 65-70° C. for 24 hours. After cooling to room temperature the solvent was removed under reduced pressure and the resulting residue partitioned between $H_2O$ and ethyl acetate and 1M ammonium hydroxide solution added to adjust pH to 10. The mixture was transferred to a separatory funnel and the organic layer collected. The aqueous layer was further extracted with ethyl acetate and the combined organic layers were washed with $H_2O$, brine (twice), dried over magnesium sulphate, filtered and then concentrated. Recrystallization of the crude solid from EtOH yielded a yellow powder 31 (2,4-Dinitro-phenyl)-[2-(1-methyl-pyrrolidin-2-yl)-ethyl]-amine Yield: 0.979 grams (67.4%). $^1$H NMR (DMSO) δ-1.51-1.71 (m, 3H), 1.78-1.96 (2×m, 3H), 2.06-2.14 (m, 1H), 2.26 (s, 3H), 2.26-2.36 (m, 1H), 2.93-3.03 (m, 1H), 3.48-3.53 (m, 2H), 7.18 (d, 1H, J=9.6), 8.27 (dd, 1H, J=9.7, 2.7), 8.86 (d, 1H, J=2.8), 9.50 (br s, 1H); MS (ESI): 295 (MH$^+$, 100%)

Preparation of 32: (2,4-Dinitro-phenyl)-[2-(1-methyl-pyrrolidin-2-yl)-ethyl]-amine 31 (0.979 g, 3.329 mmol) was dissolved in anhydrous EtOH (16 mL) in a 2 neck 100 mL argon purged flask. The reaction vessel was fitted with a condenser and dropping funnel and heated in an oil bath to 65° C. $H_2O$ (16 mL), EtOH (32 mL) and aqueous $(NH_4)_2S$ (50 wt %, 1.59 g, 11.652 mmol) were charged to the dropping funnel and added to the hot reaction mixture dropwise over 45 minutes. The reaction was heated at 65-70° C. for 2 hours then cooled to room temperature overnight. Mixture was acidified by the addition of aqueous 4M HCl to adjust pH to 2. The reaction mixture was filtered to remove any insoluble material and the filtrate was concentrated under reduced pressure to remove EtOH. The resulting aqueous solution was basified by the addition of aqueous 2M ammonium hydroxide solution to adjust pH to 10. The aqueous solution was diluted with dichloromethane and transferred to a separatory funnel and the organic layer collected. The aqueous layer was further extracted with dichloromethane and the combined organic layers were washed with $H_2O$, brine, and dried over magnesium sulphate, filtered and concentrated to afford a dark red oil. The product was purified using silica gel dry column chromatography with a solvent system of (5% 2M $NH_3$ in methanol/95% dichloromethane to 10% 2M $NH_3$ in methanol/90% dichloromethane) to afford an orange-red oil/solid 32 N1-[2-(1-Methyl-pyrrolidin-2-yl)-ethyl]-4-nitro-benzene-1,2-diamine Yield: 0.396 grams (45.1%). $^1$H NMR (DMSO) δ: 1.39-1.69 (m, 5H), 1.86-1.98 (m, 2H), 2.01-2.10 (m, 1H), 2.10-2.16 (m, 1H), 2.22 (s, 3H), 2.91-2.98 (m, 1H), 3.16-3.24 (m, 2H), 5.11 (br s, 2H), 5.92-5.98 (m, 1H), 6.46 (d, 1H, J=8.8), 7.40 (d, 1H, J=2.5), 7.52 (dd, 1H, J=8.9, 2.5); MS (ESI): 265 (MH$^+$, 100%).

Preparation of 33: N1-[2-(1-Methyl-pyrrolidin-2-yl)-ethyl]-4-nitro-benzene-1,2-diamine 32 (0.396 g, 1.498 mmol) was dissolved in anhydrous chloroform (20 mL) in a small, argon purged flask fitted with an condenser and magnetic stirbar. (4-Ethoxy-phenyl)-acetic acid 5 (0.284 g, 1.573 mmol) followed by 2-Ethoxy-1-ethoxycarbonyl-1,2-dihydroquinoline (0.455 g, 1.841 mmol) are added quickly as solids and resulting solution heated in an oil bath at 35° C. for 18 hours. After cooling to room temperature the solvent was removed under reduced pressure and the resulting residue partitioned between $H_2O$ and chloroform and 2M ammonium hydroxide solution added to adjust pH to 10. The mixture was transferred to a separatory funnel and the organic layer collected. The aqueous layer was further extracted with chloroform and the combined organic layers were washed with brine, dried over magnesium sulphate, filtered and concentrated to afford crude solid. The product was purified using silica gel dry column chromatography with a solvent system of (5% 2M $NH_3$ in methanol/95% dichloromethane) to afford a yellow powder 33 2-(4-Ethoxy-phenyl)-N-{2-[2-(1-methyl-pyrrolidin-2-yl)-ethylamino]-5-nitro-phenyl}-acetamide Yield: 0.115 grams (18.0%). $^1$H NMR (DMSO) δ: 1.31 (t, 3H, J=7.0), 1.43-1.68 (2×m, 4-5H), 1.78-1.91 (m, 2H), 2.01-2.10 (m, 1H), 2.12-2.19 (m, 1H), 2.22 (s, 3H), 2.89-2.99 (m, 1H), 3.19-3.30 (m, 2H), 3.61 (s, 2H), 4.00 (q, 2H, J=6.9), 6.57 (br, 1H), 6.70 (d, 1H, J=9.1), 6.88 (d, 2H, J=8.4), 7.24 (d, 2H, J=8.6), 7.94 (dd, 1H, J=9.1, 2.6), 7.99 (d, 1H, J=2.5), 9.43 (br s, 1H); MS (ESI): 427 (MH$^+$, 100%).

Preparation of 34: 2-(4-Ethoxy-phenyl)-N-{2-[2-(1-methyl-pyrrolidin-2-yl)-ethylamino]-5-nitro-phenyl}-acetamide 33 (60 mg, 0.141 mmol), Phosphorous pentachloride (33 mg, 0.158 mmol) were dissolved in anhydrous chloroform (10 mL) in a small, argon purged flask fitted with an condenser and magnetic stirbar. The solution was heated to reflux in an oil bath for 4.5 hours and cooled to room temperature overnight. The mixture was diluted with $H_2O$ and chloroform and 2M ammonium hydroxide solution added to adjust pH to 9-10. The mixture was transferred to a separatory funnel and the organic layer collected. The aqueous layer was further extracted with chloroform and the combined organic layers were washed with brine, dried over magnesium sulphate, filtered and concentrated to afford crude. The product was purified using silica gel column chromatography eluting with a solvent system of 5% 2M $NH_3$ in methanol/95% dichloromethane to afford a pale yellow solid 34 2-(4-Ethoxy-benzyl)-1-[2-(1-methyl-pyrrolidin-2-yl)-ethyl]-5-nitro-1H-benzimidazole Yield: 22 mg (38.3%). $^1$H NMR (DMSO) δ: 1.29 (t, 3H, J=7.0), 1.38-1.51 (m, 2H), 1.51-1.70 (m, 3H), 1.75-1.87 (m, 1H), 1.96-2.05 (m, 2H), 2.07 (s, 3H), 2.85-2.95 (m, 1H), 3.97 (q, 2H, J=7.0), 4.21 (t, 2H, J=7.9), 4.32 (s, 2H), 6.87 (d, 2H, J=8.5), 7.19 (d, 2H, J=8.5), 7.70 (d, 1H, J=9.0), 8.14 (dd, 1H, J=8.9, 2.1), 8.47 (d, 1H, J=2.1); MS (ESI): 409 (MH$^+$, 100%).

Preparation of 36: 2-(4-Ethoxy-benzyl)-1-[2-(1-methyl-pyrrolidin-2-yl)-ethyl]-5-nitro-1H-benzimidazole 34 (45 mg, 0.110 mmol) was dissolved in anhydrous ethanol (5 mL) in a dry argon purged flask. Palladium, 10 wt % on activated carbon (15 mg, 0.014 mmol) is quickly added and the atmosphere from the flask evacuated by vacuum pump and replaced with hydrogen from a balloon. The atmosphere is evacuated from the flask and replaced with hydrogen twice more and the mixture stirred under a hydrogen atmosphere at room temperature. After 20 hours, thin layer chromatography in a solvent system of (5% 2M NH$_3$ in methanol/95% dichloromethane) shows complete conversion to 35 2-(4-Ethoxy-benzyl)-1-[2-(1-methyl-pyrrolidin-2-yl)-ethyl]-1H-benzoimidazol-5-ylamine, which is utilized without isolation. The mixture is filtered through a pad of celite to remove insolubles, the pad washed with anhydrous ethanol (5 mL) and the ethanolic solution of the amine 35 is charged to a small, argon purged flask fitted with a magnetic stirbar. Thiophene-2-carboximidothioic acid methyl ester hydroiodide 9a (110.6 mg, 0.388 mmol) is added to the flask and the reaction was stirred under Ar at ambient temperature for 67 hours. The solvent was removed and the residue partitioned between H$_2$O and ethyl acetate and 3M sodium hydroxide solution added to adjust pH to 10. The mixture was transferred to a separatory funnel and the organic layer collected. The aqueous layer was further extracted with ethyl acetate and the combined organic layers were washed with brine (twice), dried over magnesium sulphate, filtered and concentrated to afford crude product. The reaction was repeated on a 67 mg scale and the combined crudes purified using silica gel dry column chromatography with a solvent system of (2.5% 2M NH$_3$ in methanol/97.5% dichloromethane to 10% 2M NH$_3$ in methanol/90% dichloromethane) then a second silica gel dry column with a solvent system of (10% methanol/90% dichloromethane to 100% methanol) to afford a beige solid 36 N-{2-(4-Ethoxy-benzyl)-1-[2-(1-methyl-pyrrolidin-2-yl)-ethyl]-1H-benzoimidazol-5-yl}-thiophene-2-carboxamidine. Yield: 48 mg (35.9%). $^1$H NMR (DMSO) δ: 1.29 (t, 3H, J=6.9), 1.35-1.49 (m, 2H), 1.54-1.69 (m, 3H), 1.77-1.90 (m, 1H), 1.95-2.05 (m, 2H), 2.08 (s, 3H), 2.84-2.95 (m, 1H), 3.98 (q, 2H, J=6.9), 4.06 (t, 2H, J=7.7), 4.20 (s, 2H), 6.33 (br s, 2H), 6.73 (dd, 1H, J=8.7, 1.6), 6.87 (d, 2H, J=8.8), 7.00 (d, 1H, J=1.6), 7.09 (dd, 1H, J=5.2, 3.8), 7.19 (d, 2H, J=8.6), 7.33 (d, 1H, J=8.4), 7.59 (d, 1H, J=5.4), 7.73-7.74 (m, 1H); MS (ESI): 488 (MH$^+$, 60%), 244 (100%).

Example 4

Preparation of the Compounds of Formula 40-45

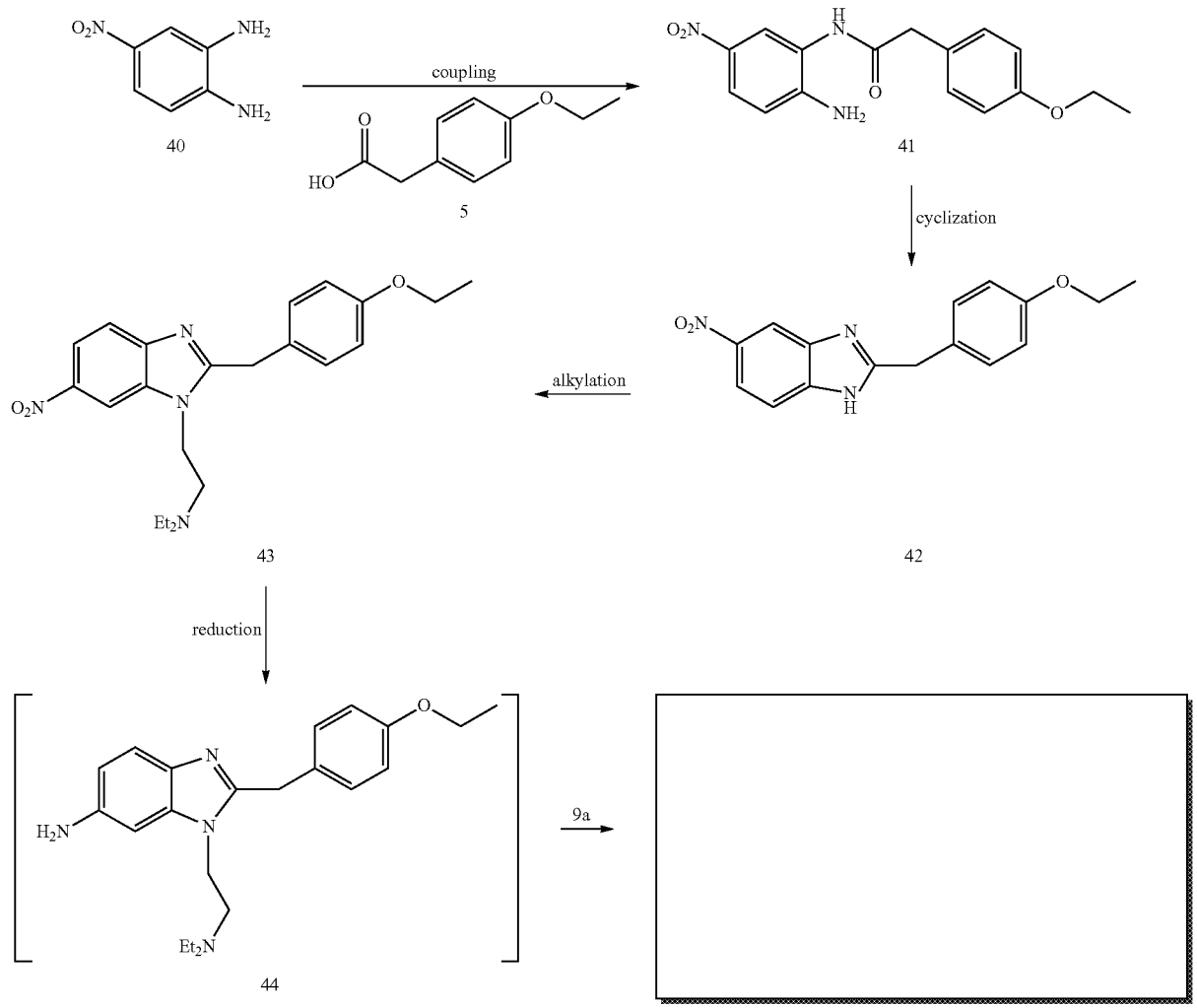

Preparation of 41: 4-Nitro-benzene-1,2-diamine 40 (1.00 g, 6.53 mmol) was dissolved in anhydrous dimethylformamide (20 mL) in a small, argon purged flask fitted with an condenser and magnetic stirbar. (4-Ethoxy-phenyl)-acetic acid 5 (1.53 g, 8.49 mmol) followed by 2-Ethoxy-1-ethoxy-carbonyl-1,2-dihydroquinoline (2.099 g, 8.49 mmol) are added quickly as solids and resulting solution heated in an oil bath at 100° C. for 17 hours. After cooling to room temperature the solution was diluted with ice cold $H_2O$ (25 mL) resulting in the formation of a yellow precipitate that was collected on a sintered glass funnel and washed with $H_2O$. The solid was slurried in boiling ethanol, filtered and dried to yield solid 41 N-(2-Amino-5-nitro-phenyl)-2-(4-ethoxy-phenyl)-acetamide Yield: 1.31 grams (67.5%). $^1$H NMR (DMSO) δ: 1.31 (t, 3H, J=6.9), 3.61 (s, 2H), 4.00 (q, 2H, J=6.9), 6.50 (br s, 2H, exchange w. $D_2O$), 6.75 (d, 1H, J=9.0), 6.87 (d, 2H, J=8.4), 7.25 (d, 2H, J=8.7), 7.84 (dd, 1H, J=9.0, 2.7), 8.20 (d, 1H, J=2.7), 9.37 (br s, 1H, exchange w. $D_2O$); MS (APCI+): 316 (MH$^+$, 10%), 298 (MH+-$H_2O$, 100%).

Preparation of 42: N-(2-Amino-5-nitro-phenyl)-2-(4-ethoxy-phenyl)-acetamide 41 (590 mg, 1.871 mmol), Phosphorous pentachloride (390 mg, 1.871 mmol) were dissolved in anhydrous chloroform (20 mL) in a small, argon purged flask fitted with an condenser and magnetic stirbar. The solution was heated to reflux in an oil bath for 4 hours and cooled to room temperature overnight. The mixture was diluted with $H_2O$ and chloroform and 2M ammonium hydroxide solution added to adjust pH to 9-10. The mixture was transferred to a separatory funnel and the organic layer collected. The aqueous layer was further extracted with chloroform and the combined organic layers were washed with brine, dried over magnesium sulphate, filtered and concentrated to afford crude. The product was purified using dry silica gel column chromatography eluting with 20 mL portions of solvent system (2.5% 2M $NH_3$ in methanol/95% dichloromethane) to afford a yellow residue 42 2-(4-Ethoxy-benzyl)-5-nitro-1H-benzimidazole. $^1$H NMR (DMSO) δ: 1.30 (t, 3H, J=6.5), 3.87 (q, 2H, J=7.3), 4.11 (s, 2H), 6.88 (d, 2H, J=8.0), 7.25 (d, 2H, J=7.9), 7.65 (d, 1H, J=8.9), 8.07 (d, 1H, J=9.0), 8.36-8.40 (m, 1H); MS (ESI): 298 (MH$^+$, 100%)

Preparation of 43: To a small, argon purged flask fitted with a condenser and magnetic stirbar is charged Sodium Hydride (60 wt %, 74 mg, 1.850 mmol) and anhydrous dioxane (5 mL) and stirring begun. A solution of 2-(4-Ethoxy-benzyl)-5-nitro-1H-benzimidazole 42 (550 mg, 1.850 mmol) in anhydrous dioxane (10 mL) was added dropwise to the suspension of sodium hydride and the mixture heated to 65° C. for 90 minutes at which time a solution of (2-Chloroethyl)-diethyl-amine (251 mg, 1.850 mmol) in anhydrous dioxane (5 mL) is added dropwise to the hot solution. After 60 minutes at 65° C. the mixture is cooled to room temperature, filtered and solvent removed under reduced pressure to afford crude. The product was purified using dry silica gel column chromatography eluting with 25 mL portions of solvent system (1.25% 2M $NH_3$ in methanol/98.75% dichloromethane to 2.5% 2M $NH_3$ in methanol/97.5% dichloromethane). The enriched fractions were further purified using silica gel column chromatography eluting with 50% ethyl acetate/50% hexanes to 70% ethyl acetate/30% hexanes to afford a pale yellow-colorless solid 43 {2-[2-(4-Ethoxy-benzyl)-6-nitro-benzoimidazol-1-yl]-ethyl}-diethyl-amine Yield: 100 mg (13.6%). $^1$H NMR (DMSO) δ: 0.70 (t, 6H, J=7.1), 1.30 (t, 3H, J=6.9), 2.39 (q, 4H, J=7.1), 2.50 (m, 2H), 3.98 (q, 2H, J=6.9), 4.28-4.36 (s, 2H; m, 2H) 6.87 (d, 2H, J=8.7), 7.20 (d, 2H, J=8.6), 7.72 (d, 1H, J=9.0), 8.06 (dd, 2H, J=8.9, 2.1), 8.51 (d, 1H, J=2.1); MS (ESI): 397 (MH$^+$, 100%).

Preparation of 45: {2-[2-(4-Ethoxy-benzyl)-6-nitro-benzoimidazol-1-yl]-ethyl}-diethyl-amine 43 (90 mg, 0.227 mmol) was dissolved in anhydrous ethanol (7 mL) in a dry argon purged flask. Palladium, 10 wt % on activated carbon (24 mg, 0.0227 mmol) is quickly added and the atmosphere from the flask evacuated by vacuum pump and replaced with hydrogen from a balloon. The atmosphere is evacuated from the flask and replaced with hydrogen twice more and the mixture stirred under a hydrogen atmosphere at room temperature. After 3 hours, thin layer chromatography in a solvent system of (5% 2M $NH_3$ in methanol/95% dichloromethane) shows complete conversion to 44 3-(2-Diethylamino-ethyl)-2-(4-ethoxy-benzyl)-3H-benzoimidazol-5-ylamine, which is utilized without isolation. The mixture is filtered through a pad of celite to remove insolubles, the pad washed with anhydrous ethanol (7 mL) and the ethanolic solution of the amine 44 is charged to a small, argon purged flask fitted with a magnetic stirbar. Thiophene-2-carboximidothioic acid methyl ester hydroiodide 9a (129.5 mg, 0.454 mmol) is added to the flask and the reaction was stirred under Ar at ambient temperature for 44 hours. The solvent was evaporated and residue partitioned between $H_2O$ and ethyl acetate and 1M sodium hydroxide solution added to adjust pH to 8. The mixture was transferred to a separatory funnel and the organic layer collected. The aqueous layer was further extracted with ethyl acetate and the combined organic layers were washed with brine (twice), dried over magnesium sulphate, filtered and concentrated to afford crude. The product was purified using silica gel column chromatography eluting with 3% methanol/97% dichloromethane to 5% methanol/95% dichloromethane to afford a yellow solid 45 N-[3-(2-Diethylamino-ethyl)-2-(4-ethoxy-benzyl)-3H-benzoimidazol-5-yl]-thiophene-2-carboxamidine. Yield: 38 mg (35.2%). $^1$H NMR (DMSO) δ: 0.81 (t, 6H, J=7.0), 1.28 (t, 3H, J=7.0), 2.35-2.50 (2×m, 6H), 3.97 (q, 2H, J=7.0), 4.07 (t, 2H, J=6.7), 4.21 (s, 2H), 6.42 (br s, 2H), 6.67-6.70 (m, 1H), 6.85-6.88 (m, 1H), 6.88 (d, 2H, J=8.6), 7.08-7.11 (m, 1H), 7.17 (d, 2H, J=8.7), 7.46 (d, 1H, J=8.5), 7.60 (d, 1H, J=5.2), 7.73 (d, 1H, J=3.6); MS (ESI): 476 (MH$^+$, 100%).

Example 5

Preparation of the Compounds of Formula 50-59

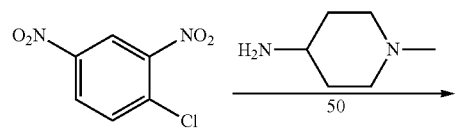

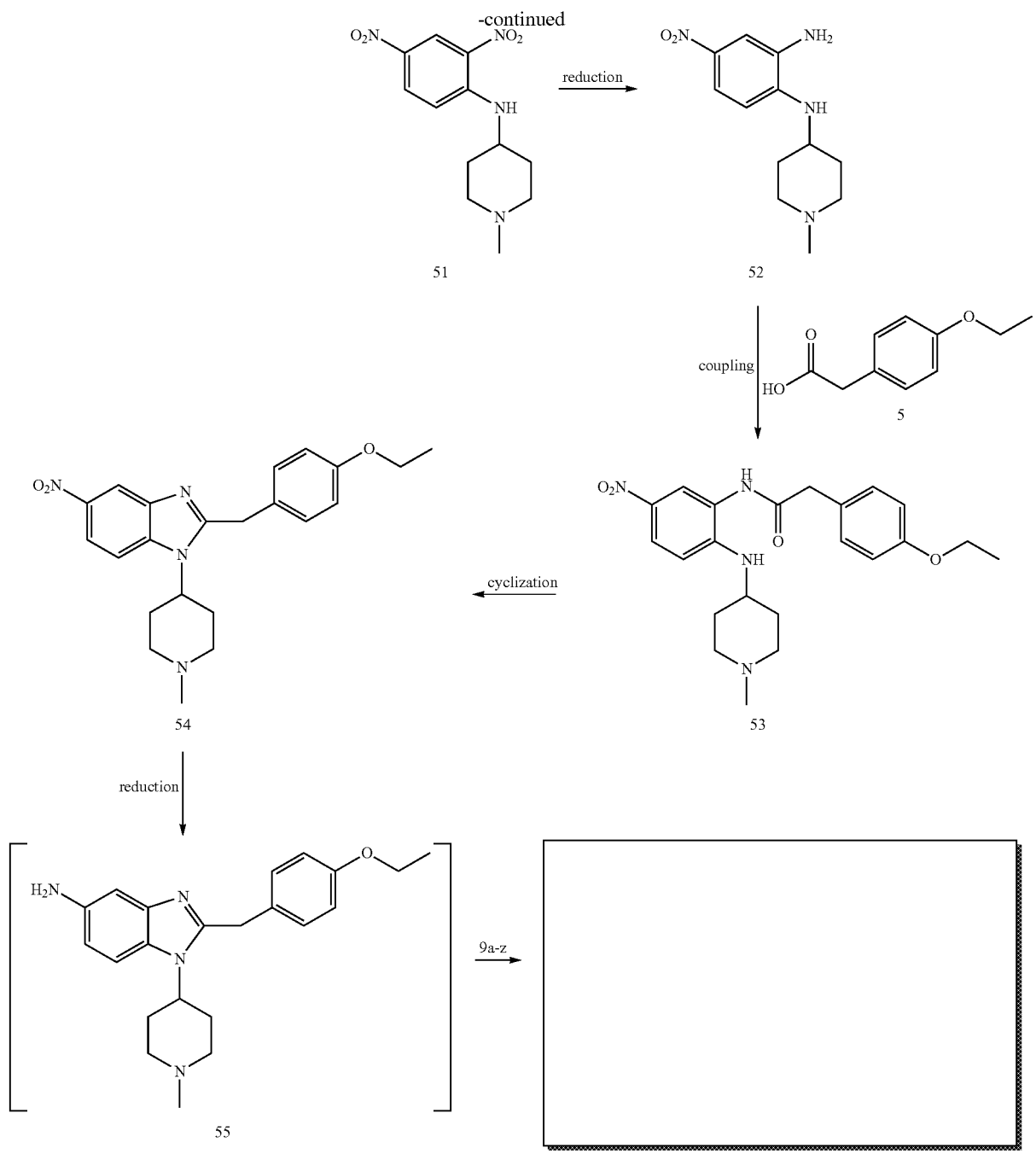

Preparation of 51: Chloro-2,4-dinitrobenzene 1 (2.0 g, 9.874 mmol) was dissolved in anhydrous EtOH (40 mL) in a small argon purged flask and warmed in an oil bath to 40° C. Addition of 1-Methyl-piperidin-4-ylamine 50 (1.24 g, 10.862 mmol) occurred dropwise. The solution was heated to reflux in an oil bath for 48 hours. After cooling to room temperature the solvent was removed under reduced pressure and the resulting residue partitioned between $H_2O$ and ethyl acetate and IM ammonium hydroxide solution added to adjust pH to 9. The mixture was transferred to a separatory funnel and the organic layer collected. The aqueous layer was further extracted with ethyl acetate and the combined organic layers were washed with $H_2O$, brine (twice), dried over magnesium sulphate, filtered and then concentrated. Recrystallization of the crude solid from EtOH yielded a yellow solid 51 (2,4-Dinitro-phenyl)-(1-methyl-piperidin-4-yl)-amine Yield: 1.50 grams (54.2%). $^1$H NMR (DMSO) δ: 1.59-1.75 (m, 2H), 1.86-1.98 (m, 2H), 2.06-2.17 (m, 2H), 2.18 (s, 3H), 2.62-2.77 (m, 2H), 3.71-3.84 (m, 1H), 7.31 (d, 1H, J=9.7), 8.24 (dd, 1H, J=9.7, 2.7), 8.45 (d, 1H, J=7.7), 8.85 (d, 1H, J=2.6); MS (ESI): 281 (MH$^+$, 100%).

Preparation of 52: (2,4-Dinitro-phenyl)-(1-methyl-piperidin-4-yl)-amine 51 (1.50 g, 5.352 mmol) was dissolved in anhydrous EtOH (20 mL) in a 2 neck 250 mL argon purged flask. The reaction vessel was fitted with a condenser and dropping funnel and heated in an oil bath to 65° C. $H_2O$ (20 mL), EtOH (40 mL) and aqueous $(NH_4)_2S$ (50 wt %, 2.55 g, 18.73 mmol) were charged to the dropping funnel and added to the hot reaction mixture dropwise over 30 minutes. The reaction was heated at 75° C. for 2 hours then cooled to room temperature overnight. Mixture was acidified by the addition of aqueous 4M HCl to adjust pH to 2. The reaction mixture was filtered to remove any insoluble material and the filtrate was concentrated under reduced pressure to remove EtOH. The resulting aqueous solution was basified by the addition of aqueous 2M ammonium hydroxide solution to adjust pH to 10. The aqueous solution was diluted with dichloromethane and transferred to a separatory funnel and the organic layer collected. The aqueous layer was further extracted with dichloromethane and the combined organic layers were washed with $H_2O$, brine, and dried over magnesium sulphate, filtered and concentrated to afford a dark red oil. The product was purified using silica gel dry column chromatography with a solvent system of 5% 2M $NH_3$ in methanol/95% dichloromethane to afford an orange solid 52 N1-(1-Methyl-piperidin-4-yl)-4-nitro-benzene-1,2-diamine Yield: 0.342 grams (25.5%). $^1$H NMR (DMSO) δ: 1.42-1.55 (m, 2H), 1.89-1.93 (m, 2H), 1.97-2.05 (m, 2H), 2.17 (s, 3H), 2.70-2.81 (m, 2H), 3.30-3.42 (m, 1H), 5.20 (br s, 2H), 5.63 (br d, 1H, J=7.4), 6.53 (d, 1H, J=9.0), 7.39 (d, 1H, J=2.9), 7.49 (dd, 1H, J=8.9, 2.7); MS (ESI): 251 (MH$^+$, 100%).

Preparation of 53: N1-(1-Methyl-piperidin-4-yl)-4-nitro-benzene-1,2-diamine 52 (0.330 g, 1.318 mmol) was dissolved in anhydrous dichloromethane (15 mL) in a small, argon purged flask fitted with an condenser and magnetic stirbar. (4-Ethoxy-phenyl)-acetic acid 5 (0.249 g, 1.384 mmol) followed by 2-Ethoxy-1-ethoxycarbonyl-1,2-dihydroquinoline (0.391 g, 1.582 mmol) are added quickly as solids and resulting solution heated to reflux for 14 hours. After cooling to room temperature the solvent was removed under reduced pressure and the resulting residue partitioned between $H_2O$ and chloroform and 2M ammonium hydroxide solution added to adjust pH to 10. The mixture was transferred to a separatory funnel and the organic layer collected. The aqueous layer was further extracted with chloroform and the combined organic layers were washed with brine, dried over magnesium sulphate, filtered and concentrated to afford crude. Recrystallization of the crude from ethyl acetate yielded a yellow solid 53 2-(4-Ethoxy-phenyl)-N-[2-(1-methyl-piperidin-4-ylamino)-5-nitro-phenyl]-acetamide. Yield: 0.200 grams (36.8%). $^1$H NMR (DMSO) δ: 1.31 (t, 3H, J=6.9), 1.41-1.56 (m, 2H), 1.86-1.89 (m, 2H), 1.99-2.07 (m, 2H), 2.17 (s, 3H), 2.69-2.73 (m, 2H), 3.37-3.45 (m, 1H), 3.61 (s, 2H), 4.00 (q, 2H, J=7.0), 5.89 (d, 1H, J=7.5), 6.81 (d, 1H, J=9.3), 6.89 (d, 2H, J=8.4), 7.26 (d, 2H, J=8.3), 7.92 (dd, 1H, J=9.3, 2.3), 8.10 (d, 1H, J=2.3), 9.47 (br s, 1H); MS (ESI): 413 (MH$^+$, 100%).

Preparation of 54: 2-(4-Ethoxy-phenyl)-N-[2-(1-methyl-piperidin-4-ylamino)-5-nitro-phenyl]-acetamide 53 (190 mg, 0.461 mmol), Phosphorous pentachloride (100.7 mg, 0.483 mmol) were dissolved in anhydrous chloroform (10 mL) in a small, argon purged flask fitted with an condenser and magnetic stirbar. The solution was heated to reflux in an oil bath for 4 hours and cooled to room temperature overnight. The solid that had precipitated from the reaction mixture was collected on a sintered glass funnel and washed with a small amount of chloroform. The sticky solid was washed off the funnel in methanol and concentrated to residue. The residue was taken up in $H_2O$ and chloroform and 2M ammonium hydroxide solution added to adjust pH to 9-10. The mixture was transferred to a separatory funnel and the organic layer collected. The aqueous layer was further extracted with chloroform and the combined organic layers were washed with brine, dried over magnesium sulphate, filtered and concentrated to afford crude. The product was purified using silica gel column chromatography eluting with a solvent system of 5% 2M $NH_3$ in methanol/95% dichloromethane to afford a pale yellow oil 54 2-(4-Ethoxy-benzyl)-1-(1-methyl-piperidin-4-yl)-5-nitro-1H-benzimidazole Yield: 127 mg (70.0%). $^1$H NMR (DMSO) δ: 1.29 (t, 3H, J=7.0), 1.39 (br d, 2H, J=9.8), 1.89-1.97 (m, 2H), 2.19 (s, 3H), 2.20-2.31 (m, 2H), 2.82 (br d, 2H, J=11.2), 3.96 (q, 2H, J=7.0), 4.29-4.37 (m, 1H), 4.37 (s, 2H), 6.87 (d, 2H, J=8.7), 7.17 (d, 2H, J=8.4), 7.82 (d, 1H, J=9.0), 8.07 (dd, 1H, J=9.0, 2.4), 8.48 (d, 1H, J=2.3); MS (ESI): 395 (MH$^+$, 100%).

Preparation of 56: 2-(4-Ethoxy-benzyl)-1-(1-methyl-piperidin-4-yl)-5-nitro-1H-benzimidazole 54 (120 mg, 0.304 mmol) was dissolved in anhydrous ethanol (10 mL) in a dry argon purged flask. Palladium, 10 wt % on activated carbon (32.4 mg, 0.0304 mmol) is quickly added and the atmosphere from the flask evacuated by vacuum pump and replaced with hydrogen from a balloon. The atmosphere is evacuated from the flask and replaced with hydrogen twice more and the mixture stirred under a hydrogen atmosphere at room temperature. After 22 hours, thin layer chromatography in a solvent system of (5% 2M $NH_3$ in methanol/95% dichloromethane) shows complete conversion to 55, 2-(4-Ethoxy-benzyl)-1-(1-methyl-piperidin-4-yl)-1H-benzoimidazol-5-ylamine, which is utilized without isolation. The mixture is filtered through a pad of celite to remove insolubles, the pad washed with anhydrous ethanol 10 mL) and the ethanolic solution of the amine 55 is charged to a small, argon purged flask fitted with a magnetic stirbar. Thiophene-2-carboximidothioic acid methyl ester hydroiodide 9a (173.4 mg, 0.608 mmol) is added to the flask and the reaction was stirred under Ar at ambient temperature for 30 hours. The solvent was removed and the residue partitioned between $H_2O$ and ethyl acetate and 1M sodium hydroxide solution added to adjust pH to 10. The mixture was transferred to a separatory funnel and the organic layer collected. The aqueous layer was further extracted with ethyl acetate and the combined organic layers were washed with brine (twice), dried over magnesium sulphate, filtered and concentrated to afford crude product. The product was purified using silica gel dry column chromatography eluting with a solvent system of 5% 2M $NH_3$ in methanol/95% dichloromethane to afford a pale yellow-colorless residue 56 N-[2-(4-Ethoxy-benzyl)-1-(1-methyl-piperidin-4-yl)-1H-benzoimidazol-5-yl]-thiophene-2-carboxamidine Yield: 80 mg (55.5%). $^1$H NMR (DMSO) δ: 1.28 (t, 3H, J=6.9), 1.31-1.42 (m, 2H), 1.91 (br t, 2H, J=11.0), 2.19 (s, 3H), 2.19-2.35 (m, 2H), 2.81 (m, 2H), 3.96 (q, 2H, J=7.0), 4.16-4.32 (s, 2H, m, 1H), 6.36 (br s, 2H), 6.69 (dd, 1H, J=8.7, 1.6), 6.85 (d, 2H, J=8.7), 7.00 (d, 1H, J=1.5), 7.08-7.11 (m, 1H), 7.17 (d, 2H, J=8.5), 7.46 (d, 1H, J=8.5), 7.59 (d, 1H, J=5.3), 7.73-7.75 (m, 1H); MS (ESI): 474 (MH$^+$, 80%), 377 (100%).

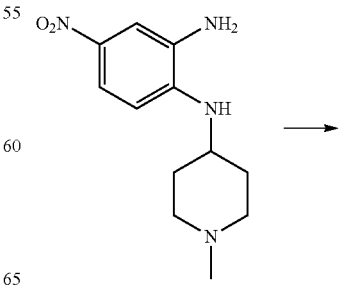

52

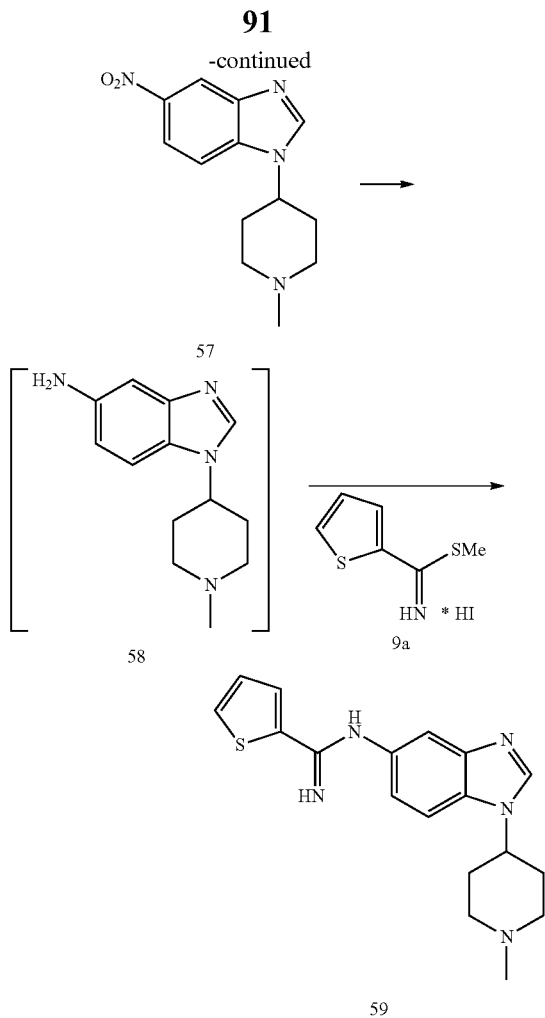

Preparation of 57: N1-(1-methylpiperidin-4-yl)-4-nitrobenzene-1,2-diamine (compound 52, 100 mg, 0.399 mmol), and Formic acid (3 mL) were placed in an argon-purged flask fitted with a stir bar and condenser and heated to reflux for 2 hours. The solution was cooled to room temperature, diluted with H$_2$O and ethyl acetate and 3M sodium hydroxide solution added to adjust pH to 8-9. The mixture was transferred to a separatory funnel and the organic layer collected. The aqueous layer was further extracted with ethyl acetate and the combined organic layers were washed with H$_2$O, brine and dried over magnesium sulphate. The solution was filtered and concentrated to afford an off white solid 57 (77 mg, 74.0% yield); $^1$H NMR (DMSO) δ: 1.94-2.18 (m, 6H), 2.24 (s, 3H), 2.87-3.00 (m, 2H), 4.42-4.57 (m, 1H), 7.94 (d, 1H, J=9.0), 8.18 (dd, 1H, J=8.9, 2.1), 8.55 (d, 1H, J=2.2), 8.71 (s, 1H); MS (ESI+): 261 (MH$^+$, 100%).

Preparation of 59: 1-(1-methylpiperidin-4-yl)-5-nitro-1H-benzo[d]imidazole (compound 57, 75 mg, 0.288 mmol) was dissolved in anhydrous ethanol (7 mL) in a dry argon purged flask. Palladium, 10 wt % on activated carbon (30.6 mg, 0.0288 mmol) is quickly added and the atmosphere from the flask evacuated by vacuum pump and replaced with hydrogen from a balloon. The atmosphere is evacuated from the flask and replaced with hydrogen twice more and the mixture stirred under a hydrogen atmosphere at room temperature. After 3 hours, thin layer chromatography in a solvent system of (5% 2M NH$_3$ in methanol/95% dichloromethane) shows complete conversion to 58, 1-(1-methylpiperidin-4-yl)-1H-benzo[d]imidazol-5-amine, which is utilized without isolation. The mixture is filtered through a pad of celite to remove insolubles, the pad washed with anhydrous ethanol (7 mL) and the ethanolic solution of the amine 58 is charged to a small, argon purged flask fitted with a magnetic stir bar. Thiophene-2-carboximidothioic acid methyl ester hydroiodide 9a (164 mg, 0.576 mmol) is added to the flask and the reaction was stirred under Ar at ambient temperature for 19 hours, at which time the solvent was evaporated and the residue was partitioned between H$_2$O and ethyl acetate and 1M sodium hydroxide solution added to adjust pH to 8-9. The mixture was transferred to a separatory funnel and the organic layer collected. The aqueous layer was further extracted with ethyl acetate and the combined organic layers were washed with brine, dried over magnesium sulphate, filtered, concentrated and purified using dry silica gel column chromatography eluting with 30 mL portions of solvent system (5% 2M NH$_3$ in methanol/95% dichloromethane) to afford off-white solid 59 (40 mg, 40.9% yield); $^1$H NMR (DMSO) δ: 1.97-2.17 (m, 6H), 2.24 (s, 3H), 2.87-2.98 (m, 2H), 4.22-4.37 (m, 1H), 6.35 (br s, 2H), 6.77 (dd, 1H, J=8.4, 1.4), 7.05 (d, 1H, J=1.3), 7.08-7.11 (m, 1H), 7.55 (d, 1H, J=8.5), 7.60 (d, 1H, J=5.2), 7.74 (d, 1H, J=3.4), 8.25 (s, 1H); MS (ESI+): 340 (MH$^+$, 100%).

Example 6 nNOS (Human), eNOS (Human) and iNOS (Human) Enzyme Assay

A compound of the invention can be examined for its efficacy in preferentially inhibiting nNOS and/or iNOS and/or eNOS by methods known to those skilled in the art. Following is an exemplary procedure.

Inducible, endothelial, or neuronal NO synthase activity were determined by measuring the conversion of [$^3$H]L-arginine to [$^3$H]L-citrulline by radiometric method. Recombinant human inducible NOS (iNOS), human endothelial constitutive NOS (eNOS) or human neuronal constitutive NOS (nNOS) were produced in Baculovirus-infected Sf9 cells (ALEXIS). To measure iNOS, 10 μL of enzyme was added to 100 μL of 100 mM HEPES, pH=7.4, containing 1 mM CaCl$_2$, 1 mM EDTA, 1 mM dithiotheitol, 1 μM FMN, 1 μM FAD, 10 μM tetrahydrobiopterin, 120 μM NADPH, 100 nM CaM. To measure constitutive NOS isoforms (eNOS, nNOS), 10 μL of enzyme was added to 100 μL of 40 mM HEPES, pH=7.4, containing 2.4 mM CaCl$_2$, 1 mM MgCl$_2$, 1 mg/ml BSA, 1 mM EDTA, 1 mM dithiothreitol, 1 μM FMN, 1 μM FAD, 10 μM tetrahydrobiopterin, 1 mM NADPH, 1.2 μM CaM. Test substances (15 μL) were added to the mixture with the specific enzyme and pre-incubated at RT for 15 min. The reaction was initiated by addition of 20 μL-arginine containing 0.25 μCi of [$^3$H] arginine/ml and 24 μM L-arginine and incubations carried out at 37° C. for 45 min. The reaction was stopped by adding 20 μL of ice-cold buffer containing 100 mM HEPES, 3 mM EGTA, 3 mM EDTA, pH=5.5. [$^3$H]L-Citrulline was separated by DOWEX (ion-exchange resin DOWEX 50 W×8-400, SIGMA) by spinning at 12,000 g for 10 min in the centrifuge. An aliquot 70 μL of the supernatant was added to 100 μL scintillation fluid and samples were counted in a liquid scintillation counter (1450 Microbeta Jet, Wallac). Specific NOS activity was reported as the difference between the activity (total) and that in the presence of the inhibitor L-NMMA (non-specific) in the final concentration of 240 μM. The total volume of the reaction mixture was 150 μL in every well. All assays were performed at least in duplicate. Standard deviations were 10% or less. As shown in Table 2, compounds 10 and 11 selectively inhibit nNOS activity.

TABLE 2

| Compound # | h-nNOS IC50 (uM) | h-eNOS IC50 (uM) | h-iNOS IC50 (uM) |
|---|---|---|---|
| 10 | 0.44 | 4.7 | |
| 11 | 0.74 | 17 | |
| 12 | >100 | >100 | |
| 13 | 5.0 | 28.0 | 15.0 |
| 14 | 14.4 | 117 | |
| 15 | 46.9 | 47.1 | |
| 16 | 5.74 | 56.4 | 75.0 |
| 20 | 0.833 | >100 | |
| 22 | 2.09 | >100 | |
| 34 | 113 | 317 | |
| 36 | 1.77 | 4.04 | |
| 45 | 37.2 | 47.1 | |
| 56 | 12.8 | 8.00 | |
| 59 | 1.72 | 6.66 | |

Example 7

Human Mu-Opioid Receptor G-Protein Coupling Assay; Agonist Effect

Compounds of the invention can be examined for their efficacy in the preferential activation of the mu-opioid receptor by methods known to those skilled in the art. Following is an exemplary procedure.

Human mu-opioid receptor functional activity assays were performed as previously described (Wang et al., *FEBS Lett.* 338: 217-222, 1994 and *Proc. Natl. Acad. Sci USA* 30:10230-10234, 1993). HEK-293 cells expressing human mu-opioid receptor were incubated 5 min at 37° C. in the presence of test compounds or Tyr-D-Ala-Gly-(N-Me)Phe-Gly-ol (DAMGO) at different concentrations. Forskolin (20 mM)-stimulated cAMP accumulation was measured using the HTRF method. The $EC_{50}$ values (concentration causing half-maximal stimulation of control values) were determined by non-linear regression analysis of the concentration-response curves using Hill equation curve fitting. As shown in Table 3, compounds 10 and 11 exhibited mu opioid agonist activity.

TABLE 3

| Compound # | Functional EC50 (uM) | Binding IC50 (uM) |
|---|---|---|
| DAMGO | 0.003 | 0.0009 |
| 10 | 0.34 | 0.013 |
| 11 | 1.5 | 0.31 |
| 12 | 0.94 | |
| 13 | 0.4 | 0.066 |
| 14 | | 0.1 |
| 15 | | 0.018 |
| 34 | | 0.0011 |
| 36 | | 0.41 |
| 56 | | 7.0 |

OTHER EMBODIMENTS

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

Other embodiments are in the claims.

What is claimed is:
1. A compound having the formula:

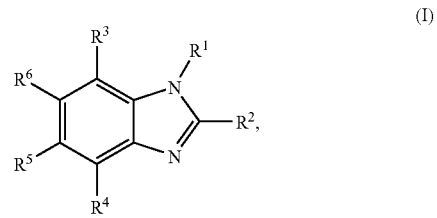

(I)

or a pharmaceutically acceptable salt thereof, wherein,
$R^1$ is substituted $C_{1-6}$ alkyl, optionally substituted $C_{1-4}$ alkaryl, optionally substituted $C_{1-4}$ alkheterocyclyl, or optionally substituted $C_{2-9}$ heterocyclyl;
$R^2$ is H, Hal, optionally substituted $C_{1-6}$ alkyl, optionally substituted $C_{6-10}$ aryl, optionally substituted $C_{1-4}$ alkaryl, optionally substituted $C_{2-9}$ bridged heterocyclyl, optionally substituted $C_{1-4}$ bridged alkheterocyclyl, optionally substituted $C_{2-9}$ heterocyclyl, or optionally substituted $C_{1-4}$ alkheterocyclyl;
each of $R^3$ and $R^4$ is, independently, H, F, $C_{1-6}$ alkyl, or $C_{1-6}$ alkoxy;
$R^5$ is H, $R^{5A}C(NH)NH(CH_2)_{r5}$—, $R^{5A}NHC(NH)NH(CH_2)_{r5}$—, or $R^{5B}NHC(S)NH(CH_2)_{r5}$—, where r5 is an integer from 0 to 2; $R^{5A}$ is optionally substituted $C_{1-6}$ alkyl, optionally substituted $C_{6-10}$ aryl, optionally substituted $C_{1-4}$ alkaryl, optionally substituted $C_{2-9}$ heterocyclyl, optionally substituted $C_{1-4}$ alkheterocyclyl, optionally substituted $C_{1-6}$ thioalkoxy, optionally substituted $C_{1-6}$ thioalkyl, optionally substituted $C_{1-4}$ thioalkaryl, optionally substituted aryloyl, optionally substituted $C_{1-4}$ thioalkheterocyclyl, or nitro; $R^{5B}$ is optionally substituted $C_{2-9}$ heterocyclyl, optionally substituted $C_{1-4}$ alkheterocyclyl, optionally substituted $C_{1-6}$ thioalkoxy, optionally substituted $C_{1-6}$ thioalkyl, optionally substituted aryloyl, optionally substituted $C_{1-4}$ thioalkaryl, optionally substituted $C_{1-4}$ thioalkheterocyclyl, or nitro; and
$R^6$ is H, $R^{6A}C(NH)NH(CH_2)_{r6}$—, $R^{6A}NHC(NH)NH(CH_2)_{r6}$—, or $R^{6A}NHC(S)NH(CH_2)_{r6}$—, where r6 is an integer from 0 to 2 and $R^{6A}$ is optionally substituted $C_{1-6}$ alkyl, optionally substituted $C_{6-10}$ aryl, optionally substituted $C_{1-4}$ alkaryl, optionally substituted $C_{2-9}$ heterocyclyl, optionally substituted $C_{1-4}$ alkheterocyclyl, optionally substituted $C_{1-6}$ thioalkoxy, optionally substituted $C_{1-4}$ thioalkaryl, optionally substituted aryloyl, optionally substituted $C_{1-4}$ thioalkheterocyclyl, or nitro;
where one, but not both, of $R^5$ and $R^6$ is H, and wherein when $R^1$ is substituted $C_{1-6}$ alkyl, said substituted $C_{1-6}$ alkyl is substituted with one, two, three or, in the case of substituted $C_{2-6}$ alkyl groups, four substituents independently selected from the group consisting of: (1) $C_{1-6}$ alkoxy; (2) $C_{1-6}$ alkylsulfinyl; (3) $C_{1-6}$ alkylsulfonyl; (4) $C_{6-10}$ aryl; (5) $C_{6-10}$ aryl-$C_{1-6}$ alkoxy; (6) aryloyl; (7)

azido; (8) carboxaldehyde; (9) $C_{3-8}$ cycloalkyl; (10) halo; (11) $C_{2-9}$ heterocyclyl; (12) ($C_{2-9}$ heterocycle)oxy; (13) ($C_{2-9}$ heterocycle)oyl; (14) hydroxyl; (15) N-protected amino; (16) nitro; (17) oxo; (18) $C_{3-8}$ spiroalkyl; (19) $C_{1-6}$ thioalkoxy; (20) $C_{6-10}$ aryl-$C_{1-6}$ thioalkoxy; (21) thiol; (22) —$CO_2R^A$, where $R^A$ is selected from the group consisting of (a) $C_{1-6}$ alkyl, (b) $C_{6-10}$ aryl and (c) $C_{1-6}$ alkaryl; (23) —C(O)$NR^BR^C$, where each of $R^B$ and $R^C$ is, independently, selected from the group consisting of (a) hydrogen, (b) $C_{1-6}$ alkyl, (c) $C_{6-10}$ aryl and (d) $C_{1-6}$ alkaryl; (24) —$SO_2R^D$, where $R^D$ is selected from the group consisting of (a) $C_{1-6}$ alkyl, (b) $C_{6-10}$ aryl and (c) $C_{1-6}$ alkaryl; (25) —$SO_2NR^ER^F$, where each of $R^E$ and $R^F$ is, independently, selected from the group consisting of (a) hydrogen, (b) $C_{1-6}$ alkyl, (c) $C_{6-10}$ aryl and (d) $C_{1-6}$ alkaryl; and (26) —$NR^GR^H$, where each of $R^G$ and $R^H$ is, independently, selected from the group consisting of (a) hydrogen; (b) an N-protecting group; (c) optionally substituted $C_{1-6}$ alkyl; (d) $C_{2-6}$ alkenyl; (e) $C_{2-6}$ alkynyl; (f) optionally substituted $C_{6-10}$ aryl; (g) optionally substituted $C_{1-6}$ alkaryl; (h) optionally substituted $C_{3-8}$ cycloalkyl; (i) $C_{1-10}$ alk-$C_{3-8}$cycloalkyl; (j) $C_{2-9}$ heterocyclyl, or (k) optionally substituted $C_{1-4}$ alkheterocyclyl, with the proviso that no two groups are bound to the nitrogen atom through a carbonyl group or a sulfonyl group.

2. The compound of claim 1, wherein,
$R^1$ is substituted $C_{1-6}$ alkyl, optionally substituted $C_{1-4}$ alkaryl, or optionally substituted $C_{1-4}$ alkheterocyclyl;
$R^2$ is, independently, H, Hal, optionally substituted $C_{1-6}$ alkyl, optionally substituted $C_{6-10}$ aryl, optionally substituted $C_{1-4}$ alkaryl, optionally substituted $C_{2-9}$ heterocyclyl, or optionally substituted $C_{1-4}$ alkheterocyclyl;
each of $R^3$ and $R^4$ is, independently, H, F, $C_{1-6}$ alkyl, or $C_{1-6}$ alkoxy;
$R^5$ is H or $R^{5A}C(NH)NH(CH_2)_{r5}$—, wherein r5 is an integer from 0 to 2, $R^{5A}$ is optionally substituted $C_{1-6}$ alkyl, optionally substituted $C_{6-10}$ aryl, optionally substituted $C_{1-4}$ alkaryl, optionally substituted $C_{2-9}$ heterocyclyl, optionally substituted $C_{1-4}$ alkheterocyclyl, optionally substituted $C_{1-6}$ thioalkoxy, optionally substituted $C_{1-4}$ thioalkaryl, or optionally substituted $C_{1-4}$ thioalkheterocyclyl; and
$R^6$ is H or $R^{6A}C(NH)NH(CH_2)_{r6}$—, wherein r6 is an integer from 0 to 2, $R^{6A}$ is optionally substituted $C_{1-6}$ alkyl, optionally substituted $C_{6-10}$ aryl, optionally substituted $C_{1-4}$ alkaryl, optionally substituted $C_{2-9}$ heterocyclyl, optionally substituted $C_{1-4}$ alkheterocyclyl, optionally substituted $C_{1-6}$ thioalkoxy, optionally substituted $C_{1-4}$ thioalkaryl, or optionally substituted $C_{1-4}$ thioalkheterocyclyl.

3. The compound of claim 1, wherein $R^1$ is optionally substituted $C_{1-4}$ alkheterocyclyl, or an alkylamine-substituted $C_{1-6}$ alkyl.

4. The compound of claim 3, wherein said alkylamine-substituted $C_{1-6}$ alkyl is selected from the group consisting of 2-(N,N-dimethylamino)-ethyl, and 2-(N,N-diethylamino)-ethyl.

5. The compound of claim 3, wherein said $C_{1-4}$ alkheterocyclyl is selected from the group consisting of 2-(N-aziridinyl)-ethyl, 2-(N-azetidanyl)-ethyl, 2-(N-pyrrolidinyl)-ethyl, 2-(N-piperidinyl)-ethyl, 2-(N-methyl-2-pyrrolidinyl)-ethyl, 2-(N-methyl-4-piperidinyl)-ethyl, and 2-(N-morpholinyl)-ethyl.

6. The compound of claim 1, wherein r5 or r6 is 0.

7. The compound of claim 1, wherein $R^{5A}$ is methyl, fluoromethyl, ethyl, n-propyl, i-propyl, n-butyl, i-butyl, t-butyl, thiomethoxy, thioethoxy, thio-n-propyloxy, thio-1-propyloxy, thio-n-butyloxy, thio-1-butyloxy, thio-t-butyloxy, phenyl, benzyl, 2-thienyl, 3-thienyl, 2-furanyl, 3-furanyl, 2-oxazole, 4-oxazole, 5-oxazole, 2-thiazole, 4-thiazole, 5-thiazole, 2-isoxazole, 3-isoxazole, 4-isoxazole, 2-isothiazole, 3-isothiazole, or 4-isothiazole.

8. The compound of claim 1, wherein $R^{6A}$ is methyl, fluoromethyl, ethyl, n-propyl, i-propyl, n-butyl, i-butyl, t-butyl, thiomethoxy, thioethoxy, thio-n-propyloxy, thio-1-propyloxy, thio-n-butyloxy, thio-1-butyloxy, thio-t-butyloxy, phenyl, benzyl, 2-thienyl, 3-thienyl, 2-furanyl, 3-furanyl, 2-oxazole, 4-oxazole, 5-oxazole, 2-thiazole, 4-thiazole, 5-thiazole, 2-isoxazole, 3-isoxazole, 4-isoxazole, 2-isothiazole, 3-isothiazole, or 4-isothiazole.

9. The compound of claim 1, wherein one or both of $R^1$ and $R^2$ is not H.

10. The compound of claim 1, wherein $R^1$ is $(CH_2)_{m1}X^1$, wherein $X^1$ is selected from the group consisting of:

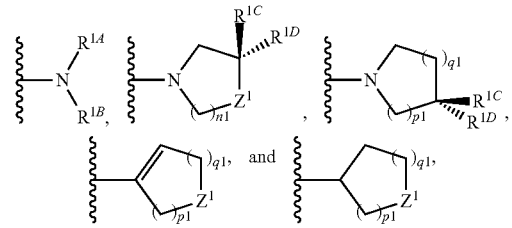

wherein
each of $R^{1A}$ and $R^{1B}$ is, independently, H, optionally substituted $C_{1-6}$ alkyl, optionally substituted $C_{3-8}$ cycloalkyl, optionally substituted $C_{6-10}$ aryl, optionally substituted $C_{1-4}$ alkaryl, $C_{2-9}$ heterocyclyl, or optionally substituted $C_{1-4}$ alkheterocyclyl;
each of $R^{1C}$ and $R^{1D}$ is, independently, H, OH, $CO_2R^{1E}$, or $NR^{1F}R^{1G}$, wherein each of $R^{1E}$, $R^{1F}$, and $R^{1G}$ is, independently, H, optionally substituted $C_{1-6}$ alkyl, optionally substituted $C_{3-8}$ cycloalkyl, optionally substituted $C_{6-10}$ aryl, optionally substituted $C_{1-4}$ alkaryl, $C_{2-9}$ heterocyclyl, or optionally substituted $C_{1-4}$ alkheterocyclyl, or $R^{1C}$ and $R^{1D}$ together with the carbon they are bonded to are C=O;
$Z^1$ is $NR^{1H}$, $NC(O)R^{1H}$, $NC(O)OR^{1H}$, $NC(O)NHR^{1H}$, $NC(S)R^{1H}$, $NC(S)NHR^{1H}$, $NS(O)_2R^{1H}$, O, S(O), S(O)$_2$, or S, wherein $R^{1H}$ is H, optionally substituted $C_{1-6}$ alkyl, optionally substituted $C_{3-8}$ cycloalkyl, optionally substituted $C_{6-10}$ aryl, optionally substituted $C_{1-4}$ alkaryl, $C_{2-9}$ heterocyclyl, or optionally substituted $C_{1-4}$ alkheterocyclyl, with the proviso that when $Z^1$ is $NC(O)OR^{1H}$, $R^{1H}$ is not H;
m1 is an integer of 2 to 6;
n1 is an integer of 1 to 4;
p1 is an integer of 0 to 2; and
q1 is an integer of 0 to 5.

11. The compound of claim 1, wherein $R^2$ is $(CH_2)_{m2}X^2$, wherein $X^2$ is selected from the group consisting of:

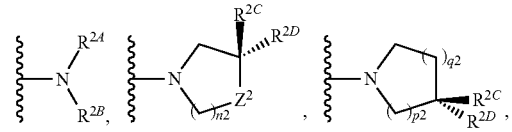

-continued

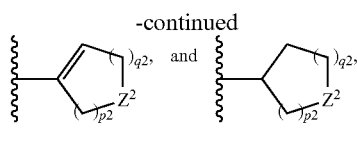

wherein
- each of $R^{2A}$ and $R^{2B}$ is, independently, H, optionally substituted $C_{1-6}$ alkyl, optionally substituted $C_{3-8}$ cycloalkyl, optionally substituted $C_{6-10}$ aryl, optionally substituted $C_{1-4}$ alkaryl, $C_{2-9}$ heterocyclyl, or optionally substituted $C_{1-4}$ alkheterocyclyl;
- each of $R^{2C}$ and $R^{2D}$ is, independently, H, OH, $CO_2R^{2E}$, or $NR^{2F}R^{2G}$, wherein each of $R^{2E}$, $R^{2F}$, and $R^{2G}$ is, independently, H, optionally substituted $C_{1-6}$ alkyl, optionally substituted $C_{3-8}$ cycloalkyl, optionally substituted $C_{6-10}$ aryl, optionally substituted $C_{1-4}$ alkaryl, $C_{2-9}$ heterocyclyl, or optionally substituted $C_{1-4}$ alkheterocyclyl, or $R^{2C}$ and $R^{2D}$ together with the carbon they are bonded to are C=O;
- $Z^2$ is $NR^2H$, $NC(O)R^{2H}$, $NC(O)OR^{2H}$, $NC(O)NHR^{2H}$, $NC(S)R^{2H}$, $NC(S)NHR^{2H}$, $NS(O)_2R^{2H}$, O, S(O), $S(O)_2$, or S, wherein $R^{2H}$ is H, optionally substituted $C_{1-6}$ alkyl, optionally substituted $C_{3-8}$ cycloalkyl, optionally substituted $C_{6-10}$ aryl, optionally substituted $C_{1-4}$ alkaryl, $C_{2-9}$ heterocyclyl, or optionally substituted $C_{1-4}$ alkheterocyclyl, with the proviso that when $Z^2$ is $NC(O)OR^{2H}$, $R^{2H}$ is not H;
- m2 is an integer of 2 to 6;
- n2 is an integer of 1 to 4;
- p2 is an integer of 0 to 2; and
- q2 is an integer of 0 to 5.

12. The compound of claim 1 or 2, wherein $R^1$ is $(CH_2)_{m1}X^1$, wherein $X^1$ is selected from the group consisting of:

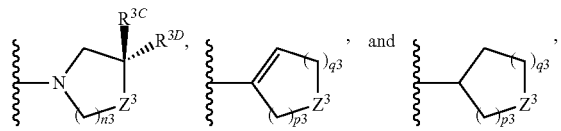

wherein
- each of $R^{3C}$ and $R^{3D}$ is, independently, H, OH, $CO_2R^{3E}$, or $NR^{3F}R^{3G}$, wherein each of $R^{3E}$, $R^{3F}$, and $R^{3G}$ is, independently, H, optionally substituted $C_{1-6}$ alkyl, optionally substituted $C_{3-8}$ cycloalkyl, optionally substituted $C_{6-10}$ aryl, optionally substituted $C_{1-4}$ alkaryl, $C_{2-9}$ heterocyclyl, or optionally substituted $C_{1-4}$ alkheterocyclyl, or $R^{3C}$ and $R^{3D}$ together with the carbon they are bonded to are C=O;
- $Z^3$ is $NC(NH)R^{3H}$, wherein $R^{3H}$ is H, optionally substituted $C_{1-6}$ alkyl, optionally substituted $C_{3-8}$ cycloalkyl, optionally substituted $C_{6-10}$ aryl, optionally substituted $C_{1-4}$ alkaryl, $C_{2-9}$ heterocyclyl, or optionally substituted $C_{1-4}$ alkheterocyclyl;
- m1 is an integer of 0 to 6;
- n3 is an integer of 1 to 4;
- p3 is an integer of 0 to 2; and
- q3 is an integer of 0 to 5.

13. The compound of claim 1 or 2, wherein $R^2$ is $(CH_2)_{m2}X^2$, wherein $X^2$ is selected from the group consisting of:

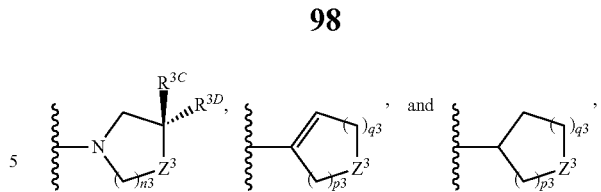

wherein
- each of $R^{3C}$ and $R^{3D}$ is, independently, H, OH, $CO_2R^{3E}$, or $NR^{3F}R^{3G}$, wherein each of $R^{3E}$, $R^{3F}$, and $R^{3G}$ is, independently, H, optionally substituted $C_{1-6}$ alkyl, optionally substituted $C_{3-8}$ cycloalkyl, optionally substituted $C_{6-10}$ aryl, optionally substituted $C_{1-4}$ alkaryl, $C_{2-9}$ heterocyclyl, or optionally substituted $C_{1-4}$ alkheterocyclyl, or $R^{3C}$ and $R^{3D}$ together with the carbon they are bonded to are C=O;
- $Z^3$ is $NC(NH)R^{3H}$, wherein $R^{3H}$ is H, optionally substituted $C_{1-6}$ alkyl, optionally substituted $C_{3-8}$ cycloalkyl, optionally substituted $C_{6-10}$ aryl, optionally substituted $C_{1-4}$ alkaryl, $C_{2-9}$ heterocyclyl, or optionally substituted $C_{1-4}$ alkheterocyclyl;
- m2 is an integer of 0 to 6;
- n3 is an integer of 1 to 4;
- p3 is an integer of 0 to 2; and
- q3 is an integer of 0 to 5.

14. The compound of claim 1, wherein $R^1$ or $R^2$ is

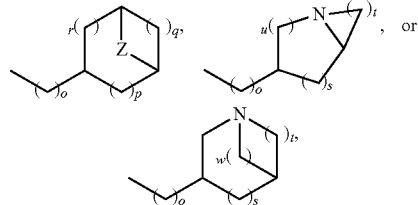

wherein Z is $NR^Z$, o is an integer from 0-3, p is an integer from 1 to 2, q is an integer from 0 to 2, r is an integer from 0 to 1, s is an integer from 0 to 3, u is an integer from 0 to 1, t is an integer from 2 to 7, w is an integer from 0 to 2; and wherein said $R^Z$ is independently, H, optionally substituted $C_{1-6}$ alkyl, optionally substituted $C_{3-8}$ cycloalkyl, optionally substituted $C_{6-10}$ aryl, optionally substituted $C_{1-4}$ alkaryl, $C_{2-9}$ heterocyclyl, or optionally substituted $C_{1-4}$ alkheterocyclyl.

15. The compound of claim 1, wherein $R^2$ is

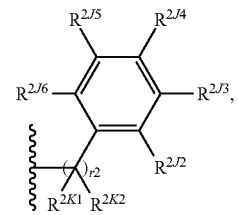

wherein each of $R^{2J2}$, $R^{2J3}$, $R^{2J4}$, $R^{2J5}$, and $R^{2J6}$ is, independently, H, $C_{1-6}$ alkyl; OH; $C_{1-6}$ alkoxy; SH; $C_{1-6}$ thioalkoxy; Halo; $NO_2$; CN; $CF_3$; $OCF_3$; NR where each of $R^{2Ja}$ and $R^{2Jb}$ is, independently, H or $C_{1-6}$ alkyl; C(O)$R^{2k}$, where $R^{2Jc}$ is H or $C_{1-6}$ alkyl; $CO_2R^{2Jd}$, where $R^{2Jd}$ is H or $C_{1-6}$ alkyl; tetrazolyl; C(O)$NR^{2Je}R^{2Jf}$, where each of $R^{2Je}$ and $R^{2Jf}$ is, independently, H or $C_{1-6}$ alkyl; OC(O)$R^{2Jg}$, where $R^{2Jg}$ is $C_{1-6}$ alkyl; NHC(O)$R^{2Jh}$, where R[2Jh] is H or C$_{1-6}$ alkyl; SO$_3$H; S(O)$_2$NR[2Ji]R[2Jj], where each of R[2Ji] and R[2Jj] is, independently, H or C$_{1-6}$ alkyl; S(O)R[2Jk], where R[2Jk] is C$_{1-6}$ alkyl; and S(O)$_2$R[2Jl], where R[2Jl] is C$_{1-6}$ alkyl, r2 is an integer of 0 to 2, and each of R[2K1] and R[2K2] is, independently H or C$_{1-6}$ alkyl.

16. The compound of claim 15, wherein r2 is 1, and R[2J2], R[2J3], R[2J5], R[2J6], R[2K1], and R[2K2] are H.

17. The compound of claim 16, wherein R[2J4] is methoxy, ethoxy, n-propyloxy, isopropyloxy, dimethylamino, diethylamino, thiomethoxy, thioethoxy, n-propyl, isopropyl, or cyclopropyl.

18. A compound selected from the group consisting of

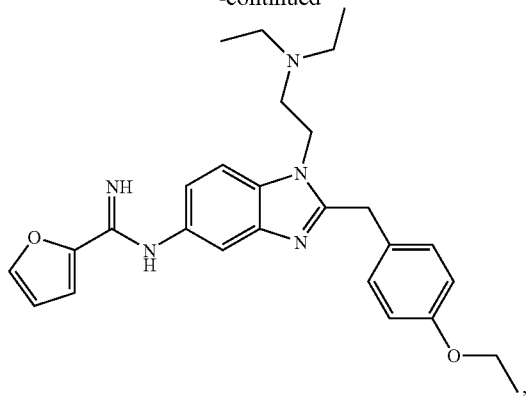

-continued

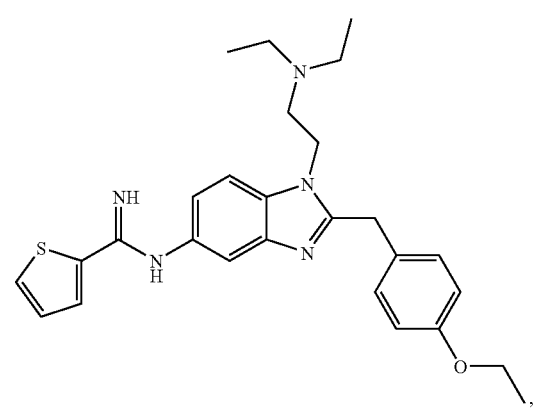

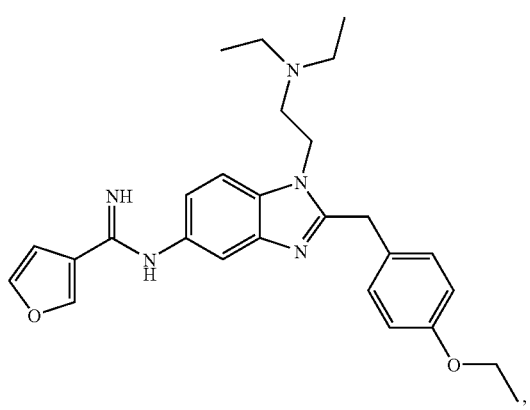

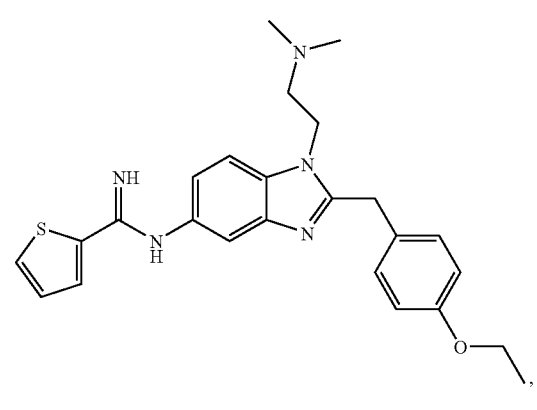

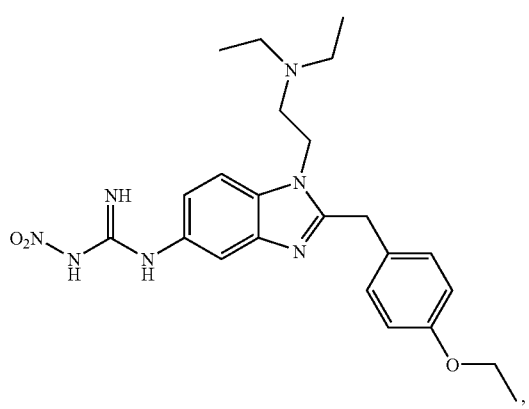

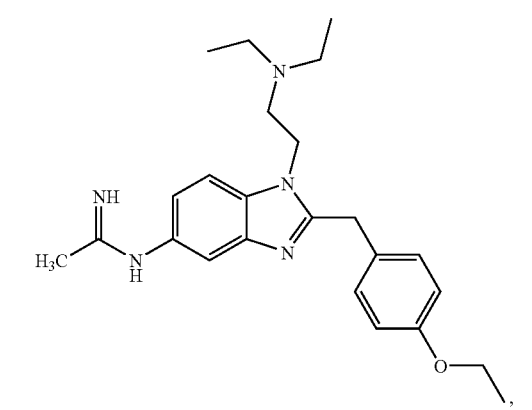

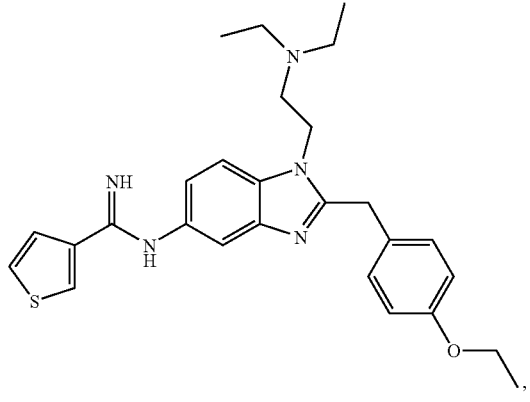

101
-continued
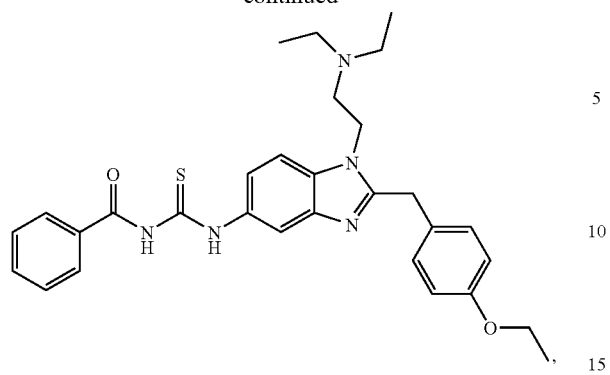
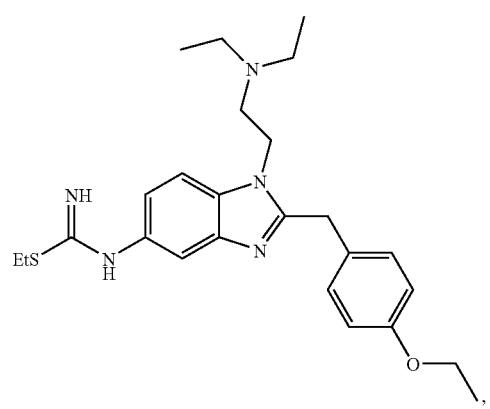
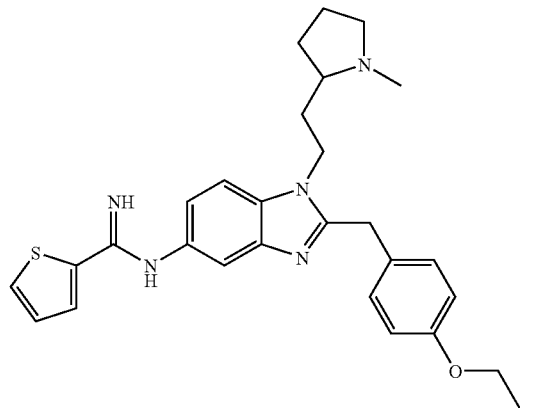
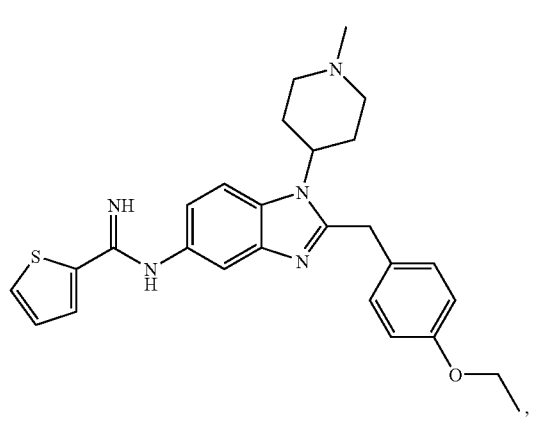
102
-continued
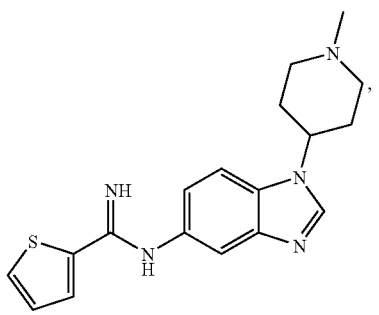
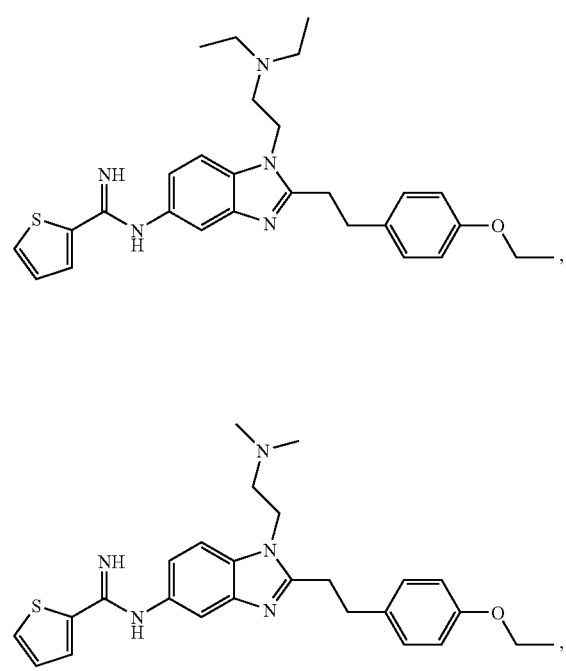
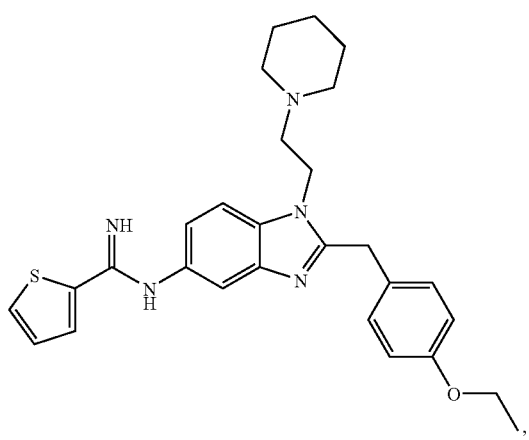

103
-continued
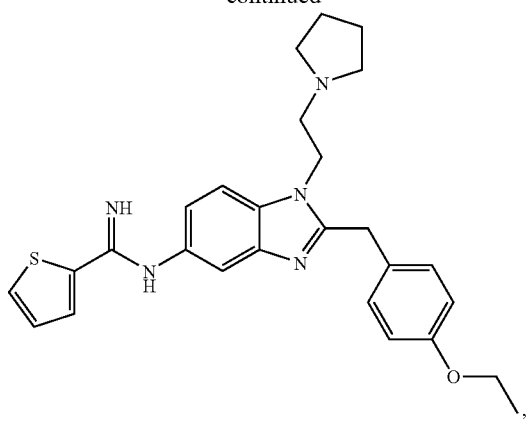
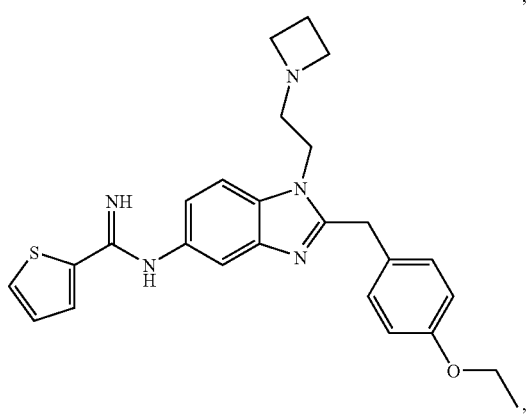
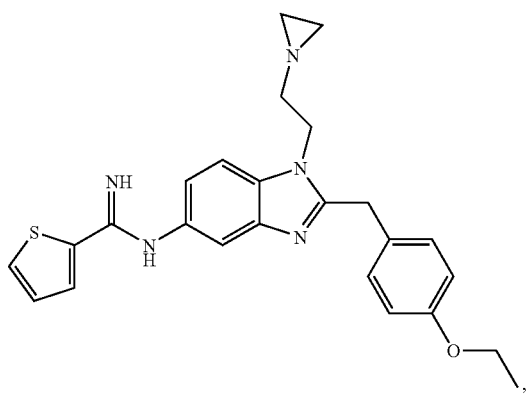
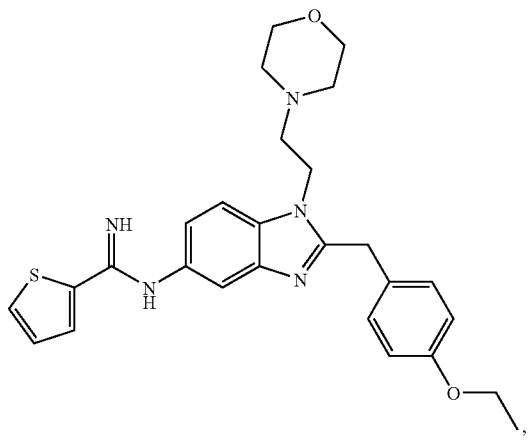
104
-continued
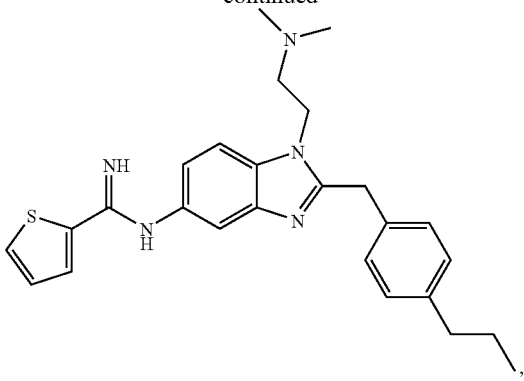
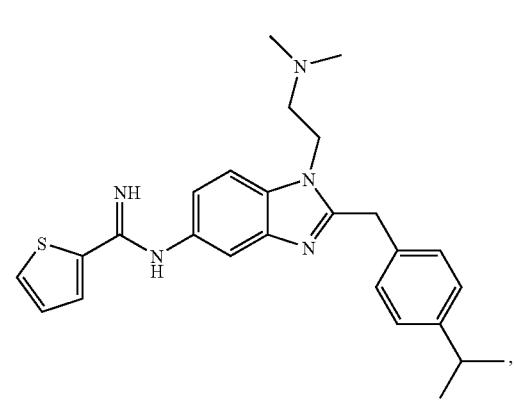
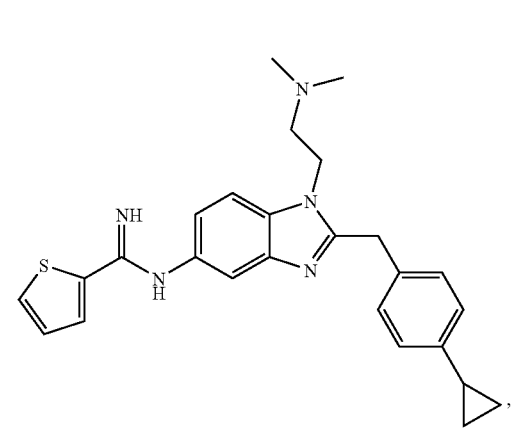
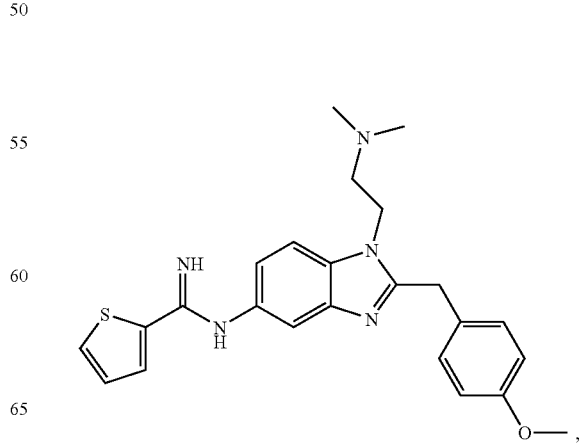

105
-continued
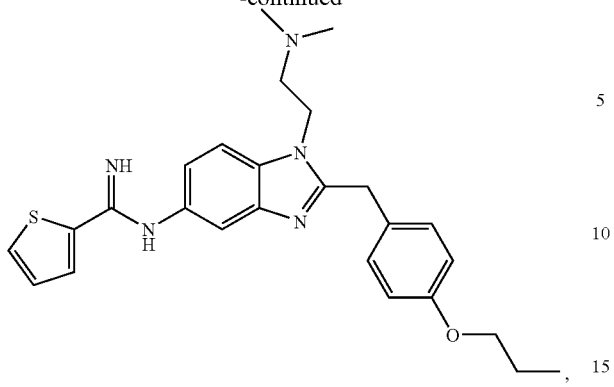,
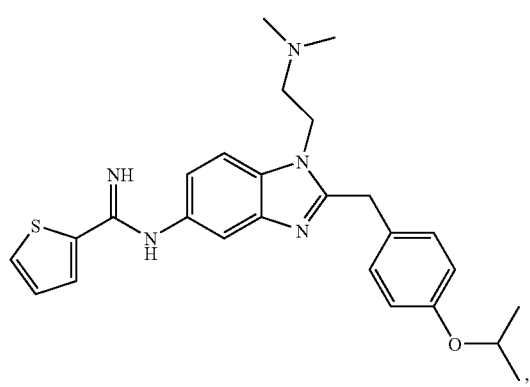,
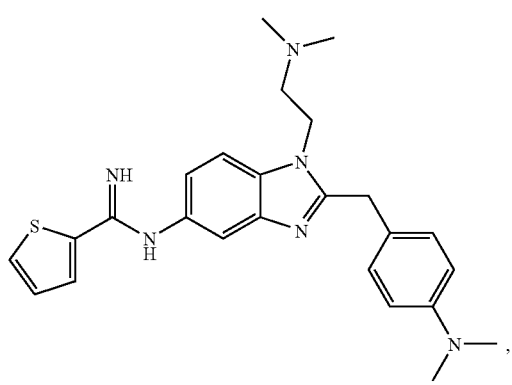,
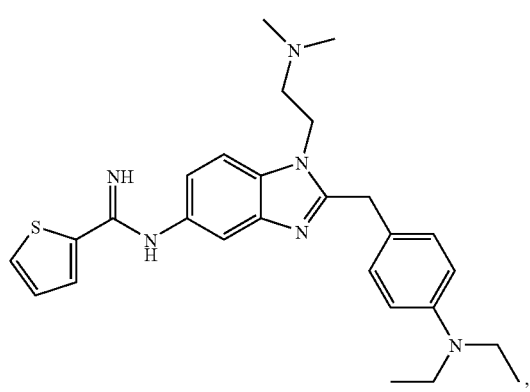,
106
-continued
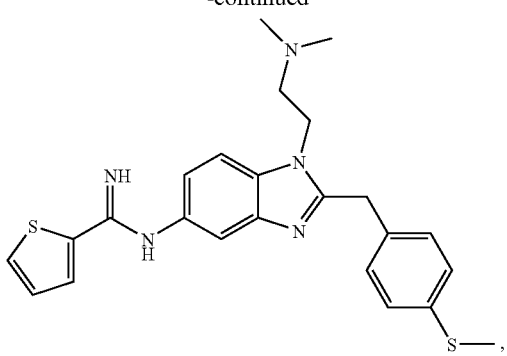,
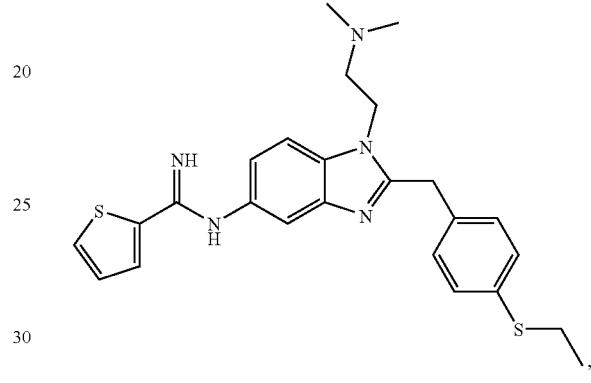,
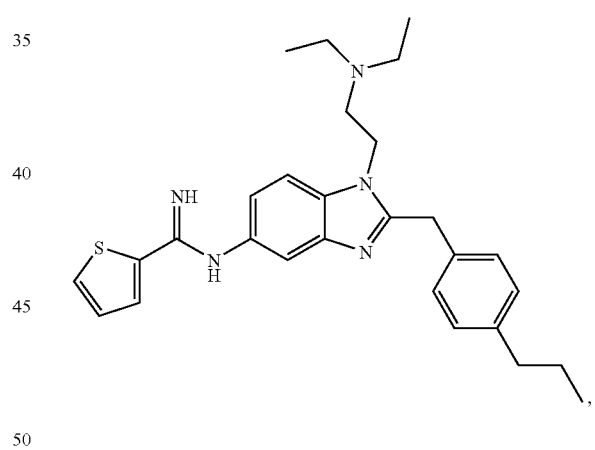,
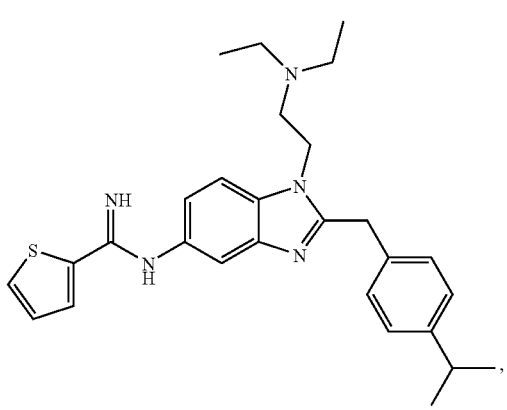,

107
-continued
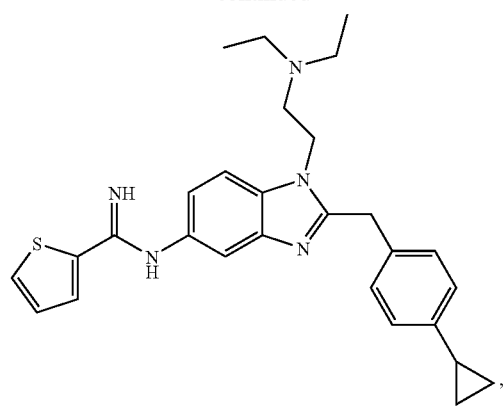
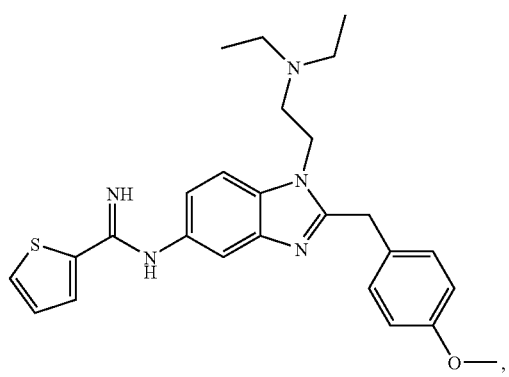
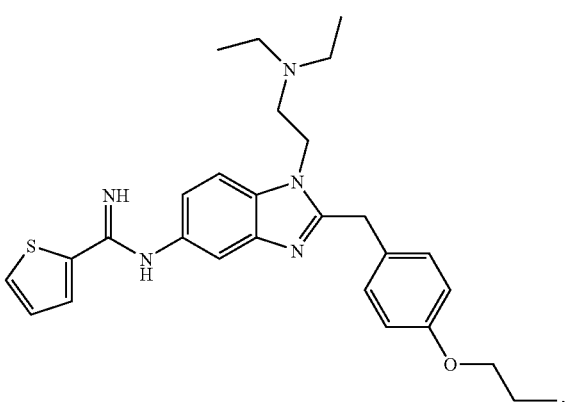
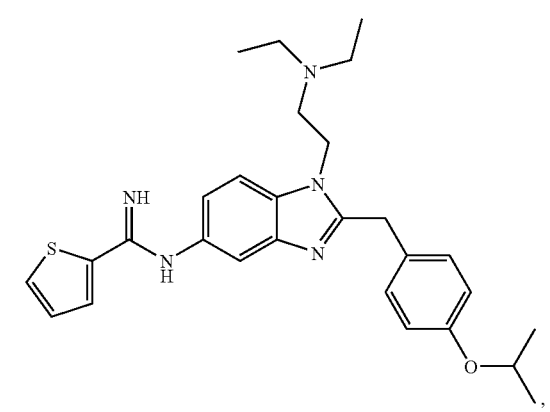
108
-continued
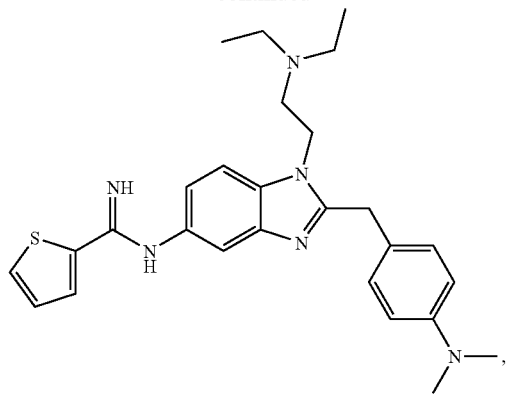
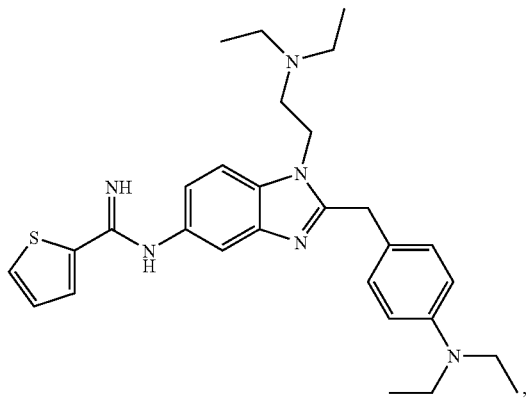
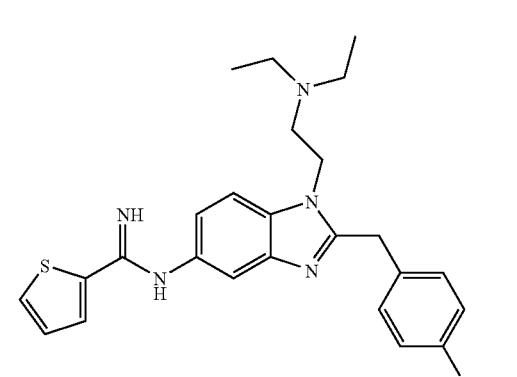
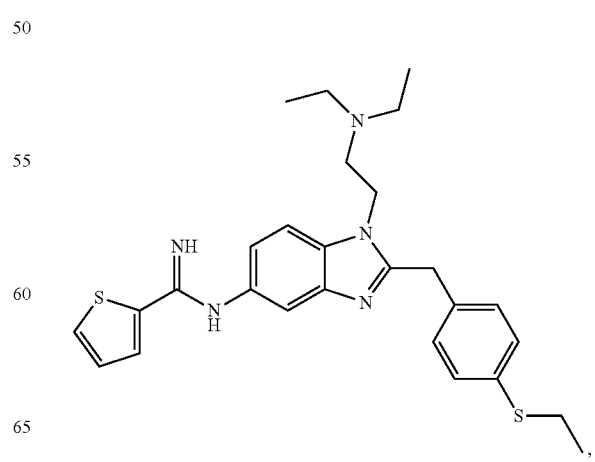

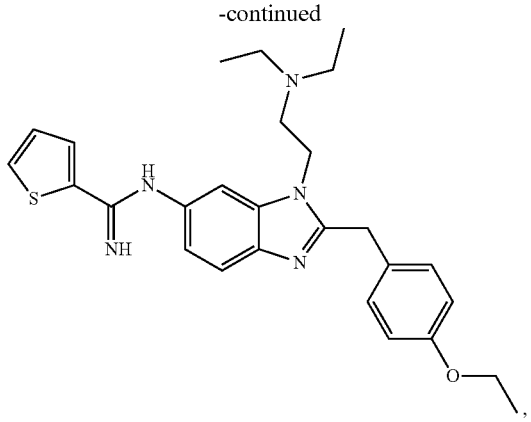

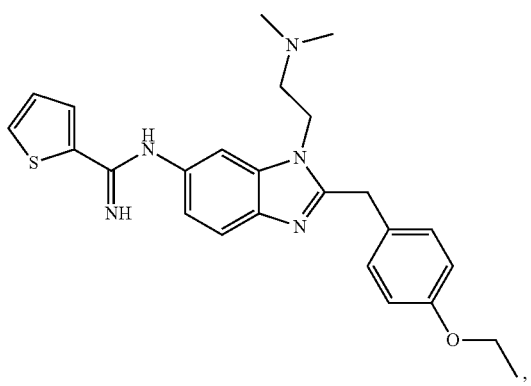

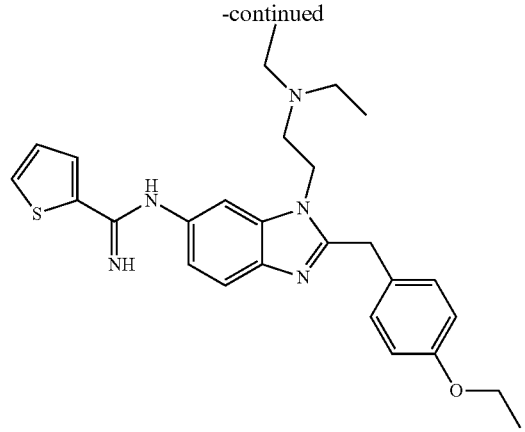

and pharmaceutically acceptable salts thereof.

19. The compound of claim 1, wherein said compound selectively inhibits neuronal nitric oxide synthase (nNOS) over endothelial nitric oxide synthase (eNOS).

20. The compound of claim 1, wherein said compound is active in an in vitro opioid receptor assay with an $EC_{50}$ of 2 μM or less.

21. The compound of claim 20, wherein said opioid receptor is the mu opioid receptor.

22. The compound of claim 21, wherein said compound is a mu opioid receptor agonist.

23. A pharmaceutical composition comprising the compound of claim 1 and a pharmaceutically acceptable excipient.

24. The compound of claim 1, wherein $R^{5B}$ is thiomethoxy, thioethoxy, thio-n-propyloxy, thio-i-propyloxy, thio-n-butyloxy, thio-i-butyloxy, thio-t-butyloxy, 2-thienyl, 3-thienyl, 2-furanyl, 3-furanyl, 2-oxazole, 4-oxazole, 5-oxazole, 2-thiazole, 4-thiazole, 5-thiazole, 2-isoxazole, 3-isoxazole, 4-isoxazole, 2-isothiazole, 3-isothiazole, or 4-isothiazole.

* * * * *

UNITED STATES PATENT AND TRADEMARK OFFICE
CERTIFICATE OF CORRECTION

PATENT NO. : 7,919,510 B2
APPLICATION NO. : 11/436393
DATED : April 5, 2011
INVENTOR(S) : Renton et al.

It is certified that error appears in the above-identified patent and that said Letters Patent is hereby corrected as shown below:

Column 17, Line 34, replace "posseses" with --possesses--.

Column 18, Line 34, replace "opiod" with --opioid--.

Column 24, Line 35, replace "(27) -NR$^H$R$^H$," with --(27) -NR$^G$R$^H$,--.

Column 32, Line 41, replace "R$^5$" with --R$^{5A}$--.

Column 47, Line 16, replace "VIIa and VIb." with --VIIa and VIIb.--.

Column 48, Line 42, replace "(Pd$_2$ dba$_3$)" with --(Pd$_2$dba$_3$)--;

Line 43, replace "Pd$_2$ dba$_3$" with --Pd$_2$dba$_3$--.

Column 53, Line 67, replace "opiod" with --opioid--.

Column 62, Line 35, replace "Similary" with --Similarly--;

Line 39, replace "striaital" with --striatal--;

Line 64, replace "straital" with --striatal--.

Column 64, Line 26, replace "SO$_{509}$" with --SO509--.

Column 67, Line 8, replace "paitents" with --patients--;

Line 49, replace "vasodialator" with --vasodilator--.

Signed and Sealed this
Third Day of July, 2012

David J. Kappos
*Director of the United States Patent and Trademark Office*

Column 71, replace " 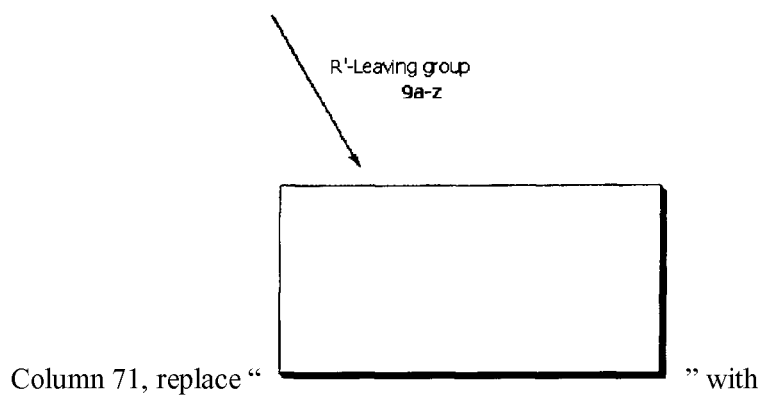 " with 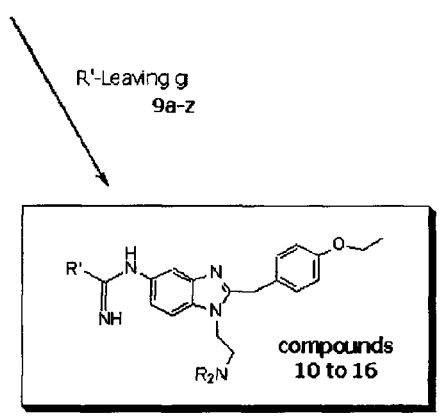 --.
Column 77, replace " 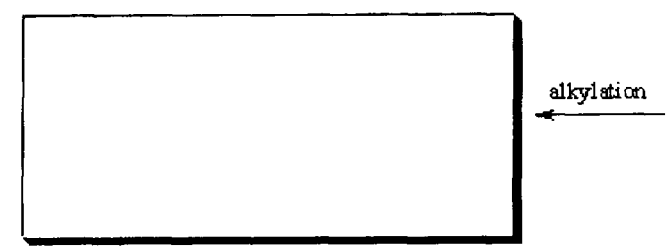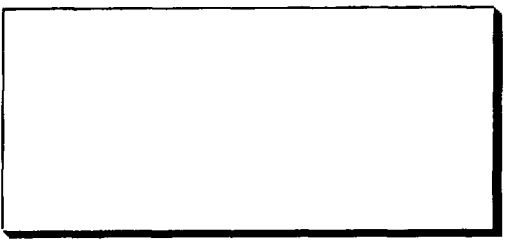 " with 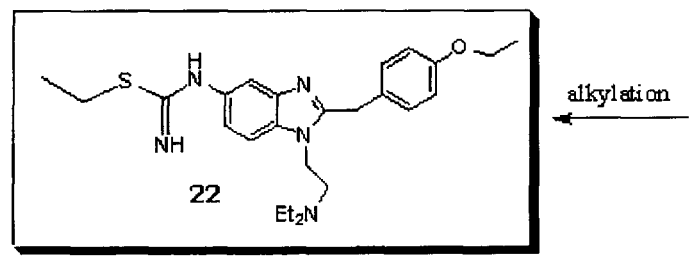 --.
Column 78, Line 46, replace "80.81" with --0.81--.
Column 81, Line 35, replace "8-1.51-1.71" with --δ: 1.51-1.71--.

CERTIFICATE OF CORRECTION (continued)
U.S. Pat. No. 7,919,510 B2

Column 84, replace " 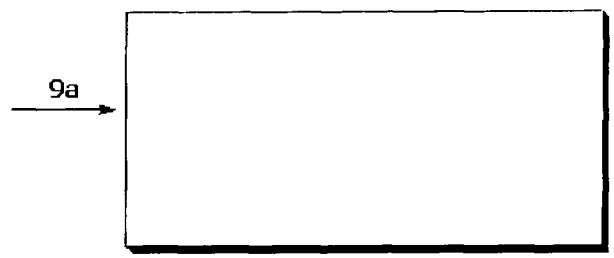 " with

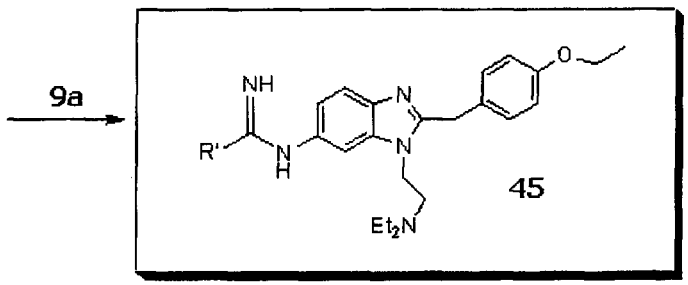

--.

Column 87, Line 62, replace "IM ammonium hydroxide" with --1M ammonium hydroxide--.

Column 88, replace " 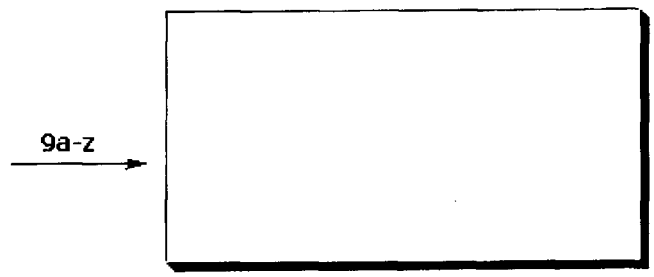 " with

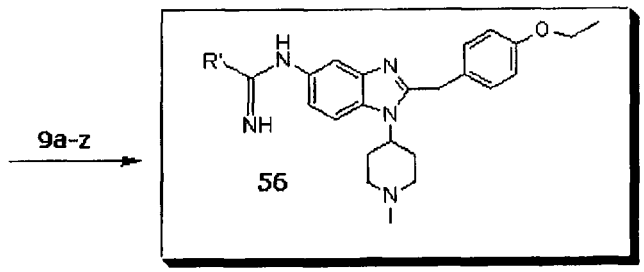

--.

Column 92, Line 53, replace "20 µL-arginine" with --20 µL L-arginine--.

Column 96, Claim 7, Line 2, replace "thio-1-butyloxy" with --thio-i-butyloxy--;

Claim 8, Lines 9-10, replace "thio-1-propyloxy" with --thio-i-propyloxy--;

Claim 8, Line 10, replace "thio-1-butyloxy" with --thio-i-butyloxy--.

CERTIFICATE OF CORRECTION (continued)
U.S. Pat. No. 7,919,510 B2

Column 98, Claim 15, Line 62, replace "NR" with --$NR^{2Ja}R^{2Jb}$--;

Claim 15, Lines 63-64, replace "$C(O)R^{2k}$" with --$C(O)R^{2Jc}$--.